(12) United States Patent
Abe et al.

(10) Patent No.: US 7,459,451 B2
(45) Date of Patent: Dec. 2, 2008

(54) PYRAZOLOPYRIDINE DERIVATIVES

(75) Inventors: Yoshito Abe, Tokyo (JP); Kazuhiko Ohne, Tokyo (JP); Kentaro Sato, Tokyo (JP); Makoto Inoue, Tokyo (JP); Mitsuaki Okumura, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 433 days.

(21) Appl. No.: 11/171,320

(22) Filed: Jul. 1, 2005

(65) Prior Publication Data

US 2006/0004003 A1    Jan. 5, 2006

(30) Foreign Application Priority Data

Jul. 5, 2004    (AU) ............................... 2004903691

(51) Int. Cl.
*A61K 31/535* (2006.01)
*A61K 31/44* (2006.01)
*A01N 43/42* (2006.01)
*C07D 413/00* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. .................. 514/234.2; 514/303; 546/119; 546/120; 544/127

(58) Field of Classification Search ............... 546/119, 546/120; 514/303, 234.2; 544/127
See application file for complete search history.

(56) References Cited

U.S. PATENT DOCUMENTS 5,024,999 A * 6/1991 Fujikawa et al. ............. 514/63
2005/0075342 A1   4/2005 Abe et al.

OTHER PUBLICATIONS

Mainou-Fowler et al., Leukemia and Lymphoma, 2000, vol. 38, p. 547-552.*
U.S. Appl. No. 11/171,320, filed Jul. 1, 2005, Abe et al.

* cited by examiner

*Primary Examiner*—D. Margaret Seaman
*Assistant Examiner*—Niloofar Rahmani
(74) *Attorney, Agent, or Firm*—Oblon, Spivak, McClelland, Maier & Neustadt, P.C.

(57) ABSTRACT

The invention relates to compound of the formula (I) or its salt, in which $R^1$, $R^2$, $R^3$ and $R^4$ are as defined in the description, their use of as medicament, the process for their preparation and use for the treatment of PDE-IV or TNF-α mediated diseases.

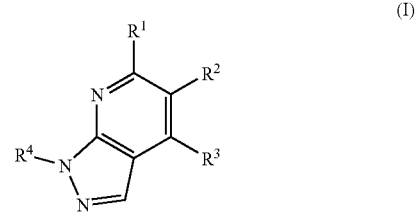

(I)

12 Claims, No Drawings

PYRAZOLOPYRIDINE DERIVATIVES

TECHNICAL FIELD

This invention relates to new pyrazolopyridine derivatives and pharmaceutically acceptable salts thereof which inhibit enzymatic activity of phosphodiesterase IV (PDE IV) and production of tumor necrosis factor-α (TNF-α).

BACKGROUND ART

Cyclic adenosine monophosphate (adenosine 3',5'-cyclic monophosphate, "cAMP" or "cyclic AMP") is known as an intracellular second messenger, which is intermediate a first messenger (hormone, neurotransmitter or autacoid) and the cellular responses. The first messenger stimulates the enzyme responsible for synthesis of cAMP, and then the cAMP intervenes in many functions such as metabolic, contractile or secretory. The effect of cAMP end when it is degraded by cyclic nucleotide phosphodiesterases, in particular phosphodiesterase-4 (PDE4 or PDE-IV), which is specific for cAMP. PDE-IV have been identified in many tissues including the central nervous systems, the heart, vascular smooth muscle, airway smooth muscle, myeloid lines, lymphoid, and the like. Evaluation of cAMP level by using the PDE-IV inhibitor would produce beneficial effect on inappropriate activation of airway smooth muscle and a wide variety of inflammatory cells.

A major concern with the use of PDE-IV inhibitors is the side effect of emesis which has been observed for several candidate compounds as described in C. Burnouf et al., (Ann. Rep. In Med. Chem., 33:91-109(1998)). Burnouf describe the wide variation of the severity of the undesirable side effects exhibited by various compounds.

Some condensed heterocyclic derivatives having the inhibitory activity of PDE-IV have been known, for example in WO03/016279, WO03/018579, WO03/000679 and the like. 4-amino derivatives of pyrazolopyridine having the inhibitory activity of PDE-IV have been known in WO2004/024728. However, there remains a need for novel compounds that inhibit PDE-IV with minimal side effects.

DISCLOSURE OF INVENTION

This invention relates to new pyrazolopyridine derivatives.

The compounds of this invention inhibit cAMP phosphodiesterase enzymes, in particular phosphodiesterase-4 enzyme, and also inhibit the production of tumor necrosis factor-α (TNF-α), a serum glycoprotein.

Accordingly, one object of this invention is to provide the new and useful pyrazolopyridine derivatives and pharmaceutically acceptable salts thereof which possess a strong phosphodiesterase-4 (PDE IV)-inhibitory activity and a strong inhibitory activity on the production of tumor necrosis factor (TNF).

Another object of this invention is to provide processes for preparation of the pyrazolopyridine derivatives and salts thereof.

A further object of this invention is to provide a pharmaceutical composition comprising said pyrazolopyridine derivatives or a pharmaceutically acceptable salt thereof.

Still further object of this invention is to provide a use of said pyrazolopyridine derivatives or a pharmaceutically acceptable salt thereof as a medicament for prophylactic and therapeutic treatment of PDE-IV and TNF mediated diseases such as chronic inflammatory diseases, specific autoimmune diseases, sepsis-induced organ injury, and the like in human being and animals.

The object pyrazolopyridine derivatives of the present invention are novel and can be represented by the following general formula (I):

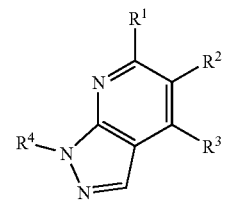

in which
$R^1$ is (1) lower alkyl optionally substituted by halogen, cyclo(lower)alkyl, lower alkoxy, hydroxy, protected hydroxy, cyclo(lower)alkoxy, aryloxy, hydroxyimino, carbamoyloxy optionally substituted by lower alkyl, or substituted or unsubstituted heterocyclyl (wherein said lower alkoxy is optionally substituted by cyclo(lower)alkyl, substituted or unsubstituted aryl, or substituted or unsubstituted heteroaryl),
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;
$R^2$ is $R^5$ or $-(A^1)p-X-A^2-R^5$,
wherein
p is 0 or 1
$A^1$ is $(C_1-C_2)$alkylene or $-CH=CH-$;
$A^2$ is a divalent heterocyclic group, or $-(CH_2)_n-$ or $-(CH=CR)_m-$ [wherein n is integer which may range from 1 to 6 and m is integer which may range from 1 to 3];
X is single bond, $-CH_2-$ or $-O-$, and
$R^5$ is hydroxy, protected hydroxy, cyano, acyl, carboxy, protected carboxy, hydroxyimino(lower)alkyl, or $-CONR^6R^7$
[wherein $R^6$ is hydrogen or lower alkyl, and $R^7$ is hydrogen or $-(CH_2)_q-Y-R^8$ (wherein q is 0, 1, 2 or 3, Y is bond, $-O-$, or $-CH(R^9)-CH_2-$ (wherein $R^9$ is lower alkyl, carboxy or protected carboxy), and $R^8$ is (1) substituted or unsubstituted aryl, (2) substituted or unsubstituted heteroaryl, (3) substituted or unsubstituted heterocyclyl, (4) substituted or unsubstituted cyclo(lower)alkyl, or (5) hydroxy, lower alkoxy or carboxy), or alternatively $R^6$ and $R^7$, together with the nitrogen atom to which they are attached, represent substituted or unsubstituted azaheterocyclyl group];
$R^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and $R^4$ is lower alkyl, or a pharmaceutically acceptable salt thereof, or prodrug thereof.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt, a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride; hydrobromide, sulfate, phosphate, etc.); an organic carboxylic or sulfonic acid addition salt (e.g., formate, acetate, trifluoroacetate, maleate, tartrate, fumarate, methanesulfonate, benzenesulfonate, toluenesulfonate, etc.); a salt with a basic or acidic amino acid (e.g., arginine, aspartic acid, glutamic acid, etc.).

The "prodrug" means the derivatives of the object compound (I) having a chemically or metabolically degradable group, which became pharmaceutically active after chemo- or biotransformation.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies.

Preferred embodiments of the object compound of the present invention are as follows.

(a) The pyrazolopyridine compound of the general formula (I)
in which
$R^1$ is (1) lower alkyl optionally substituted by halogen, cyclo(lower)alkyl, lower alkoxy, hydroxy, lower alkyl-diphenyl-silyloxy, cyclo(lower)alkoxy, phenoxy, hydroxyimino, carbamoyloxy optionally substituted by lower alkyl, or a radical of saturated monocyclic ring system comprising 5 or 6 ring atoms and containing one to three heteroatom(s) selected from the group consisting of nitrogen, oxygen and sulfur [wherein said lower alkoxy is optionally substituted by cyclo(lower)alkyl, aryl, or a radical of aromatic monocyclic ring system comprising 5 or 6 ring atoms and containing one to three heteroatom(s) selected from the group consisting of nitrogen, oxygen and sulfur, said radical is optionally substituted by lower alkyl],
(2) lower alkenyl optionally substituted by cyano or carbamoyl optionally substituted by aryl which may have halogen,
(3) cyclo(lower)alkyl,
(4) lower alkanoyl,
(5) cyano,
(6) phenyl optionally substituted by lower alkyl, lower alkoxy or halogen, or
(7) a radical of aromatic monocyclic ring system comprising 5 or 6 ring atoms and containing one to three heteroatom(s) selected from the group consisting of nitrogen, oxygen and sulfur, which is optionally substituted by lower alkyl;

$R^2$ is $R^5$ or $-(A^1)_p$-X-$A^2$-$R^5$,
wherein
p is 0 or 1,
$A^1$ is $(C_1$-$C_2)$alkylene or —CH=CH—;
$A^2$ is a divalent group derived from a radical of saturated monocyclic ring system comprising 5 or 6 ring atoms and containing one to three heteroatom(s) selected from the group consisting of nitrogen, oxygen and sulfur, or —$(CH_2)_n$— or —$(CH=CH)_m$— (wherein n is integer which may range from 1 to 4 and m is 1 or 2);
X is single bond, —$CH_2$— or —O—, and
$R^5$ is hydroxy, protected hydroxy, cyano, lower alkanoyl, carboxy, esterified carboxy, hydroxyimino(lower)alkyl, or —$CONR^6R^7$
[wherein $R^6$ is hydrogen, and $R^7$ is —$(CH_2)_q$—Y—$R^8$ (wherein q is 0, 1, 2 or 3, Y is bond or —O—, and $R^8$ is phenyl or indanyl optionally substituted by lower alkoxy)];

$R^3$ is (1) phenyl optionally substituted by one or more substituent(s) selected from the group consisting of halogen, lower alkyl, lower alkoxy and amino,
(2) a radical of aromatic monocyclic ring system comprising 5 or 6 ring atoms and containing one to three heteroatom(s) selected from the group consisting of nitrogen, oxygen and sulfur, which is optionally substituted by lower alkyl, alkyne, halogen or lower alkoxy,
(3) tetrahydropyranyl,
(4) cyclohexyl, or
(5) cyclohexylmethyl or phenylethyl; and
$R^4$ is lower alkyl.

(b) The pyrazolopyridine compound of (a)
in which
$R^1$ is (1) lower alkyl optionally substituted by halogen, cyclo(lower)alkyl, lower alkoxy, hydroxy, lower alkyl-diphenyl-silyloxy, cyclo(lower)alkoxy, phenoxy, hydroxyimino, carbamoyloxy optionally substituted by lower alkyl, or morpholinyl [wherein said lower alkoxy is optionally substituted by cyclo(lower)alkyl, phenyl, or pyridyl optionally substituted by lower alkyl],
(2) lower alkenyl optionally substituted by cyano or carbamoyl optionally substituted by aryl which may have halogen,
(3) cyclo(lower)alkyl,
(4) lower alkanoyl,
(5) cyano,
(6) phenyl optionally substituted by lower alkyl, lower alkoxy or halogen, or
(7) oxazolyl or thienyl, each of which is optionally substituted by lower alkyl;

$R^2$ is $R^5$ or $-(A^1)_p$-X-$A^2$-$R^5$,
wherein $R^5$, $A^1$, p and X are each as defined in (a), and
$A^2$ is a divalent group derived from piperidine or piperazine, or —$(CH_2)_n$— or —$(CH=CH)_m$— (wherein n is integer which may range from 1 to 4 and m is 1 or 2);

$R^3$ is (1) phenyl optionally substituted by one or more substituent(s) selected from the group consisting of halogen, lower alkyl, lower alkoxy and amino,
(2) pyridyl or thienyl, each of which is optionally substituted by lower alkyl, alkyne, halogen or lower alkoxy,
(3) tetrahydropyranyl,
(4) cyclohexyl, or
(5) cyclohexylmethyl or phenylethyl; and $R^4$ is ethyl.

In the above and subsequent descriptions of the present specification, suitable examples and illustration of the various definitions which the present invention intends to include within the scope thereof are explained in detail as follows.

It is to be noted that these definitions apply regardless of whether a term is used by itself or in combination with other terms. Hence the definition of "alkyl" applies to "alkyl" as well as to the "alkyl" portions of "alkoxy", "alkylamino" etc.

The term "lower" is used to intend a group having 1 to 6, preferably 1 to 4, carbon atom(s), unless otherwise provided.

The term "lower alkyl" means straight or branched one having 1 to 6 carbon atom(s), such as methyl, ethyl, propyl, isopropyl, 1-ethylpropyl, 1,2-dimethylpropyl, 1-ethyl-2-methylpropyl, 2-ethyl-1-methylpropyl, butyl, isobutyl, sec-butyl, tert-butyl, 1-methylbutyl, 2-methylbutyl, 1,1-dimethylbutyl, 1,2-dimethylbutyl, 1,3-dimethylbutyl, 2,3-dimethylbutyl, 2,2-dimethylbutyl, 3,3-dimethylbutyl, 1-ethylbutyl, 2-ethylbutyl, 2,2-dimethylbutyl, 3,3-dimethylbutyl, pentyl, isopentyl, neopentyl, tert-pentyl, 1-methylpentyl, 2-methylpentyl, 3-methylpentyl, hexyl, isohexyl, and the like, and in which more preferable example may be $C_1$-$C_4$ alkyl.

The term "cyclo(lower)alkyl means cyclopropyl, cyclobutyl, cyclopentyl and cyclohexyl.

The term "lower alkenyl" means vinyl(ethenyl), 1-(or 2-)propenyl, 1-(or 2- or 3-)butenyl, 1-(or 2- or 3- or 4-)pentenyl, 1-(or 2- or 3- or 4- or 5-)hexenyl, 1-methylvinyl, 1-ethylvinyl, 1-(or 2-)methyl-1-(or 2-)propenyl, 1-(or 2-)ethyl-1-(or 2-)propenyl, 1-(or 2- or 3-)methyl-1-(or 2- or 3-)butenyl, and the like, in which more preferable example may be $C_2$-$C_4$ alkenyl.

The term "lower alkylene" may include straight or branched one such as methylene, ethylene, trimethylene, tetramethylene, pentamethylene, hexamethylene, methylmethylene, ethylethylene, propylene, and the like, in which more preferable example may be "$C_1$-$C_2$ alkylene" such as methylene or ehthylene, and the most preferable one may be methylene.

Suitable "lower alkoxy" may include methoxy, ethoxy, propoxy, isopropoxy, 1-ethylpropoxy, 1,2-dimethylpropoxy, 1-ethyl-2-methylpropoxy, 2-ethyl-1-methyl-propoxy, butoxy, isobutoxy, sec-butoxy, tert-butoxy, 1-methylbutoxy, 2-methylbutoxy, 1,1-dimethylbutoxy, 1,2-dimethylbutoxy, 1,3-dimethylbutoxy, 2,3-dimethylbutoxy, 2,2-dimethylbutoxy, 3,3-dimethylbutoxy, 1-ethylbutoxy, 2-ethylbutoxy, pentyloxy, isopentyloxy, neopentyloxy, tert-pentyloxy, 1-methylpentyloxy, 2-methylpentyloxy, 3-methylpentyloxy, hexyloxy, isohexyloxy, and the like.

The term "halogen" may include fluorine, bromine, chlorine and iodine.

The term "protected carboxy" means a carboxy group bonded to the carboxy-protecting group, which may include esterified carboxy and the like.

Suitable examples of the ester moieties of the esterified carboxy may include lower alkyl (e.g., methyl, ethyl, propyl, isopropyl, butyl, isobutyl, tert-butyl, pentyl or hexyl) which may have suitable substituent(s), for example, lower alkanoyloxy(lower)alkyl [e.g., acetoxymethyl, propionyloxymethyl, butyryloxymethyl, valeryloxymethyl, pivaloyloxymethyl, hexanoyloxymethyl or acetoxyethyl], halo(lower)alkyl (e.g., 2-iodoethyl or 2,2,2-trichloroethyl), and lower alkoxycarbonyloxy(lower)alkyl (e.g., methoxycarbonyloxymethyl or 2-methoxycarbonyloxyethyl); lower alkenyl (e.g., vinyl or allyl); lower alkynyl (e.g., ethynyl or propynyl); ar(lower) alkyl which may have suitable substituent(s) such as phenyl (lower)alkyl (e.g., benzyl, 4-methoxybenzyl, 4-nitrobenzyl, phenethyl, trityl, bis(methoxyphenyl)methyl, 3,4-dimethoxybenzyl or 4-hydroxy-3,5-di-tert-butylbenzyl); aryl which may have suitable substituent(s) (e.g., phenyl, 4-chlorophenyl, tolyl, tert-butylphenyl, xylyl, mesityl or cumenyl); and the like.

The term "protected hydroxy" means a hydroxy group bonded to the hydroxy-protecting group. Example of such hydroxy-protectnig group include tri(lower)alkylsilyl (e.g. trimethylsilyl, triethylsilyl, tert-butyl-dimethylsilyl, etc.), diaryl(lower)alkylsilyl (e.g. diphenyl-tert-butylsilyl, etc.), and the like. Further example of hydroxy-protecting group are well-known in organic synthesis and are described by T. W. Greene and P. G. M. Wuts, "Protective Groups in Organic Synthesis," Second Edition, John Wiley and Sons, New York, N.Y., which is herein incorporated by reference.

Suitable "acyl" and "acyl moiety" may include aliphatic acyl group, and acyl group containing an aromatic ring, which is referred to as aromatic acyl, or heterocyclic ring, which is referred to as heterocyclic acyl.

Suitable example of said acyl may be illustrated as follows:
Aliphatic acyl such as
lower alkanoyl (e.g., formyl, acetyl, propanoyl, butanoyl, 2-methylpropanoyl, pentanoyl, 2,2-dimethylpropanoyl, hexanoyl, etc.), in which preferable "lower alkanoyl" may include straight or branched one such as formyl, acetyl, propionyl, butyryl, and the like.
lower alkenoyl (e.g., acryloyl, 2-(or 3-)-butenoyl, 2-(or 3- or 4-)pentenoyl, 2-(or 3- or 4- or 5-)-hexenoyl, etc.);
lower alkadienoyl (e.g., heptadienoyl, hexadienoyl, etc.);
cyclo(lower)alkylcarbonyl (e.g., cyclopropylcarbonyl, cyclopentylcarbonyl, cyclohexylcarbonyl, etc.);
lower alkylglyoxyloyl (e.g., methylglyoxyloyl, ethylglyoxyloyl, propylglyoxyloyl, etc.);
lower alkoxyglyoxyloyl (e.g., methoxyglyoxyloyl, ethoxyglyoxyloyl, propoxyglyoxyloyl, etc.);
or the like;
Aromatic acyl such as
aroyl (e.g., benzoyl, toluoyl, naphthoyl, etc.);
ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl (lower)alkanoyl (e.g., naphthylacetyl, naphthylpropanoyl, naphthylbutanoyl, etc.), etc.];
ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.];
aryloxy(lower)alkanoyl (e.g., phenoxyacetyl, phenoxypropionyl, etc.);
arylglyoxyloyl (e.g., phenylglyoxyloyl, naphthylglyoxyloyl, etc.);
heterocyclic acyl such as
heterocycliccarbonyl;
heterocyclic(lower)alkanoyl (e.g., heterocyclicacetyl, heterocyclicpropanoyl, heterocyclicbutanoyl, heterocyclicpentanoyl, heterocyclichexanoyl, etc.);
heterocyclic(lower)alkenoyl (e.g., heterocyclicpropenoyl, heterocyclicbutenoyl, heterocyclicpentenoyl, heterocyclichexenoyl, etc.);
heterocyclicglyoxyloyl; heterocyclicoxycarbonyl; or the like.

Example of suitable acyl is lower alkanoyl (such as, formyl, acetyl and the like) and aroyl (such as, benzoyl, and the like).

The term "cyclo(lower)alkyl" means a non-aromatic mono- or multicyclic ring system comprising about 3 to about 10 carbon atoms, preferably about 5 to about 7 carbon atoms.

Non-limiting examples of suitable monocyclic cyclo(lower) alkyl include cyclopropyl, cyclopentyl, cyclohexyl, cycloheptyl and the like. Non-limiting examples of suitable multicyclic cyclo(lower)alkyls include bicycloheptyl (e.g. bicycle[2,2,1]heptyl etc.), adamantyl and the like.

The term "aryl" means a radical of mono- or bicyclic carbocyclic ring system having 6 to 10 cabon atoms and one or two aromatic rings. Non-limiting examples of aryl include phenyl, naphthyl, tetrahydronaphthyl, indanyl, indenyl and the like.

The term "heteroaryl" means a radical of aromatic monocyclic or-multicyclic ring system comprising about 3 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. A nitrogen atom of a heteroaryl can be optionally oxidized to the corresponding N-oxide. Non-limiting-examples of heteroaryls include aromatic ring system comprising 5 or 6 ring atoms and containing one to three heteroatom(s) selected from the group consisting of nitrogen, oxygen and sulfur, such as pyridyl, pyrazinyl, furanyl, thienyl, pyrimidinyl, isoxazolyl, isothiazolyl, oxazolyl, thiazolyl, pyrrolyl, triazolyl, and the like.

The term "heterocyclyl" means a radical of saturated or partially saturated monocyclic or multicyclic ring system comprising about 3 to about 10 ring atoms, preferably about 5 to about 10 ring atoms, in which one or more of the atoms in the ring system is an element other than carbon, for example nitrogen, oxygen-or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include saturated or partially saturated monocyclic ring system comprising 5 or 6 ring atoms and containing one to three heteroatom(s) selected from the group consisting of nitrogen, oxygen and sulfur, such as piperidyl, pyrrolidinyl, piperazinyl, pyranyl, tetrahydrothiophenyl, morpholinyl and the like.

The phrase "a divalent heterocyclic group" means a divalent group derived from non-aromatic saturated or partially saturated monocyclic ring system comprising about 3 to about 10 ring atoms, preferably about 5 to about 6 ring atoms, in which one or more of the atoms in the ring system is an element other than carbon, for example nitrogen, oxygen or sulfur, alone or in combination. The nitrogen or sulfur atom of the heterocyclyl can be optionally oxidized to the corresponding N-oxide, S-oxide or S,S-dioxide. Non-limiting examples of suitable "a divalent heterocyclic group" include a divalent group derived from saturated or partially saturated monocyclic ring system comprising 5 or 6 ring atoms and containing one to three heteroatom(s) selected from the group consisting of nitrogen, oxygen and sulfur, such as piperidine, pyrrolidine, piperazine, pyrane, tetrahydrothiophene, morpholine and the like.

The object compound (I) of the present invention can be prepared by the following processes.

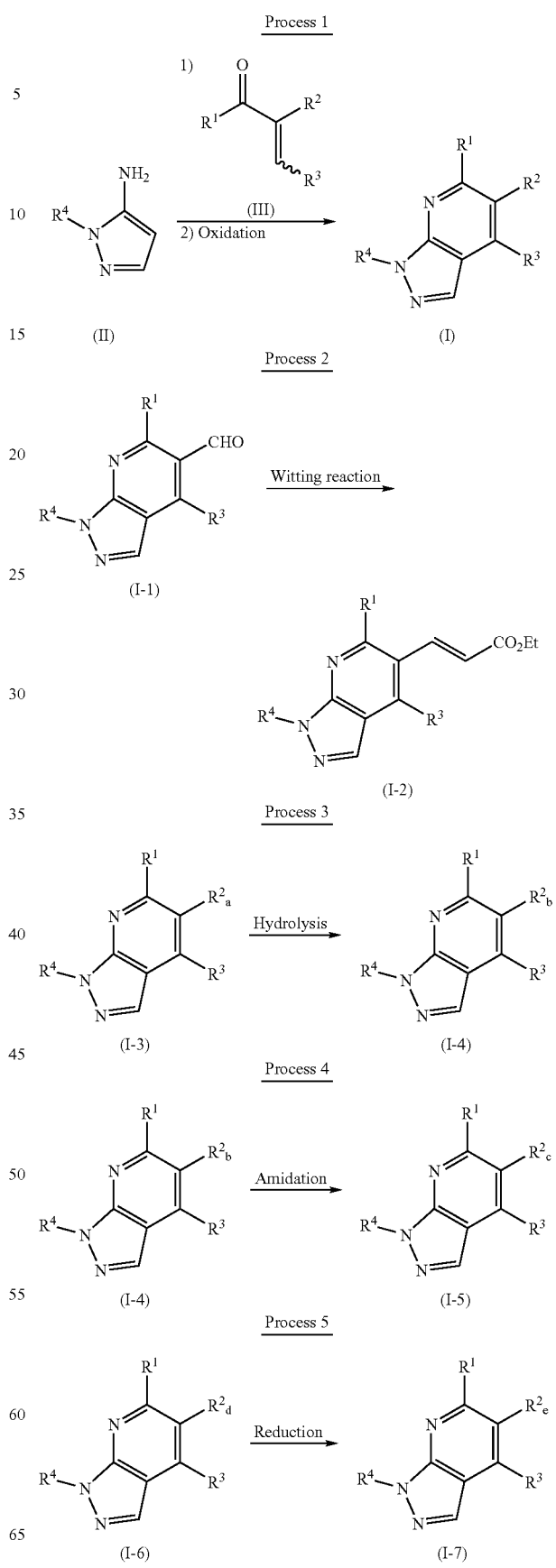

wherein
R¹ R², R³ and R⁴ are each as defined above,
R²$_a$ is the same as above R² having protected carboxy,
R²$_b$ is the same as above R² having carboxy moiety,
R²$_c$ is the same as above R² having CONR⁶R⁷ moiety,
(wherein R⁶ and R⁷ are each as defined above)
R²$_d$ is the same as above R² having —CH=CH— moiety, and
R²$_e$ is the same as R²$_d$ wherein —CH=CH— moiety has changed to alkylene moiety.

The starting compound (II) and (III) of the present invention can be prepared according to a conventional manner or in a similar manner as described in the following Preparations and/or Examples.

The above Processes can be carried out according to a conventional manner such as the one described in Preparations and/or Examples, or in a similar manner thereto.

The compounds of the present invention can be purified by any conventional purification methods employed for purifying organic compounds, such as re-crystallization, column chromatography, thin-layer chromatography, high-performance liquid chromatography and the like. The compounds can be identified by conventional methods such as NMR spectrography, mass spectrography, IR spectrography, elemental analysis, and measurement of melting point.

The new pyrazolopyridine derivatives (I) and pharmaceutically acceptable salts thereof hardly possess a strong inhibitory activity against phosphodiesterase III (PDE III), but possess a strong inhibitory activity against phosphodiesterase IV (PDE IV) and a strong inhibitory activity on the tumor necrosis factor (TNF).

That is, the pyrazolopyridine derivatives (I) and pharmaceutically acceptable salts thereof are selective inhibitors of phosphodiesterase IV (PDE IV) and inhibitors on the production of tumor necrosis factor (TNF).

Accordingly, the new pyrazolopyridine derivatives (I) and a pharmaceutically acceptable salt thereof can be used for prophylactic and therapeutic treatment of PDE-IV and TNF mediated diseases such as chronic inflammatory diseases (e.g., rheumatoid arthritis, osteoarthritis, emphysema, chronic bronchiolitis, allergic rhinitis, etc.), osteoporosis, rejection by transplantation, asthma, chronic obstructive pulmonary disease (COPD), eosinophilia, fibrotic disease (e.g., cystic fibrosis, pulmonary fibrosis, hepatic fibrosis, renal fibrosis, etc.), (viral alcoholic, drug-induced) acute and fulminant hepatitis, hepatic steatosis (alcoholic and non-alcoholic steato-hepatitis), chronic (viral and non-viral) hepatitis, hepatic cirrhosis, autoimmune hepatitis, pancreatitis, nephritis, endotoxin shock, specific autoimmune diseases [e.g., ankylosing spondylitis, autoimmune encephalomyelitis, autoimmune hematological disorders (e.g., hemolytic anemia, aplastic anemia, pure red cell anemia, idiopathic thrombocytopenia, etc.), systemic lupus. erythematosus (SLE), polychondritis, scleroderma, Wegener granulomatosis, dermatomyositis, chronic active hepatitis (Wilson's disease, etc.), myasthenia gravis, idiopathic sprue, autoimmune inflammatory bowel disease (e.g., ulcerative colitis, Crohn's disease, etc.), endocrine ophthalmopathy, Grave's disease, sarcoidosis, multiple sclerosis, primary biliary cirrhosis, juvenile diabetes (diabetes mellitus type I), Reiter's syndrome, non infection uveitis, autoimmune keratitis (e.g., keratoconjunctivitis sicca, vernal keratoconjunctivitis, etc.), interstitial lung fibrosis, psoriatic arthritis, etc.], dermatological disorders associated with PDE-IV enzyme (such as psoriasis and other benign or malignant proliferative skin diseases, atopic dermatitis, and urticaria), neurodegenerative disorders such as Parkinson disease and Alzheimer's disease, acute and chronic multiple sclerosis, cancer cachexia, viral infection, AIDS cachexia, thrombosis, depression, and the like.

For therapeutic administration, the compound (I), or its prodrug, or a salt thereof can be administered alone or in the form of a mixture, preferably, with a pharmaceutical vehicle or carrier.

The active ingredient of this invention can be used in the form of a pharmaceutical preparation, for example, in solid, semisolid or liquid form, which contains a compound (I), as an active ingredient, in admixture with an organic or inorganic carrier or excipient suitable for external (topical), enteral, intravenous, intramuscular, parenteral or intra-mucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce, the desired effect upon the process or condition of the diseases.

The active ingredient can be formulated into, for example, preparations for oral application, preparations for injection, preparations for external application, preparations for inhalation, and preparations for application to mucous membranes.

Further, the compound of this invention can be used in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) Hi (histamine). receptor antagonists, ix) beta 2 adrenoceptor agonist, x) interferon, xi) antiviral drugs for hepatitis C virus (HCV) such as protease inhibitor, helicase inhibitor, polymerase inhibitor, or the like, xii) antiviral drug for hepatitis B virus such as lamivudine, xiii) ursodesoxycholic acid, xiv) glycyrrhizin, xv) human grouth factor (HGF), xvi) aminosalicylic acid such as salazosulfapyridine, mesalazin, or the like, xvii) steroids such as prednisolone farnesylate, xviii) immunosuppressant such as azathioprine, 6-mercaptopurine, tacrolimus, and the like.

Mammals which may be treated by the present invention include livestock mammals such as cows, horses, etc., domestic animals such as dogs, cats, rats, etc. and humans, preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

In order to show the utilities of the pyrazolopyridine derivatives (I) and a pharmaceutically acceptable salt thereof of the present invention, pharmacological test data of the representative compound of the pyrazolopyridine derivatives (I) are illustrated in the following.

(a) Inhibition of U937 Phosphodiesterase IV (PDE IV)

1. Test Method:

Cultured U937 cells were washed twice and harvested with phosphate-buffered saline (PBS) by cell-scraper. After centrifugation, the cell pellet was suspended in homogenizing buffer (0.5% deoxycholate [DOC], 5 mM 2-mercaptoethanol, 1 µM leupeptin, 100 µM PMSF, 20 µM p-tosyl-L-lysine-chloromethyl ketone [TLCK] in PBS). The cell suspension was then sonicated for a couple of minutes and homogenized by a glass-Teflon homogenizer with twenty strokes. The homogenate was centrifuged at 200 g for 30 minutes, and the supernatant was further ultra-centrifuged at 100,000×g for 90 minutes (4° C.). The final supernatant was dialyzed against dialysis buffer, which was the same component as homogenizing buffer without DOC. The dialysate of enzyme preparation was stored at −20° C. until assay.

PDE4, activity was estimated with a Phosphodiesterase [$^3$H]cAMP SPA Enzyme Assay System (Amersham Pharmacia Biotech), using a 96 well Opti-plate. Reactions were initiated by addition of 0.025 µCi/well of [$^3$H]cAMP to the enzyme mixture containing 50 mM Tris-HCl (pH 7.5), 8.3 mM $MgCl_2$, 1.7 mM EGTA, and various concentrations of the test compound or vehicle. CI-930 (10 µM in final), a specific PDE3, inhibitor, was also added in the reaction mixture. After incubation at 30° C. for 15 minutes, 50 µL of SPA beads suspension was added to each well. The well-plate was then shaken for 20 minutes by a plate mixer. Radio-activity in each well was counted by a Top Counter.

Test compounds were dissolved in 100% dimethylsulfoxide (DMSO) and diluted into respective concentrations with the final solution containing 1% v/v of DMSO.

$IC_{50}$ values of test compounds for the enzyme activity of PDE4 was determined from regression analysis for log-logit conversion values of percent inhibition in the compound-treated tubes compared to that of the control. Percent inhibition was calculated with the following equation: Inhibition (%)={1−(C−B)/(A−B)}×100; in which A, B and C means mean values of radio-activity counts (dpm) of control, blank and the compound-treated tubes, respectively.

2. Test Results

The following table illustrates the inhibitory activity on PDE-IV of the representative compound of formula (I):

| Example | Compound name | $IC_{50}$ (µM) |
|---|---|---|
| 73 | 4-(5-bromo-3-pyridyl)-1-ethyl-6-methyl-1H-pyrazolo[3,4-b]pyridine-5-carbonitrile | <1 |
| 84 | (2E)-3-[4-(5-bromo-3-pyridyl)-1-ethyl-6-methyl-1H-pyrazolo[3,4-b]pyridin-5-yl]acrylic acid | <1 |
| 89 | (2E)-3-[6-[(Cyclohexylmethoxy)methyl]-1-ethyl-4-(5-methyl-3-pyridyl)-1H-pyrazolo[3,4-b]pyridin-5-yl]acrylic acid | <1 |
| 91 | (2E)-3-[1-Ethyl-4-(5-methyl-3-pyridyl)-6-phenyl-1H-pyrazolo[3,4-b]pyridin-5-yl]acrylic acid | <1 |

(b) Inhibition on TNF-alpha Production in Rat Mononuclear Cells

1. Test Method (1) Rat Peripheral Blood Mononuclear Cells (PBMC) Preparation

Male Wistar rat at the age of 15 weeks was anesthetized with ether and the blood (about 15 ml) was collected with a disposable syringe from the abdominal artery under celiotomy. Collected blood was transferred to a heparin containing polyethylene tube and an equal volume of RPMI1640 was added to each tube. Diluted blood was then piled tip to 20 ml of Lympholyte-Rat (Cedarlane Laboratories, Canada) in polystyrene centrifuge tube. After centrifugation at 3,000 rpm for 30 minutes, cells gathering in the center area of the gradient were collected by capillary and washed with 40 mL of RPMI1640 by twice of centrifugation at 1,200 rpm for 10 minutes. Precipitate was then suspended in 10 ml of Tris-ammonium-chloride buffer and stood for 10 minutes in order to lyse remaining erythrocytes. After centrifugation at 1,200 rpm for 10 minutes, the precipitate was washed twice with 50 ml of RPMI1640 by centrifugation. PBMC finally precipitated were suspended in RPMI1640 containing 1% fetal bovine serum and antibiotics. After cell counting, final suspension at $3 \times 10^6$ cells/mL in culture medium was prepared.

(2) TNF-alpha Production from Stimulated PBMCs

Rat PBMC prepared by the density gradient method using Lympholyte-Rat, were suspended in the culture medium mentioned above with the concentration of $3 \times 10^6$ cells/mL and 0.5 ml of the suspension was sowed into each well of a 24-well culture plate. Cells were incubated in the $CO_2$ incubator for 24 hours with 0.25 ml of LPS in addition of 0.25 ml of concentrations of drugs or vehicle at the start of the incubation. Final concentration of LPS in the incubation medium was 1 µg/mL. After 24 hours, the supernatant of each well by centrifugation at 1,700 rpm for 10 minutes was stored at −80° C. until assay. TNF-alpha levels in the medium were measured by ELISA.

The $IC_{50}$ values of drugs on cytokine productions in LPS stimulated PBMC were estimated by the regression analysis for the relative values of cytokine level in the drug-treated wells compared to those of the vehicle-treated ones.

2. Test Results

The following table illustrates the inhibitory activity on TNF-alpha production in rat of the representative compound of formula (I):

| Example | Compound name | $IC_{50}$ (nM) |
|---|---|---|
| 73 | 4-(5-bromo-3-pyridyl)-1-ethyl-6-methyl-1H-pyrazolo[3,4-b]pyridine-5-carbonitrile | 27.0 |
| 84 | (2E)-3-[4-(5-bromo-3-pyridyl)-1-ethyl-6-methyl-1H-pyrazolo[3,4-b]pyridin-5-yl]acrylic acid | 62.7 |
| 89 | (2E)-3-[6-[(Cyclohexylmethoxy)methyl]-1-ethyl-4-(5-methyl-3-pyridyl)-1H-pyrazolo[3,4-b]pyridin-5-yl]acrylic acid | 85.6 |
| 91 | (2E)-3-[1-Ethyl-4-(5-methyl-3-pyridyl)-6-phenyl-1H-pyrazolo[3,4-b]pyridin-5-yl]acrylic acid | 15.7 |

BEST MODE FOR CARRYING OUT THE INVENTION

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

The starting materials and intermediates are prepared by the application or adaptation of known methods, for example methods as described in the Reference Examples or their obvious chemical equivalents.

The abbreviations, symbols and terms used in the Preparations, Examples and Formulae have the following meanings.

AcOH Acetic acid
BuOH Butanol
CHCl$_3$ Chloroform
DCM Dichloromethane
DDQ 2,3-Dichloro-5,6-dicyano-p-benzoquinone
DMF N,N-dimethylformamide
Et$_3$N Triethylamine
EtOAc or AcOEt Ethyl acetate
EtOH Ethanol
HCl Hydrochloric acid
MeOH Methanol
MgSO$_4$ Magnesium sulfate
NaHCO$_3$ Sodium hydrogencarbonate
NaOH Sodium hydroxide
Pd/C Palladium on carbon powder
THF Tetrahydrofuran Preparation 1

A mixture of 3-chlorobenzaldehyde (2 g), ethyl acetoacetate (1.94 g), AcOH (0.23 ml), piperidine (0.23 ml) in cyclohexane (40 ml) was refluxed azeotropically for 2 hours. After cooling, the reaction mixture was diluted with EtOAc. The organic layer was washed with water, saturated aqueous NaHCO$_3$, brine, dried over anhydrous MgSO$_4$ and concentrated in vacuo to give ethyl 2-acetyl-3-(3-chlorophenyl)acrylate (4.19 g) as a yellow oil.

$^1$H-NMR (CDCl$_3$) δ 1.29 (1.2H, t, J=7 Hz), 1.36 (1.8H, t, J=7 Hz), 2.36 (1.2H, s), 2.44 (1.8H, s), 4.33 (0.8H, q, J=7 Hz), 4.34 (1.2H, q, J=7 Hz), 7.46-7.55 (2H, m), 7.61-7.74 (3H, m)

The following compound(s) was(were) obtained in a similar manner to that of Preparation 1.

Preparation 2 tert-Butyl 2-(methoxyacetyl)-3-(5-methyl-3-pyridyl)acrylate $^1$H-NMR (CDCl$_3$) δ 1.51 (4.5H, s), 1.54 (4.5H, s), 2.33 (1.5H, s), 2.36 (1.5, s), 3.42 (1.5H, s), 3.45 (1.5H, s), 4.17 (1H, s), 4.39 (1H, s), 7.49-7.64 (2H, m), 8.43-8.51 (2H, m)

Preparation 3

Ethyl (2Z)-2-acetyl-3-(2-chloro-4-pyridyl)acrylate $^1$H-NMR (CDCl$_3$) δ 1.36 (3H, t, J=7 Hz), 2.37 (3H, s), 4.34 (2H, q, J=7 Hz), 7.17 (1H, d, J=7 Hz), 7.29 (1H, s), 7.50 (1H, s), 8.40 (1H, d, J=7 Hz)
MS (ESI$^+$) m/z 254 (M+1)

Ethyl (2E)-2-acetyl-3-(2-chloro-4-pyridyl)acrylate $^1$H-NMR (CDCl$_3$) δ 1.28 (3H, t, J=7 Hz), 2.44 (3H, s), 4.33 (2H, q, J=7 Hz), 7.22 (1H, dd, J=7.1 Hz), 7.34 (1H, s), 7.44 (1H, s), 8.44 (1H, d, J=7 Hz)
MS (ESI$^+$) m/z 254 (M+1)

Preparation 4 tert-Butyl (2Z)-3-(5-bromo-3-pyridyl)-2-(methoxyacetyl)acrylate $^1$H-NMR (CDCl$_3$): δ 1.55 (9H, s), 3.42 (3H, s), 4.17 (2H, s), 7.57 (1H, s), 7.87 (1H, t, J=1 Hz), 8.54 (1H, d, J=1 Hz), 8.65 (1H, d, J=1 Hz)
MS (ESI$^+$) m/z 358 (M+2), 356 (M)

tert-Butyl (2E)-3-(5-bromo-3-pyridyl)-2-(methoxyacetyl)acrylate $^1$H-NMR (CDCl$_3$) δ 1.51 (9H, s), 3.44 (3H, s), 4.37 (2H, s), 7.57 (1H, s), 7.98 (1H, t, J=1 Hz), 8.58 (1H, d, J=1 Hz), 8.69 (1H, d, J=1 Hz)
MS (ESI$^+$) m/z 358 (M+2), 356 (M)

Preparation 5

Ethyl 2-acetyl-3-(5-bromo-3-pyridyl)acrylate $^1$H-NMR (CDCl$_3$) δ 1.28 (1.5H, t, J=7 Hz), 1.35 (1.5H, t, J=7 Hz), 3.40 (1.5H, s), 3.43 (1.5H, s), 4.19 (1H, s), 4.32 (1H, q, J=7 Hz), 4.33 (1H, q, J=7 Hz), 4.34 (1H, s), 7.65 (0.5H, s), 7.68 (0.5H, s), 7.89 (0.5H, t, J=1 Hz), 7.94 (0.5H, t, J=1 Hz), 8.55 (0.5H, d, J=1 Hz), 8.58 (0.5H, d, J=1 Hz), 8.67 (0.5H, d, J=1 Hz), 8.69 (1H, d, J=1 Hz)
MS (ESI$^+$) m/z 330 (M+2), 328 (M)

Preparation 6

Ethyl 2-acetyl-3-(5-methyl-3-pyridyl)acrylate $^1$H-NMR (CDCl$_3$) δ 1.29 (2H, t, J=7 Hz), 1.35 (1H, t, J=7 Hz), 2.36 (3H, s), 2.39 (1H, s), 2.45 (2H, s), 4.34 (2H, q, J=7 Hz), 7.50 (1H, s), 7.57 (0.67H, s), 7.61 (0.33H, s), 8.44 (1H, s), 8.47 (0.33H, s), 8.50 (0.67H, s)
MS (ESI$^+$) m/z 234 (M+1)

Preparation 7

Ethyl 3-(5-bromo-3-pyridyl)-2-(methoxyacetyl)acrylate $^1$H-NMR (CDCl$_3$) δ 1.28 (1.5H, t, J=7 Hz), 1.35 (1.5H, t, J=7 Hz), 3.40 (1.5H, s), 3.43 (1.5H, s), 4.19 (1H, s), 4.32 (1H, q, J=7Hz), 4.33 (1H, q, J=7 Hz), 4.34 (1H, s), 7.65 (0.5H, s), 7.67 (0.5H, s), 7.89 (0.5H, t, J=1 Hz), 7.94 (0.5H, t, J=1 Hz), 8.55 (0.5H, d, J=1 Hz), 8.58 (0.5H, d, J=1 Hz), 8.67 (0.5H, d, J=1 Hz), 8.69 (1H, d, J=1 Hz)
MS (ESI$^+$) m/z 330 (M+2), 328 (M)

Preparation 8 tert-Butyl 2-[(cyclopropylmethoxy)acetyl]-3-(5-methyl-3-pyridyl)acrylate $^1$H-NMR (CDCl$_3$) δ 0.19-0.25 (2H, m), 0.50-0.59 (2H, m), 1.07-1.13 (1H, m), 1.51 (4.5H, s), 1.54 (4.5H, s), 2.34 (1.5H, s), 2.35 (1.5H, s), 3.34 (1H, d, J=7 Hz), 3.39 (1H, d, J=7 Hz), 4.24 (1H, s), 4.47 (1H, s), 7.53 (0.5H, s), 7.63 (1H, s), 7.65 (1H, s), 8.44 (1H, s), 8.45 (0.5H, s), 8.55 (0.5H, s)
MS (ESI$^+$) m/z 331 (M+1)

Preparation 9 tert-Butyl 3-(5-bromo-3-pyridyl)-2-[(cyclopropylmethoxy)acetyl]acrylate

¹H-NMR (CDCl₃) δ 0.15-0.30 (2H, m), 0.50-0.62 (2H, m), 1.07-1.15 (1H, m), 1.53 (9H, s), 3.28-3.40 (2H, d, J=7 Hz), 4.30 (2H, s), 7.8-7.91 (2H, m), 8.53-8.60 (2H, m)
MS (ESI⁺) m/z 398 (M+2), 396 (M)

Preparation 10 tert-Butyl 2-[(cyclohexylmethoxy)acetyl]-3-(5-methyl-3-pyridyl)acrylate

¹H-NMR (CDCl₃) δ 0.90-0.95 (2H, m), 1.15-1.20 (3H, m), 1.50 (4.5H, s), 1.52 (4.5H, s), 1.63-1.76 (6H, m), 2.34 (1.5H), 2.35 (1.5H, s), 3.25 (1H, d, J=7 Hz), 3.33 (1H, d, J=7 Hz), 4.19 (1H, s), 4.41 (1H, s), 7.49-7.51 (1H, m), 7.60-7.61 (1H, m), 8.41-8.44 (1H, m), 8.49-8.51 (1H, m)
MS (ESI⁺) m/z 374 (M+¹)

Preparation 11

Ethyl 2-(cyclohexylcarbonyl)-3-(5-methyl-3-pyridyl)acrylate

¹H-NMR (CDCl₃) δ 1.10-1.30 (4H, m), 1.27 (1.5H, t, J=7 Hz), 1.34 (1.5H, t, J=7 Hz), 1.64-1.89 (6H, m), 2.34 (1.5H, s), 2.35 (1.5H, s), 2.83-2.93 (1H, m), 4.31 (1H, q, J=7 Hz), 4.33 (1H, q, J=7 Hz), 7.50 (0.5H, s), 7.53 (0.5H, s), 7.57 (0.5H, s), 7.69 (0.5H, s), 8.44 (1H, s), 8.45 (0.5H, s), 8.49 (0.5H, s)
MS (ESI⁺) (m/z) 302 (M+1)

Preparation 12

Ethyl 2-({[tert-butyl(diphenyl)silyl]oxy}acetyl)-3-(5-methyl-3-pyridyl)acrylate

¹H-NMR (CDCl₃) δ 1.00 (9H, s), 1.24 (3H, t, J=7 Hz), 2.40 (3H, s), 4.28 (2H, q, J=7 Hz), 4.35 (2H, s), 7.28-7.32 (6H, m), 7.50-7.55 (4H, m), 7.75 (1H, s), 8.53 (1H, s), 8.55 (1H, s)
MS (ESI⁺) m/z 488 (M+1)

Preparation 13

Ethyl 2-acetyl-3-(4-chlorophenyl)acrylate

¹H-NMR (CDCl₃) δ 1.25-1.38 (3H, m), 2.36 (1H, s), 2.42 (2H, s), 4.26-4.39 (2H, m), 7.32-7.44 (4H, m), 7.52 (0.67H, s), 7.61 (0.33H, s).

Preparation 14

Ethyl 2-acetyl-3-(2-chlorophenyl)acrylate

¹H-NMR (CDCl₃) δ 1.18 (1.8H, t, J=8 Hz), 1.35 (1.2H, t, J=8 Hz), 2.24 (1.2H, s), 2.47 (1.8H, s), 4.24 (1.2H, q, J=8 Hz), 4.32 (0.8H, q, J=8 Hz), 7.20-7.38 (2H, m), 7.45 (2H, d, J=8 Hz), 7.88 (0.6H, s), 7.96 (0.4H, s)

Preparation 15

A mixture of 5-amino-1-ethylpyrazole (250 mg) and ethyl 2-acetyl-3-(3-chlorophenyl)acrylate (568 mg) was heated at 130° C. for 3 hours. After cooling, the residue was evaporated. The residue was diluted with CHCl₃ and washed with saturated NaHCO₃, water, dried over anhydrous MgSO₄ and concentrated in vacuo. The residue was purified by flash column chromatography on silica gel eluting with a mixture of EtOAc and n-hexane (1:7)-to give ethyl 4-(3-chlorophenyl)-1-ethyl-6-methyl-4,7-dihydro-1H-pyrazolo[3,4-b]pyridine-5-carboxylate (271 mg) as a yellow oil.
¹H-NMR (CDCl₃) δ 1.10 (3H, t, J=7 Hz), 1.49 (3H, t, J=7 Hz), 2.74 (3H, s), 3.05-3.13 (2H, m), 4.15 (2H, q, J=7 Hz), 4.59 (2H, q, J=7 Hz), 7.37-7.50 (4H, m), 7.85 (1H, s)

Preparation 16

A mixture of 5-methylnicotinaldehyde (400 mg), ethyl benzoylacetate (635 mg), AcOH (0.15 ml), piperidine (0.15 ml) in EtOH (5 ml) was stirred at room temperature for 24 hours. After evaporation, the residue was diluted with saturated aqueous NaHCO₃ and extracted with EtOAc. The organic layer was washed with brine, dried over anhydrous MgSO₄ and concentrated in vacuo to give ethyl (2Z)-2-benzoyl-3-(5-methyl-3-pyridyl)acrylate (986 mg) as a yellow oil.
¹H-NMR (CDCl₃) δ 1.19 (3H, t, J=7 Hz), 2.20 (3H, s), 4.25 (2H, q, J=7 Hz), 7.41-7.48 (3H, m), 7.58 (1H, t, J=7 Hz), 7.90 (2H, s), 7.93 (1H, d, J=7 Hz), 8.32 (1H, s), 8.42 (1H, s)
MS (ESI⁺) 296 (M+1)

The following compound(s) was(were) obtained in a similar manner to that of Preparation 16.

Preparation 17

Ethyl (2Z)-3-(5-methyl-3-pyridyl)-2-(2-thienylcarbonyl)acrylate

¹H-NMR (CDCl₃) δ 1.27 (3H, t, J=7 Hz), 2.24 (3H, s), 4.29 (2H, q, J=7 Hz), 7.05-7.07 (1H, m), 7.50 (1H, s), 7.56 (1H, d, J=3 Hz), 7.89 (1H, s), 8.34 (1H, s), 8.47 (1H, s)
MS (ESI⁺) m/z 302 (M+1)

Preparation 18

Ethyl 2-(4-methoxybenzoyl)-3-(5-methyl-3-pyridyl)acrylate

¹H-NMR (CDCl₃) δ 1.21 (3H, t, J=7 Hz), 2.20 (3H, s), 3.85 (3H, s), 4.25 (2H, q, J=7 Hz), 6.90 (2H, d, J=8 Hz), 7.43 (1H, s), 7.85 (1H, s), 7.90 (2H, d, J=8 Hz), 8.30 (1H, s), 8.41 (1H, s)

Preparation 19

To a solution of methyl 3-cyclopropyl-3-oxopropanoate (3.00 g) and cyclohexanecarboxaldehyde (2.84 g) in MeOH (30 ml) was added piperidine (0.209 ml) at room temperature. The mixture was stirred for 48 h. The solvent was evaporated off, and the residue was chromatographed on a silicagel column chromatography (EtOAc-hexaens, a linear gradient of EtOAc from 0 to 15% over 60 min) afforded methyl 3-cyclohexyl-2-(cyclopropylcarbonyl)acrylate as a colorless oil (3.72 g).
¹H-NMR (CDCl₃) δ 0.98 (2H, m), 1.12-1.33 (6H, m), 1.68-13.77 (5H, m), 2.08-2.24 (1H, m), 2.27-2.49 (1H, m), 3.78 and 3.84 (3H, s), 6.71 and 6.71 (1H, d, J=10.2 and 10.6 Hz, respectively)

Preparation 20

To a stirred solution of 5-bromonicotinaldehyde (1 g) and ethynyltrimethylsilane (792 mg) in Et₃N (15 ml) was added tetrakis(triphenylphosphine)palladium (124 mg) and copper (I) iodide (51 mg). After 4 hours, the resulting mixture was filtrated and evaporated. The residue was dissolved in EtOAc and washed successively with dil. NH₃aq, water and brine. The organic layer was dried over MgSO₄ and evaporated. The residue was purified with silica gel column chromatography to give 5-[(trimethylsilyl)ethynyl]nicotinaldehyde as a slightly yellow oil.

¹H-NMR (CDCl₃) δ 0.28 (9H, s), 8.20 (1H, s), 8.88 (1H, s), 8.97 (1H, s), 10.09 (1H, s)

Preparation 21

A mixture of 6-chloronicotinaldehyde (1 g), ethyl 3-oxo-3-phenylpropanoate (1.36 g), AcOH (0.04 ml), piperidine (0.028 ml) in benzene (15 ml) was refluxed for 1.5 hours. After cooling, the reaction mixture was diluted with saturated aqueous NaHCO₃ and extracted with EtOAc. The organic layer was washed with brine, dried over anhydrous MgSO₄ and concentrated in vacuo. The residue was purified by flash column chromatography on silica gel eluting with a mixture of EtOAc and n-hexane (1:2) to give ethyl (2Z)-2-benzoyl-3-(6-chloro-3-pyridyl)acrylate (2.018 g) as a yellow oil.

¹H-NMR (CDCl₃) δ 1.19 (3H, t, J=7 Hz), 4.24 (2H, q, J=7 Hz), 7.18 (1H, d, J=7 Hz), 7.45 (2H, t, J=7 Hz), 7.59 (2H, t, J=7 Hz), 7.88 (1H, s), 7.93 (2H, d, J=7 Hz), 8.44 (1H, d, J=4 Hz)

The following compound(s) was(were) obtained in a similar manner to that of Preparation 21.

Preparation 22

Ethyl 3-(5-methyl-3-pyridyl)-2-pentanoylacrylate

¹H-NMR (CDCl₃) δ 0.88 (3H, t, J=7 Hz), 1.25-1.44 (5H, m), 2.33 (3H, s), 2.58 (2H, t, J=7 Hz), 4.32 (2H, q, J=7 Hz), 7.48 (1H, s), 7.62 (1H, s), 8.44 (2H, s)

Preparation 23

Ethyl 2-[(5-methyl-3-isoxazolyl)carbonyl]-3-(5-methyl-3-pyridyl)acrylate

Major Isomer

¹H-NMR (CDCl₃) δ 1.24 (3H, t, J=7 Hz), 2.28 (3H, s), 2.45 (3H, s), 4.26 (2H, q, J=7 Hz), 6.50 (1H, s), 7.99 (1H, s), 8.70 (1H, s), 8.90 (1H, s)

Minor Isomer

¹H-NMR (CDCl₃) δ 1.27 (3H, t, J=7 Hz), 2.49 (3H, s), 2.54 (3H, s), 4.36 (2H, q, J=7 Hz), 6.48 (1H, s), 7.45 (1H, s), 7.90 (1H, s), 8.16 (1H, s)

Preparation 24

Methyl 3-(4-amino-3,5-dichlorophenyl)-2-(cyclopropylcarbonyl)acrylate

¹H-NMR (CDCl₃) δ 1.00 and 1.06 (2H, m), 1.20 and 1.28 (2H, m), 2.11 and 2.23 (1H, m), 3.82 and 3.89 (3H, s), 4.79 and 4.83 (2H, br s), 7.32 and 7.34 (2H, s), 7.45 and 7.50 (1H, s)

Preparation 25

Ethyl 2-isobutyryl-3-(2-methyl-4-pyridyl)acrylate

¹H-NMR (CDCl₃) δ 1.06 (3H, d, J=7 Hz), 1.19 (3H, d, J=7 Hz), 1.25 (1.5H, t, J=7 Hz), 1.33 (1.5H, t, J=7 Hz), 2.56 (1.5H, s), 2.57 (1.5H, s), 2.65 (0.5H, sep, J=7 Hz), 3.15 (0.5H, sep, J=7 Hz), 4.29 (1H, q, J=7 Hz), 4.30 (1H, q, J=7 Hz), 7.03-7.15 (2H, m), 7.48 (0.5H, s), 7.65 (0.5H, s), 8.50-8.55 (1H, m)

MS (ESI⁺) m/z 262 (M+1)

Preparation 26

Ethyl 2-isobutyryl-3-{5-[(trimethylsilyl)ethynyl]-3-pyridyl}acrylate

¹H-NMR (CDCl₃) δ 0.01 (9H, s), 0.83 (6H, d, J=7 Hz), 1.06 (3H, t, J=7 Hz), 2.46 (1H, h, J=7 Hz), 4.07 (2H, q, J=7 Hz), 7.00 (1H, s), 7.40 (1H, s), 8.39 (2H, s)

Preparation 27

Ethyl 3-(2-chloro-4-pyridyl)-2-(cyclopentylcarbonyl)acrylate

¹H-NMR (CDCl₃) δ 1.27 (1.5H, t, J=7 Hz), 1.34 (1.5H, t, J=7 Hz), 1.52-1.77 (6H, m), 1.84-1.93 (2H, m), 2.83 (1H, quintet, J=7 Hz), 3.35 (1H, quintet, J=7 Hz), 4.30 (1H, q, J=7 Hz), 4.32 (1H, q, J=7 Hz), 7.17-7.23 (1H, m), 7.29 (0.5H, s), 7.35 (0.5H, s), 7.45 (0.5H, s), 7.57 (0.5H, s), 8.39-8.44 (1H, m)

MS (ESI⁺) m/z 308 (M+1)

Preparation 28

Ethyl (2Z)-2-(4-methoxybenzoyl)-3-(5-methyl-3-pyridyl)acrylate

¹H-NMR (CDCl₃) δ 1.21 (3H, t, J=7 Hz), 2.20 (3H, s), 3.85 (3H, s), 4.25 (2H, q, J=7 Hz), 6.90 (2H, d, J=8 Hz), 7.43 (1H, s), 7.85 (1H, s), 7.90 (2H, d, J=8 Hz), 8.30 (1H, s), 8.41 (1H, s)

Preparation 29

Ethyl 2-acetyl-3-(5-chloro-2-thienyl)acrylate

¹H-NMR (CDCl₃) δ 1.35 (1.2H, t, J=8 Hz), 1.40 (1.8H, t, J=8 Hz), 2.40 (1.8H, s), 2.50 (1.2H, s), 4.31 (0.8H, q, J=8 Hz), 4.43 (1.2H, q, J=8 Hz), 6.95 (0.4H, d, J=5 Hz), 7.20-7.25 (1.6H, m), 7.62 (0.6H, s), 7.71 (0.4H, s)

Preparation 30

Ethyl (2Z)-2-benzoyl-3-(5-bromo-3-pyridyl)acrylate

¹H-NMR (CDCl₃) δ 1.17 (3H, t, J=6.7 Hz), 4.25 (2H, q, J=6.7 Hz), 7.42-7.50 (2H, m), 7.56-7.63 (1H, m), 7.77 (1H, s), 7.83 (1H, s), 7.90 (1H, s), 7.92 (1H, s), 8.50 (1H, s), 8.53 (1H, s)

Preparation 31

Ethyl 2-benzoyl-3-cyclohexylacrylate

¹H-NMR (CDCl₃) δ 1.12 (3H, t, J=6.8 Hz), 1.35-1.48 (2H, m), 1.80-2.06 (8H, m), 3.23-3.32 (1H, m), 4.16 (2H, q, J=6.8 Hz), 6.96 (1H, d, J=8.5 Hz), 7.45-7.52 (3H, m), 7.58-7.66 (2H, m)

Preparation 32

Ethyl 2-benzoyl-3-(3-pyridyl)acrylate

¹H-NMR (CDCl₃) δ 1.19 (3H, t, J=8 Hz), 4.25 (2H, q, J=8 Hz), 7.16 (1H, m), 7.41-7.50 (2H, m), 7.55-7.66 (2H, m), 7.90-7.97 (2H, m), 8.50 (1H, dd, J=6, 2 Hz), 8.62(1H, d, J=2Hz)

Preparation 33

Ethyl 2-benzoyl-3-(2-chloro-4-pyridyl)acrylate $^1$H-NMR (CDCl$_3$) δ 1.21 (3H, t, J=8 Hz), 4.27 (2H, q, J=8 Hz), 7.10 (1H, br d, J=5 Hz), 7.40-7.55 (3H, m), 7.62 (1H, br t, J=7 Hz), 7.79 (1H, s), 7.83-7.94-(2H, m), 8.27 (1H, d, J=7 Hz)

Preparation 34

Ethyl 2-benzoyl-4-cyclohexyl-2-butenoate $^1$H-NMR (CDCl$_3$) δ 0.54-1.00 (5H, m), 1.07 (1.5H, t, J=7 Hz), 1.19 (1.5H, t, J=7 Hz), 1.38-1.60 (6H, m), 3.20-3.30 (2H, m), 4.00-4.19 (2H, m), 4.81-4.97 (1H, m), 7.45-7.60 (3H, m), 7.97-8.13 (2H, m)

Preparation 35

Ethyl 2-(2-fluorobenzoyl)-3-(5-methyl-3-pyridyl) acrylate $^1$H-NMR (CDCl$_3$) δ 1.20 (3H, t, J=6.8 Hz), 2.25 (3H, s), 4.26 (2H, q, J=6.8 Hz), 7.09 (1H, dd, J=7.7, 8.0 Hz), 7.23-7.29 (1H, m), 7.51-7.59 (2H, m), 7.78 (1H, s), 7.97 (1H, dd, J=7.7, 7.9 Hz), 8.33 (1H, s), 8.40 (1H, s)

Preparation 36

Ethyl 2-benzoyl-3-(5-chloro-2-thienyl)acrylate $^1$H-NMR (CDCl$_3$) δ 1.13 (3H, t, J=8 Hz), 4.19 (2H, q, J=8 Hz), 6.83 (1H, d, J=5 Hz), 7.09 (1H, d, J=5 Hz), 7.44-7.52 (3H, m), 7.62 (1H, br t, J=8 Hz), 7.89 (1H, s), 7.93-7.99 (2H, m).

Preparation 37

Ethyl 2-isobutyryl-3-(5-methyl-3-pyridyl)acrylate $^1$H-NMR (CDCl$_3$) δ 1.09 (4H, d, J=7 Hz), 1.20 (2H, t, J=7 Hz), 1.29 (2H, t, J=7 Hz), 1.33 (1H, t, J=7 Hz), 2.34 (2H, s), 2.36 (1H, s), 2.68-2.78 (2/3H, m), 3.14-3.23 (1/3H, m), 4.31 (4/3H, q, J=7 Hz), 4.34 (2/3H, q, J=7 Hz), 7.49-7.71 (2H, m), 8.44-8.50 (2H, m)

Preparation 38

Ethyl (2Z)-2-benzoyl-3-(5-chloro-3-pyridyl)acrylate $^1$H-NMR (CDCl$_3$) δ 1.19 (3H, t, J=7 Hz), 4.25 (2H, q, J=7 Hz), 7.47 (2H, t, J=7 Hz), 7.57-7.63 (2H, m), 7.86 (1H, s), 7.93 (2H, d, J=7 Hz), 8.47 (2H, dd, J=7, 1 Hz)

Preparation 39

Ethyl 2-benzoyl-3-phenylacrylate $^1$H-NMR (CDCl$_3$) δ 1.18 (3H, t, J=8 Hz), 4.23 (2H, q, J=8 Hz), 7.20-7.60 (8H, m), 7.91-7.99 (3H, m)

Preparation 40

Ethyl (2Z)-2-benzoyl-3-(5-methoxy-3-pyridyl)acrylate $^1$H-NMR (CDCl$_3$) δ 1.19 (3H, t, J=7 Hz), 3.63 (3H, s), 4.25 (2H; q, J=7 Hz), 7.19 (1H, s), 7.47 (2H, t, J=7.5 Hz), 7.57-7.60 (1H, m), 7.93-7.98 (3H, m), 8.20 (1H, d, J=1 Hz), 8.24 (1H, s). MS (ESI$^+$) m/z 312 (M+1)

Preparation 41

Ethyl 2-(3-methylbutanoyl)-3-(5-methyl-3-pyridyl) acrylate $^1$H-NMR (CDCl$_3$) δ 0.93 (3H, d, J=7 Hz), 0.99 (3H, d, J=7 Hz), 1.29 (1.5H, t, J=7 H), 1.33 (1.5H, t, J=7 Hz), 2.18-2.30 (1H, m), 2.34 (1.5H, s), 2.38 (1.5H, s), 2.47 (1H, d, J=7 Hz), 2.60 (1H, d, J=7 Hz), 4.31 (1H, q, J=7 Hz), 4.35 (1H, q, J=7 Hz), 7.51-7.64 (2H, m), 8.45-8.50 (2H, m)

Preparation 42

Ethyl 2-(cyclopropylacetyl)-3-(5-methyl-3-pyridyl) acrylate $^1$H-NMR (CDCl$_3$) δ 0.03-0.07 (1H, m), 0.15-0.21 (1H, m), 0.50-0.56 (1H, m), 0.58-0.64 (1H, m), 0.97-1.13 (1H, m), 1.28 (1.5H, t, J=7 Hz), 1.34 (1.5H, t, J=7 Hz), 2.34 (1.5H, s), 2.35 (1.5H, s), 2.50 (1H, d, J=7 Hz), 2.66 (1H, d, J=7 Hz), 4.30 (1H, q, J=7 Hz), 4.33 (1H, q, J=7 Hz), 7.53-7.65 (2H, m), 8.43-8.49 (2H, m)

Preparation 43

Ethyl 3-(5-chloro-2-thienyl)-2-isobutyrylacrylate $^1$H-NMR (CDCl$_3$) δ 1.15 (3H, d, J=7 Hz), 1.18 (3H, d, J=7 Hz), 1.34 (1.5H, s), 1.40 (1.5H, s), 3.04-3.18 (1H, m), 4.29 (1H, q, J=7 Hz), 4.42 (1H, q, J=7 Hz), 6.90 (0.5H, d, J=3 Hz), 6.93 (0.5H, d, J=3 Hz), 7.15 (0.5H, d, J=3 Hz), 7.21 (0.5H, d, J=3 Hz)

Preparation 44

Ethyl 3-(5-bromo-3-pyridyl)-2-isobutyrylacrylate $^1$H-NMR (CDCl$_3$) δ 1.08 (1.8H, d, J=8 Hz), 1.18 (1.2H, d, J=8 Hz), 1.25-1.38 (3H, m), 2.75 (0.6H, m), 3.15 (0.4H, m), 4.21-4.40 (2H, m), 7.49 (0.4H, s), 7.65 (0.6H, s), 7.84 (0.6H, br s), 7.91 (0.4H, br s), 8.04 (0.6H, br s), 8.56 (0.4H, br s), 8.67 (1H, m).

Preparation 45

Ethyl 3-(5-bromo-3-pyridyl)-2-(cyclopentylcarbonyl)acrylate $^1$H-NMR (CDCl$_3$) δ 1.30 (3H, t, J=7 Hz), 1.44-1.96 (8H, m), 3.00 (1H, tt, J=7,7 Hz), 4.32 (2H, q, J=7 Hz), 7.50 (1H, s), 7.84 (1H, t, J=2 Hz), 8.55 (1H, t, J=2 Hz), 8.92 (1H, s)

Preparation 46

Methyl 3-(2-chloro-4-pyridyl)-2-(cyclopropylcarbonyl)acrylate $^1$H-NMR (CDCl$_3$) δ 1.05-1.12 (4H, m), 2.04-2.11 (1H, m), 3.89 (3H, s), 7.21 (1H, d, J=5.4 Hz), 7.58 (1H, s), 8.41 (1H, d, J=5.4 Hz)

Preparation 47

Methyl 3-(3-chlorophenyl)-2-(methoxyacetyl)acrylate $^1$H-NMR (CDCl$_3$) δ 3.40 (1.8H, s), 3.43 (1.2H, s), 3.83 (1.2H, s), 3.85 (1.6H, s), 4.16 (1.6H, s), 4.35 (1.2H, s), 7.24-7.45 (4H, m), 7.70 (0.4H, s), 7.74 (0.6H, s).

Preparation 48

Methyl 2-(cyclopropylcarbonyl)-3-(5-methyl-3-pyridyl)acrylate

¹H-NMR (CDCl₃) δ 1.01-1.07 (2H, m), 2.22-2.29 (2H, m), 2.04-2.12 (0.5H, m), 2.25-2.32 (0.5H, m), 2.34 (1.5H, s), 2.37 (1.5H, s), 3.86 (3H, s), 7.55-7.70 (2H, m), 8.43-8.51 (2H, m)
MS (ESI⁺) m/z 246 (M+1)

Preparation 49

Methyl 3-(5-chloro-3-pyridyl)-2-(methoxyacetyl)acrylate

¹H-NMR (CDCl₃) δ 3.40 (1.5H, s), 3.43 (1.5H, s), 3.84 (1.5H, s), 3.88 (1.5H, s), 4.20 (1H, s), 4.34 (1H, s), 7.65-7.80 (2H, m), 8.51 (1H, br s), 8.58 (1H, br s).

Preparation 50

Ethyl 2-benzoyl-3-(tetrahydro-2H-pyran-4-yl)acrylate

¹H-NMR (CDCl₃) δ 1.14 (3H, t, J=6.7 Hz), 1.49-1.68 (2H, m), 2.30-2.48 (1H, m), 3.22-3.32 (2H, m), 3.62-3.70 (2H, m), 3.86-3.94 (2H, m), 4.15 (2H, q, J=6.7 Hz), 6.96 (1H, d, J=9.5 Hz), 7.47 (2H, dd, J=7.7, 7.7 Hz), 7.55-7.62 (2H, m), 7.86-7.92 (1H, m)

Preparation 51

Ethyl 2-butyryl-3-(5-methyl-3-pyridyl)acrylate

¹H-NMR (CDCl₃) δ 0.96 (3H, t, J=7 Hz), 1.28 (3H, t, J=7 Hz), 1.67 (2H, tq, J=7,7 Hz), 2.30 (3H, s), 2.55 (2H, t, J=7 Hz), 4.30 (2H, q, J=7 Hz), 7.49 (1H, s), 7.53 (1H, s), 7.62 (1H, s), 8.44 (1H, s)

Preparation 52

Ethyl 3-(5-chloro-3-pyridyl)-2-isobutyrylacrylate

¹H-NMR (CDCl₃) δ 1.09 (3.6H, d, J=7 Hz), 1.19 (2.4H, d, J=7 Hz), 1.20 (1.8H, t, J=7 Hz), 1.24 (1.21H, t, J=7 Hz), 2.75 (0.6H, sep, J=7 Hz), 3.15 (0.4H, sep, J=7 Hz), 4.33 (1.2H, q, J=7 Hz), 4.35 (0.8H, q, J=7 Hz), 7.51 (0.5H, s), 7.65-7.78 (1.5H, m), 8.50-8.59 (2H, m)
MS (ESI⁺) m/z 282 (M+1)

Preparation 53

Methyl 2-(cyclobutylcarbonyl)-3-(5-methyl-3-pyridyl)acrylate

¹H-NMR (CDCl₃) δ 1.99-2.47 (6H, m), 2.34 (1.5H, s), 2.35 (1.5H, s), 3.70-3.79 (1H, m), 3.84 (3H, s), 7.45-7.68 (2H, m), 8.42-8.47 (2H, m)
MS (ESI⁺) m/z 260 (M+1)

Preparation 54 tert-Butyl 2-(isopropoxyacetyl)-3-(5-methyl-3-pyridyl)acrylate

¹H-NMR (CDCl₃) δ 1.15 (3H, d, J=7 Hz), 1.23 (3H, d, J=7 Hz), 1.51 (4.5H, s), 1.56 (4.5H, s), 2.34 (1.5H, s), 2.35 (1.5H, s), 3.55-3.71 (1H, m), 4.20 (1.5H, s), 4.44 (1.5H, s), 7.50-7.66 (2H, m), 8.41-8.51 (2H, m)
MS (ESI⁺) m/z 320 (M+1)

Preparation 55

Ethyl 2-(3,3-dimethylbutanoyl)-3-(5-methyl-3-pyridyl)acrylate

¹H-NMR (CDCl₃) δ 1.04 (4.5H, s), 1.08 (4.5H, s), 1.29 (1.5H, t, J=7 Hz), 1.35 (1.5H, t, J=7 Hz), 2.34 (1.5H, s), 2.35 (1.5H, s), 2.48 (1H, s), 2.63 (1H, s), 4.30 (1H, q, J=7 Hz), 4.33 (1H, q, J=7 Hz), 7.47-7.60 (2H, m), 8.44-8.49 (2H, m)
MS (ESI⁺) m/z 290 (M+1)

Preparation 56

Methyl 2-(cyclopropylcarbonyl)-3-(5-methyl-3-pyridyl)acrylate

¹H-NMR (CDCl₃) δ 1.05-1.12 (2H, m), 1.23-1.30 (2H, m), 2.04-2.14 (1H, m), 3.87 (3H, s), 7.64 (1H, s), 7.77 (1H, s), 8.55 (1H, s)

Preparation 57

Methyl 3-(5-chloro-3-pyridyl)-2-(cyclopropylcarbonyl)acrylate

¹H-NMR (CDCl₃) δ 1.04-1.11 (2H, m), 1.22-1.30 (2H, m), 2.05-2.14 (1H, m), 3.86 (3H, s), 7.64 (1H, s), 7.77 (1H, s), 8.55 (2H, s)

Preparation 58

Methyl 3-(5-chloro-2-thienyl)-2-(cyclopropylcarbonyl)acrylate

Major Isomer
¹H-NMR (CDCl₃) δ 0.95-1.34 (4H, m), 2.20-2.32 (1H, m), 3.85 (3H, s), 6.91 (1H, d, J=4 Hz), 7.20 (H, d, J=4 Hz), 7.70 (1H, s).

Minor Isomer
¹H-NMR (CDCl₃) δ 0.95-1.34 (4H, m), 2.20-2.32 (1H, m), 3.96 (3H, s), 6.95 (1H, d, J=4 Hz), 7.24 (1H, d, J=4 Hz), 7.67 (1H, s).

Preparation 59

Ethyl 3-(2-chloro-4-pyridyl)-2-isobutyrylacrylate

Major Isomer
¹H-NMR (CDCl₃) δ 1.06 (6H, d, J=6 Hz), 1.35 (3H, t, J=7 Hz), 2.69 (1H, qq, J=6, 6 Hz), 4.27-4.36 (2H, m), 7.17 (1H, d, J=6 Hz), 7.29 (1H, s), 7.60 (1H, s), 8.40 (1H, d, J=6 Hz).

Minor Isomer
¹H-NMR (CDCl₃) δ 1.19 (6H, d, J=6 Hz), 1.27 (3H, t, J=7 Hz), 3.14 (1H, qq, J=6, 6 Hz), 4.27-4.36 (2H, m), 7.21 (1H, d, J=6 Hz), 7.34 (1H, s), 7.45 (1H, s), 8.42 (1H, d, J=6 Hz).

Preparation 60

Ethyl 3-(5-methyl-3-pyridyl)-2-propionylacrylate

¹H-NMR (CDCl₃) δ 1.13 (3H, t, J=7 Hz), 1.32 (3H, t, J=7 Hz), 2.33 (3H, s), 2.60 (2H, q, J=7 Hz), 4.32 (2H, q, J=7 Hz), 7.45 (1H, s), 7.64 (1H, s), 8.44 (2H, s)

Preparation 61

Ethyl 2-(2-ethylbutanoyl)-3-(5-methyl-3-pyridyl)acrylate $^1$H-NMR (CDCl$_3$) δ 0.88(2H, t, J=7 Hz), 0.91 (4H, t, J=7 Hz), 1.29 (1H, t, J=7 Hz), 1.34 (2H, t, J=7 Hz), 1.40-1.57 (2H, m), 1.64-1.83 (2H, m), 2.34 (1H, s), 2.35 (2H, s), 2.85-2.94 (1H, m), 4.31 (2/3H, q, J=7 Hz), 4.33 (4/3H, q, J=7 Hz), 7.51-7.76 (2H, m), 8.43-8.50 (2H, m)

MS (ESI$^+$) m/z 290 (M+1)

Preparation 62

Ethyl 2-(ethoxyacetyl)-3-(5-methyl-3-pyridyl)acrylate $^1$H-NMR (CDCl$_3$) δ 1.21 (4H, t, J=7 Hz), 1.35 (2H, t, J=7 Hz), 2.34 (2H, s), 2.36 (1H, s), 3.54 (1.3H, q, J=7 Hz), 3.56 (0.7H, q, J=7 Hz), 4.22 (1.3H, s), 4.32 (1.3H, q, J=7 Hz), 4.33 (0.7H, q, J=7 Hz), 4.38 (0.7H, s), 7.55-7.59 (1H, m), 7.70-7.72 (1H, m), 8.44-8.50 (2H, m)

MS (ESI$^+$) m/z 278 (M+1)

Preparation 63

Methyl 3-(5-bromo-3-pyridyl)-2-(cyclopropylcarbonyl)acrylate $^1$H-NMR (CDCl$_3$) δ 1.07 (2H, m), 1.28 (2H, m), 2.10 and 2.27 (1H, m), 3.87 (3H, s), 7.56 and 7.63 (1H, s), 7.89 and 7.92 (1H, m), 8.58 (1H, m), 8.66 and 8.68 (1H, m).

Preparation 64

Ethyl (2Z)-2-(4-fluorobenzoyl)-3-(5-methyl-3-pyridyl)acrylate $^1$H-NMR (CDCl$_3$) δ 1.21 (3H, t, J=6.7 Hz), 2.21 (3H, s), 4.25 (2H, q, J=6.7 Hz), 7.11 (2H, dd, J=8.5, 8.5 Hz), 7.42 (1H, s), 7.89 (1H, s), 7.95 (2H, dd, J=8.5, 7.8 Hz), 8.33 (1H, s), 8.41 (1H, s)

Preparation 65

Ethyl (2Z)-2-benzoyl-3-(3-quinolinyl)acrylate $^1$H-NMR (CDCl$_3$) δ 1.26 (3H, t, J=6.5 Hz), 4.27 (2H, q, J=6.5 Hz), 7.38-7.66 (5H, m), 7.70 (1H, d, J=7.5 Hz), 8.01 (2H, dd, J=7.5, 7.5 Hz), 8.04-8.30 (4H, m)

Preparation 66

To a ice-cooled solution of 1-ethyl-6-hydroxy-4-(5-methyl-3-pyridyl)-1H-pyrazolo[3,4-b]pyridine-5-carbonitrile (560 mg) and Et$_3$N (446 mg) in DCM (8.4 ml) was added trifluoromethanesulfonic anhydride (566 mg) and stirred for 4 hours at room temperature. The resulting solution was washed with water and brine, dried over MgSO$_4$. The solvent was evaporated and the residue was purified with silica gel column chromatography (CHCl$_3$-MeOH 1-3%) to give 5-cyano-1-ethyl-4-(5-methyl-3-pyridyl)-1H-pyrazolo[3,4-b]pyridin-6-yl trifluoromethanesulfonate (750 mg) as a yellow solid.

$^1$H-NMR (CDCl$_3$) δ 1.59 (3H, t, J=7 Hz), 2.53 (3H, s), 4.57 (2H, q, J=7 Hz), 7.90 (1H, s), 8.11 (1H, s), 8.70 (1H, s), 8.77 (1H, s)

The following compound(s) was(were) obtained in a similar manner to that of Example 115 mentioned below.

Preparation 67 bis(N-{[4-(5-Bromo-3-pyridyl)-6-cyclopentyl-1-ethyl-1H-pyrazolo[3,4-b]pyridin-5-yl]methyl}-N,N-diethylethanaminium) sulfate $^1$H-NMR (CDCl$_3$) δ 1.37 (9H, t, J=6.7 Hz), 1.53 (3H, t, J=6.7 Hz), 1.64-1.81 (2H, m), 1.82-2.18 (6H, m), 3.17 (6H, q, J=6.7 Hz), 3.82-3.93 (1H, m), 4.56 (2H, q, J=6.7 Hz), 5.09 (2H, s), 7.26 (1H, s), 7.66 (1H, s), 8.10 (1H, s), 8.74 (1H, s)

Preparation 68

To an ice-cooled solution of (2E)-3-[1-ethyl-6-(methoxymethyl)-4-(5-methyl-3-pyridinyl)-1H-pyrazolo[3,4-b]pyridin-5-yl]-2-propen-1-ol (44 mg) and diisopropylethylamine (20 mg) in DCM (1 ml) was added methyl chloroformate (13.5 mg) and stirred for 2 hours at room temperature. The solvent was dried up and the residue was purified with silica gel column chromatography (CHCl$_3$-MeOH 0-2%). (2E)-3-[1-Ethyl-6-(methoxymethyl)-4-(5-methyl-3-pyridyl)-1H-pyrazolo[3,4-b]pyridin-5-yl]-2-propen-1-yl methyl carbonate was obtained as a clear oil.

$^1$H-NMR (CDCl$_3$) δ 1.57 (3H, t, J=6.7 Hz), 2.43 (3H, s), 3.52 (3H, s), 3.79 (3H, s), 4.55-4.65 (4H, m), 4.69 (2H, s), 5.75 (1H, td, J=5.4, 12.2 Hz), 6.78 (1H, d, J=12.2 Hz), 7.56 (1H, s), 7.78 (1H, s), 8.48 (1H, s), 8.51 (1H, s)

EXAMPLE 1

To a stirred solution of ethyl 4-(3-chlorophenyl)-1-ethyl-6-methyl-4,7-dihydro-1H-pyrazolo[3,4-b]pyridine-5-carboxylate (135 mg) in THF (3 ml) was added 2,3-dichloro-5,6-dicyano-1,4-benzoquinone (97.5 mg) and the reaction mixture was stirred at room temperature for 3 hours. The reaction mixture was poured into saturated NaHCO$_3$ and extracted with EtOAc. The organic layer was washed with brine, dried over anhydrous MgSO$_4$ and concentrated in vacuo. The residue was purified by flash column chromatography on silica gel eluting with a mixture of EtOAc and n-hexane (1:5) to give ethyl 4-(3-chlorophenyl)-1-ethyl-6-methyl-1H-pyrazolo[3,4-b]pyridine-5-carboxylate (47 mg) as colorless oil.

$^1$H-NMR (CDCl$_3$) δ 1.06 (3H, t, J=7 Hz), 1.55 (3H, t, J=7Hz), 2.75 (3H, s), 4.15 (2H, q, J=7 Hz), 4.60 (2H, q, J=7 Hz), 7.35-7.50 (4H, m), 7.85 (1H, s)

MS (ESI$^+$) m/z 344 (M+1)

EXAMPLE 2

A mixture of tert-butyl -2-(methoxymethyl)-3-(5-methyl-3-pyridyl)acrylate (1.26 g) and 5-amino-1-ethylpyrazole (481 mg) in tert-BuOH (14 ml) was heated at 90° C. for 3 hours. After cooling the mixture was dissolved in THF (14 ml). To this was added 2,3-dichloro-5,6-dicyano-1,4-benzoquinone (982 mg) and the mixture was stirred at room temperature for 1 hour. The reaction mixture was poured into saturated aqueous NaHCO$_3$ and extracted with EtOAc. The organic layer was washed with brine, dried over anhydrous MgSO$_4$ and concentrated in vacuo. The residue was purified by flash column chromatography on silica gel eluting with a mixture of EtOAc and n-hexane (1:1) to give tert-butyl 1-ethyl-6-(methoxymethyl)-4-(5-methyl-3-pyridyl)-1H-pyrazolo[3,4-b]pyridine-5-carboxylate (1.23 g) as a colorless crystal.

$^1$H-NMR (CDCl$_3$) δ 1.29 (9H, s), 1.54 (3H, t, J=7 Hz), 2.44 (3H, s), 3.43 (3H, s), 4.67 (2H, q, J=7 Hz), 4.85 (2H, s), 7.6 (1H, d, J=1 Hz), 7.83 (1H, s), 8.57 (2H, s),

MS (ESI$^+$) m/z 383 (M+1)

The following compound(s) was(were) obtained in a similar manner to that of Example 2.

EXAMPLE 3

Ethyl 4-(2-chloro-4-pyridyl)-1-ethyl-6-methyl-1H-pyrazolo[3,4-b]pyridine-5-carboxylate $^1$H-NMR (CDCl$_3$) δ 1.09 (3H, t, J=7 Hz), 1.56 (3H, t, J=7 Hz), 2.77 (3H, s), 4.18 (2H, q, J=7 Hz), 4.61 (2H, q, J=7 Hz), 7.34 (1H, dd, J=7,1 Hz), 7.46 (1H, d, J=1 Hz), 7.82 (1H, s), 8.54 (1H, d, J=7 Hz)
MS (ESI$^+$) m/z 345 (M+1)
mp. 109-110° C.

EXAMPLE 4 tert-Butyl 4-(5-bromo-3-pyridyl)-1-ethyl-6-(methoxymethyl)-1H-pyrazolo[3,4-b]pyridine-5-carboxylate $^1$H-NMR (CDCl$_3$) δ 1.33 (9H, s), 1.55 (3H, t, J=7 Hz), 3.43 (3H, s), 4.67 (2H, q, J=7 Hz), 4.85 (2H, s), 7.84 (1H, s), 7.97 (1H, t, J=1 Hz), 8.68 (1H, t, J=1 Hz), 8.83 (1H, t, J=1 Hz)
MS (ESI$^+$) m/z 449 (M+2), 447 (M)

EXAMPLE 5

Ethyl 4-(5-bromo-3-pyridyl)-1-ethyl-6-methyl-1H-pyrazolo[3,4-b]pyridine-5-carboxylate $^1$H-NMR (CDCl$_3$) δ 1.36 (3H, t, J=7 Hz), 2.37 (3H, s), 4.34 (2H, q, J=7 Hz), 7.17 (1H, d, J=7 Hz), 7.29 (1H, s), 7.50 (1H, s), 8.40 (1H, d, J=7 Hz)
MS (ESI$^+$) m/z 391 (M+2), 389 (M)

EXAMPLE 6

Ethyl 1-ethyl-6-methyl-4-(5-methyl-3-pyridyl)-1H-pyrazolo[3,4-b]pyridine-5-carboxylate $^1$H-NMR (CDCl$_3$) δ 1.06 (3H, t, J=7 Hz), 1.55 (3H, t, J=7 Hz), 2.44 (3H, s), 2.76 (3H, s), 4.17 (2H, q, J=7 Hz), 4.60 (2H, q, J=7 Hz), 7.64 (1H, s), 7.84 (1H, s), 8.55 (2H, s),
MS (ESI$^+$) m/z 325 (M+1)

EXAMPLE 7

Ethyl 4-(5-bromo-3-pyridyl)-1-ethyl-6-(methoxymethyl)-1H-pyrazolo[3,4-b]pyridine-5-carboxylate $^1$H-NMR (CDCl$_3$) δ 1.13 (3H, t, J=7 Hz), 1.56 (H, t, J=7 Hz), 3.40 (3H, s), 4.19 (2H, q, J=7 Hz), 4.65 (2H, q, J=7 Hz), 4.85 (2H, s), 7.87 (1H, s), 7.98 (1H, t, J=1 Hz), 8.67 (1H, d, J=1 Hz), 8.80 (1H, d, J=1 Hz)
MS (ESI$^+$) m/z 421 (M+2), 419 (M)

EXAMPLE 8 tert-Butyl 6-[(cyclopropylmethoxy)methyl]-1-ethyl-4-(5-methyl-3-pyridyl)-1H-pyrazolo[3,4-b]pyridine-5-carboxylate $^1$H-NMR (CDCl$_3$) δ 0.18-0.23 (2H, m), 0.49-0.55 (2H, m), 1.05-1.1 (1H, m), 1.31 (9H, s), 1.55 (3H, t, J=7 Hz), 2.43 (3H, s), 3.35 (2H, d, J=7 Hz), 4.62 (2H, q, J=7 Hz), 4.95 (2H, s), 7.61 (1H, s), 7.83 (1H, s), 8.55 (1H, s), 8.57 (1H, s)
MS (ESI$^+$) m/z 423 (M+1)

EXAMPLE 9 tert-Butyl 4-(5-bromo-3-pyridyl)-6-[(cyclopropylmethoxy)methyl]-1-ethyl-1H-pyrazolo[3,4-b]pyridine-5-carboxylate $^1$H-NMR (CDCl$_3$) δ 0.18-0.22 (2H, m), 0.50-0.57 (2H, m), 1.13-1.16 (1H, m), 1.35 (9H, s), 1.55 (3H, t, J=7 Hz), 3.35 (2H, d, J=7 Hz), 4.63 (2H, q, J=7 Hz), 4.95 (2H, s), 7.83 (1H, s), 7.97 (1H, t, J=1 Hz), 8.67 (1H, d, J=1 Hz), 8.81 (1H, d, J=1 Hz)
MS (ESI$^+$) m/z 489 (M+2), 487 (M)

EXAMPLE 10 tert-Butyl 6-[(cyclohexylmethoxy)methyl]-1-ethyl-4-(5-methyl-3-pyridyl)-1H-pyrazolo[3,4-b]pyridine-5-carboxylate $^1$H-NMR (CDCl$_3$) δ 0.87-0.94 (2H, m), 1.13-1.27 (3H, m), 1.31 (9H, s), 1.54 (3H, t, J=7 Hz), 1.63-1.80 (6H, m), 2.44 (3H, s), 3.30 (2H, d, J=7 Hz), 4.67 (2H, q, J=7 Hz), 4.88 (2H, s), 7.62 (1H, s), 7.82 (1H, s), 8.57 (2H, s),
MS (ESI$^+$) m/z 465 (M+1)

EXAMPLE 11

Ethyl 6-cyclohexyl-1-ethyl-4-(5-methyl-3-pyridyl)-1H-pyrazolo[3,4-b]pyridine-5-carboxylate $^1$H-NMR (CDCl$_3$) δ 1.09 (3H, t, J=7 Hz), 1.31-1.44 (4H, m), 1.55 (3H, t, J=7 Hz), 1.72-1.99 (6H, m), 2.42 (3H, s), 2.87-2.97 (1H, m), 4.17 (2H, q, J=7 Hz), 4.70 (2H, q, J=7 Hz), 7.64 (1H, s), 7.80 (1H, s), 8.54 (1H, d, J=1 Hz), 8.57 (1H, d, J=1 Hz)

EXAMPLE 12

Ethyl 1,6-dimethyl-4-(5-methyl-3-pyridyl)-1H-pyrazolo[3,4-b]pyridine-5-carboxylate $^1$H-NMR (CDCl$_3$) δ 1.05 (3H, t, J=7 Hz), 2.43 (3H, s), 2.77 (3H, s), 4.16 (2H, q, J=7 Hz), 4.18 (3H, s), 7.53 (1H, s), 7.84 (1H, s), 8.58 (2H, s)
MS (ESI$^+$) m/z 311 (M+1)

EXAMPLE 13

Ethyl 1-ethyl-4-(5-methyl-3-pyridyl)-6-phenyl-1H-pyrazolo[3,4-b]pyridine-5-carboxylate $^1$H-NMR (CDCl$_3$) δ 0.87 (3H, t, J=7 Hz), 1.55(3H, t, J=7 Hz), 2.45(3H, s), 3.94(2H, q, J=7Hz), 4.67(2H, q, J=7 Hz), 7.45-7.47(3H, m), 7.67-7.80(2H, m), 7.90(1H, s), 8.59(2H, dd, J=7.1 Hz)
MS (ESI$^+$) m/z 387 (M+1)

EXAMPLE 14

Ethyl 1-ethyl-4-(5-methyl-3-pyridyl)-6-(2-thienyl)-1H-pyrazolo[3,4-b]pyridine-5-carboxylate $^1$H-NMR (CDCl$_3$) δ 1.03 (3H, t, J=7 Hz), 1.59 (3H, t, J=7 Hz), 2.44 (3H, s), 4.12 (2H, q, J=7 Hz), 4.63 (2H, q, J=7 Hz), 7.07-7.11 (1H, m), 7.44 (1H, d, J=4 Hz), 7.50 (1H, d, J=4 Hz), 7.70 (1H, s), 7.83 (1H, s), 8.59 (1H, s), 8.61 (1H, s)

EXAMPLE 15

Ethyl 1-ethyl-6-(4-methoxyphenyl)-4-(5-methyl-3-pyridyl)-1H-pyrazolo[3,4-b]pyridine-5-carboxylate $^1$H-NMR (CDCl$_3$) δ 0.92 (3H, t, J=7 Hz), 1.57 (3H, t, J=7 Hz), 2.43 (3H, s), 3.85 (3H, s), 3.97 (2H, q, J=7 Hz), 4.64 (2H, q, J=7 Hz), 6.98 (2H, d, J=8 Hz), 7.65 (2H, d, J=8 Hz), 7.77 (1H, s), 7.85 (1H, s), 8.55 (1H, s), 8.56 (1H, s)

EXAMPLE 16

Ethyl 6-({[tert-butyl(diphenyl)silyl]oxy}methyl)-1-ethyl-4-(5-methyl-3-pyridyl)-1H-pyrazolo[3,4-b]pyridine-5-carboxylate $^1$H-NMR (CDCl$_3$) δ 0.95 (3H, t, J=7 Hz), 1.03 (9H, s), 1.52 (3H, t, J=7 Hz), 2.45 (3H, s), 4.10 (2H, q, J=7 Hz), 4.52 (2H, q, J=7 Hz), 5.15 (2H, s), 7.30-7.40 (6H, m), 7.63 (1H, s), 7.67-7.72 (4H, m), 7.85 (1H, s), 8.55 (1H, s), 8.56 (1H, s)

MS (ESI$^+$) m/z 579 (M+1)

EXAMPLE 17

Ethyl 4-(4-chlorophenyl)-1-ethyl-6-methyl-1H-pyrazolo[3,4-b]pyridine-5-carboxylate $^1$H-NMR (CDCl$_3$) δ 1.05 (3H, t, J=8 Hz), 1.55 (3H, t, J=8 Hz), 2.74 (3H, s), 4.14 (2H, q, J=8 Hz), 4.59 (2H, q, J=8 Hz), 7.43 (2H, d, J=8 Hz), 7.48 (2H, q, J=8 Hz), 7.82 (1H, s).

EXAMPLE 18

Ethyl 4-(2-chlorophenyl)-1-ethyl-6-methyl-1H-pyrazolo[3,4-b]pyridine-5-carboxylate $^1$H-NMR (CDCl$_3$) δ 0.92 (3H, t, J=8 Hz), 1.56 (3H, t, J=8 Hz), 2.81 (3H, s), 4.06 (2H, q, J=8 Hz), 4.60 (2H, q, J=8 Hz), 7.25-7.46 (3H, m), 7.53 (1H, dd, J=8, 1 Hz), 7.66 (1H, s).

EXAMPLE 19

To a stirred solution of tert-butyl 1-ethyl-6-(methoxymethyl)-4-(5-methyl-3-pyridyl)-1H-pyrazolo[3,4-b]pyridine-5-carboxylate (100 mg) in toluene (2.5 ml) was added 1N diisobutylaluminum hydride in toluene (0.92 ml) at −78° C. and the reaction mixtrue was stirred at −78° C. for 1.5 hour. Another 1N diisobutylaluminum hydride in toluene (0.4 ml) was added at −78° C. and the reaction mxitrue was stirred at −78° C. for 2.5 hours. Another 1N diisobutylaluminum hydride in toluene (0.52 ml) was added at −78° C. and the reaction mxitrue was stirred at −78° C. for 1 hour. The reaction mixture was quenched with brine, filtrated through celite pad, and the filtrate was concentrated in vacuo. The residue was purified by flash column chromatography on silica gel eluting with a mixture of EtOAc and n-hexane (2:1) to give [1-ethyl-6-(methoxymethyl)-4-(5-methyl-3-pyridyl)-1H-pyrazolo[3,4-b]pyridin-5-yl]methanol (53 mg) as a light yellow oil.

$^1$H-NMR (CDCl$_3$) δ 1.56 (3H, t, J=7 Hz), 2.47 (3H, s), 3.56 (3H, s), 4.60 (2H, s), 4.61 (2H, q, J=7 Hz), 4.92 (2H, s), 7.81 (1H,s), 7.84 (1H, s), 8.59 (1H, s), 8.66 (1H, s)

MS (ESI$^+$) m/z 313 (M+1)

The following compound(s) was(were) obtained in a similar manner to that of Example 19.

EXAMPLE 20

[6-[(Cyclopropylmethoxy)methyl]-1-ethyl-4-(5-methyl-3-pyridyl)-1H-pyrazolo[3,4-b]pyridin-5-yl]methanol $^1$H-NMR (CDCl$_3$) δ 0.25-0.30 (2H, m), 0.58-6.63 (2H, m), 1.13-1.17 (1H, m), 1.56 (3H, t, J=7 Hz), 2.47 (3H, s), 3.51 (2H, d, J=7 Hz), 3.96 (1H, t, J=7 Hz), 4.61 (2H, q, J=7 Hz), 4.98 (2H, s), 7.84 (1H, s), 7.88 (1H, s), 8.58 (1H, s), 8.67 (1H, s)

MS (ESI$^+$) m/z 353 (M+1)

EXAMPLE 21

{4-(5-Bromo-3-pyridyl)-6-[(cyclopropylmethoxy)methyl]-1-ethyl-1H-pyrazolo[3,4-b]pyridin-5-yl}methanol $^1$H-NMR (CDCl$_3$) δ 0.17-0.29 (2H, m), 0.80-0.90 (2H, m), 1.07-1.15 (1H, m), 1.54 (3H, t, J=7 Hz), 3.50 (2H, d, J=7 Hz), 4.55-4.63 (4H, q, J=7 Hz), 4.97 (2H, s), 7.83 (1H, s), 8.24 (1H, s), 8.80-8.83 (2H, m)

MS (ESI$^+$) m/z 419 (M+2), 417 (M)

EXAMPLE 22

[6-[(Cyclohexylmethoxy)methyl]-1-ethyl-4-(5-methyl-3-pyridyl)-1H-pyrazolo[3,4-b]pyridin-5-yl]methanol $^1$H-NMR (CDCl$_3$) δ 0.90-1.05 (2H, m), 1.17-1.30 (3H, m), 1.57 (3H, s), 1.65-1.82 (6H, m), 2.47 (3H, s), 3.49 (2H, d, J=7 Hz), 3.80 (1H, t, J=7 Hz), 4.57-4.63 (4H, m), 4.95 (2H, s), 7.81 (1H, s), 7.85 (1H, s), 8.59 (1H, t, J=1 Hz), 8.66 (1H, d, J=1 Hz)

MS (ESI$^+$) m/z 395 (M+1)

EXAMPLE 23

(2E)-3-[1-Ethyl-6-(methoxymethyl)-4-(5-methyl-3-pyridyl)-1H-pyrazolo[3,4-b]pyridin-5-yl]-2-propen-1-ol $^1$H-NMR (CDCl$_3$) δ 1.56 (3H, t, J=6 Hz), 2.42 (3H, s), 3.50 (3H, s), 4.26 (2H, br), 4.62 (2H, q, J=6 Hz), 4.71 (2H, s), 5.75. (1H, td, J=3, 13 Hz), 6.68 (1H, d, J=13 Hz), 7.59 (1H, s), 7.75 (1H, s), 8.49 (2H, s)

EXAMPLE 24

[6-({[tert-Butyl(diphenyl)silyl]oxy}methyl)-1-ethyl-4-(5-methyl-3-pyridyl)-1H-pyrazolo[3,4-b]pyridin-5-yl]methanol $^1$H-NMR (CDCl$_3$) δ 1.09 (9H, s), 1.52 (3H, t, J=7 Hz), 2.48 (3H, s), 3.77 (1H, t, J=7 Hz), 4.52 (2H, q, J=7 Hz), 4.74 (2H, d, J=7 Hz), 5.14 (2H, s), 7.37-7.47 (6H, m), 7.73-7.77 (4H, m), 7.81 (1H, s), 8.38 (1H, d, J=1 Hz), 8.59 (1H, s), 8.66 (1H, s)

MS (ESI$^+$) m/z 537 (M+1)

EXAMPLE 25

To a stirred suspension of lithium aluminum hydride (8.8 mg) in diethyl ether (0.5 ml) was added a solution of ethyl 4-(5-bromo-3-pyridyl)-1-ethyl-6-methyl-1H-pyrazolo[3,4- b]pyridine-5-carboxylate (30 mg) in diethyl ether (1.5 ml) at −78° C. The mixture was gradually warmed to −10° C. over 8 hours and quenched with water at −10° C. The mixture was filtered through celite pad, and the filtrate was evaporated. The residue was purified by preparative thin layer chromatography eluting with a mixture of EtOAc and n-hexane (2:1) to give [4-(5-bromo-3-pyridyl)-1-ethyl-6-methyl-1H-pyrazolo[3,4-b]pyridin-5-yl]methanol (18 mg) as a colorless crystal.

$^1$H-NMR (CDCl$_3$) δ 1.56 (3H, t, J=7 Hz), 2.89 (3H, s), 4.60 (2H, q, J=7 Hz), 4.68 (2H, d, J=5 Hz), 7.72 (1H, s), 8.09 (1H, t, J=1 Hz), 8.74 (1H, t, J=1 Hz), 8.82 (1H, d, J=1 Hz)

MS (ESI$^+$) m/z 349 (M+2), 347 (M)

The following compound(s) was(were) obtained in a similar manner to that of Example 25.

EXAMPLE 26

[4-(2-Chloro-4-pyridyl)-1-ethyl-6-methyl-1H-pyrazolo[3,4-b]pyridin-5-yl]methanol $^1$H-NMR (CDCl$_3$) δ 1.55 (3H, t, J=7 Hz), 2.88 (3H, s), 4.60 (2H, q, J=7 Hz), 4.67 (2H, d, J=4 Hz), 7.43 (1H, dd, J=7,1 Hz), 7.55 (1H, d, J=1 Hz), 7.70 (1H, s), 8.57 (1H, d, J=7 Hz)

MS (ESI$^+$) m/z 303 (M+1)

EXAMPLE 27

[1-Ethyl-6-methyl-4-(5-methyl-3-pyridyl)-1H-pyrazolo[3,4-b]pyridin-5-yl]methanol $^1$H-NMR (CDCl$_3$) δ 1.55 (3H, t, J=7 Hz), 2.46 (3H, s), 3.89 (3H, s), 4.59 (2H, q, J=7 Hz), 4.69 (2H, s), 7.7 (2H, s), 8.59 (2H, s)

MS (ESI$^+$) m/z 283 (M+1)

EXAMPLE 28

[1,6-Dimethyl-4-(5-methyl-3-pyridyl)-1H-pyrazolo[3,4-b]pyridin-5-yl]methanol $^1$H-NMR (CDCl$_3$) δ 2.45 (3H, s), 2.90 (3H, s), 4.18 (3H, s), 4.70 (2H, s), 7.70 (2H, s), 8.58 (2H, s)

MS (ESI$^+$) m/z 269 (M+1)

EXAMPLE 29

[1-Ethyl-4-(5-methyl-3-pyridyl)-6-phenyl-1H-pyrazolo[3,4-b]pyridin-5-yl]methanol $^1$H-NMR (CDCl$_3$) δ 1.56 (3H, t, J=7 Hz), 2.49 (3H, s), 4.50 (2H, s), 4.63 (2H, q, J=7 Hz), 7.49-7.53 (3H, m), 7.75-7.83 (4H, m), 8.60 (1H, d, J=1 Hz), 8.70 (1H, d, J=1 Hz)

MS (ESI$^+$) m/z 345 (M+1)

EXAMPLE 30

[1-Ethyl-4-(5-methyl-3-pyridyl)-1H-pyrazolo[3,4-b]pyridine-5,6-diyl]dimethanol $^1$H-NMR (CDCl$_3$) δ 1.56 (3H, t, J=7 Hz), 2.89 (3H, s), 4.60 (2H, q, J=7 Hz), 4.68 (1H, d, J=5 Hz), 7.72 (1H, s), 8.09 (1H, t, J=1 Hz), 8.74 (1H, t, J=1 Hz), 8.82 (1H, d, J=1 Hz)

MS (ESI$^+$) m/z 299 (M+1)

EXAMPLE 31

To a stirred solution of ethyl 1-ethyl-6-(4-methoxyphenyl)-4-(5-methyl-3-pyridyl)-1H-pyrazolo[3,4-b]pyridine-5-carboxylate (88 mg) in DCM (3 ml) was added 1N diisobutylaluminum hydride in toluene (0.63 ml) at −78° C. and the reaction mixtrue was stirred at −78° C. for 1.5 hours. Another 1N diisobutylaluminum hydride in toluene (0.31 ml) was added at −78° C. and the reaction mxitrue was stirred at −78° C. for 2.5 hours. The reaction mixture was quenched with brine, filtrated through celite pad, and the filtrate was concentrated in vacuo. The residue-was purified by preparative thin layer chromatography eluting with a mixture of CHCl$_3$ and MeOH (9:1) to give [1-ethyl-6-(4-methoxyphenyl)-4-(5-methyl-3-pyridyl)-1H-pyrazolo[3,4-b]pyridin-5-yl]methanol (21 mg) as a light yellow oil.

$^1$H-NMR (CDCl$_3$) δ 1.57 (3H, t, J=7 Hz), 2.47 (3H, s), 3.88 (3H, s), 4.52 (2H, s), 4.62 (2H, q), 7.05 (2H, d), 7.74-7.85 (4H, m), 8.56 (1H, s), 8.70 (1H, s)

EXAMPLE 32

To a mixture of [1-ethyl-6-(methoxymethyl)-4-(5-methyl-3-pyridyl)-1H-pyrazolo[3,4-b]pyridin-5-yl]methanol (110 mg), Et$_3$N (0.29 ml) in N,N-dimethylsulfoxide (3 ml) was added sulfur trioxide-pyridine complex (168 mg) at room temperature and the mixture was stirred at room temperature for 1 hour. The reaction mixture was diluted with water and extracted with EtOAc. The organic layer was washed with saturated aqueous ammonium chloride, saturated aqueous NaHCO$_3$, water, brine, dried over anhydrous MgSO$_4$ and concentrated in vacuo. The residue was purified by flash column chromatography on silica gel eluting with a mixture of EtOAc and n-hexane(3:1) to give 1-ethyl-6-(methoxymethyl)-4-(5-methyl-3-pyridyl)-1H-pyrazolo[3,4-b]pyridine-5-carbaldehyde (86 mg) as a white crystal.

$^1$H-NMR (CDCl$_3$) δ 1.58 (3H, t, J=7 Hz), 2.47 (3H, s), 3.59 (3H, s), 4.67 (2H, q, J=7 Hz), 5.07 (2H, s), 7.60 (1H,s), 7.89 (1H, s), 8.55 (1H, d, J=1 Hz), 8.63 (1H, s), 10.14 (1H, s)

MS (ESI$^+$) m/z 311 (M+1)

The following compound(s) was(were) obtained in a similar manner to that of Example 32.

EXAMPLE 33

4-(5-Bromo-3-pyridyl)-1-ethyl-6-methyl-1H-pyrazolo[3,4-b]pyridine-5-carbaldehyde $^1$H-NMR (CDCl$_3$) δ 1.56 (3H, t, J=7 Hz), 3.00 (3H, s), 4.64 (2H, q, J=7 Hz), 7.85 (1H, s), 7.96 (1H, s), 8.65 (1H, s), 8.88 (1H, s), 10.18 (1H, s)

MS (ESI$^+$) m/z 345 (M)

EXAMPLE 34

1-Ethyl-6-methyl-4-(5-methyl-3-pyridyl)-1H-pyrazolo[3,4-b]pyridine-5-carbaldehyde $^1$H-NMR (CDCl$_3$) δ 1.58 (3H, t, J=7 Hz), 2.48 (3H, s), 3.00 (3H, s), 4.63 (2H, q, J=7 Hz), 7.60 (1H, s), 7.85 (1H, s), 8.58 (1H, s), 8.65 (1H, s), 10.12 (1H, s)

MS (ESI$^+$) m/z 281 (M+1)

EXAMPLE 35

6-[(Cyclopropylmethoxy)methyl]-1-ethyl-4-(5-methyl-3-pyridyl)-1H-pyrazolo[3,4-b]pyridine-5-carbaldehyde $^1$H-NMR (CDCl$_3$) δ 0.27-0.30 (2H, m), 0.55-0.60 (2H, m), 1.13-1.20 (1H, m), 1.57 (3H, t, J=7 Hz), 2.49 (3H, s), 3.50 (2H, d, J=7 Hz), 4.66 (2H, q, J=7 Hz), 5.13 (2H, s), 7.60 (1H, s), 7.89 (1H, s), 8.55 (1H, s), 8.64 (1H, s), 10.16 (1H, s)

MS (ESI$^+$) m/z 351 (M+1)

EXAMPLE 36

4-(5-Bromo-3-pyridyl)-6-[(cyclopropylmethoxy)methyl]-1-ethyl-1H-pyrazolo[3,4-b]pyridine-5-carbaldehyde $^1$H-NMR (CDCl$_3$) δ 0.20-0.29 (2H, m), 0.51-0.60 (2H, m), 1.09-1.14 (1H, m), 1.57 (3H, t, J=7 Hz), 3.50 (2H, d, J=7 Hz), 4.65 (2H, q, J=7 Hz), 5.10 (2H, s), 1.87 (1H, s), 7.94 (1H, t, J=1 Hz), 8.62 (1H, d, J=1 Hz), 8.84 (1H, d, J=1 Hz), 10.25 (1H, s)

MS (ESI$^+$) m/z 417 (M+2), 415 (M)

EXAMPLE 37

6-[(Cyclohexylmethoxy)methyl]-1-ethyl-4-(5-methyl-3-pyridyl)-1H-pyrazolo[3,4-b]pyridine-5-carbaldehyde $^1$H-NMR (CDCl$_3$) δ 0.90-1.10 (2H, m), 1.14-1.30 (3H, m), 1.59 (3H, t, J=7 Hz), 1.64-1.84 (6H, m), 2.45 (3H, s), 3.45 (1H, d, J=7 Hz), 4.65 (2H, q, J=7 Hz), 5.05 (2H, d, J=7 Hz), 7.59 (1H, t, J=1 Hz), 7.87 (1H, s), 8.54 (1H, t, J=1 Hz), 8.61 (1H, t, J=1 Hz), 10.17 (1H, s)

MS (ESI$^+$) m/z 393 (M+1)

EXAMPLE 38

1,6-Dimethyl-4-(5-methyl-3-pyridyl)-1H-pyrazolo[3,4-b]pyridine-5-carbaldehyde $^1$H-NMR (CDCl$_3$) δ 2.48 (3H, s), 3.01 (3H, s), 4.20 (3H, s), 7.60 (1H, s), 7.75 (1H, s), 8.57 (1H, s), 8.65 (1H, s), 10.11 (1H, s)

MS (ESI$^+$) m/z 267 (M+1)

EXAMPLE 39

1-Ethyl-4-(5-methyl-3-pyridyl)-6-phenyl-1H-pyrazolo[3,4-b]pyridine-5-carbaldehyde $^1$H-NMR (CDCl$_3$) δ 1.57 (3H, t, J=7 Hz), 2.45 (3H, s), 4.67 (2H, q, J=7 Hz), 7.53-7.57 (3H, m), 7.61-7.67 (3H, m), 7.89 (1H, s), 8.53 (1H, s), 8.59 (1H, d, J=1,Hz), 9.99 (1H, s)

MS (ESI$^+$) m/z 343 (M+1)

EXAMPLE 40

6-({[tert-Butyl(diphenyl)silyl]oxy}methyl)-1-ethyl-4-(5-methyl-3-pyridyl)-1H-pyrazolo[3,4-b]pyridine-5-carbaldehyde $^1$H-NMR (CDCl$_3$) δ 1.12 (9H, s), 1.55 (3H, t, J=7 Hz), 2.46 (3H, s), 4.57 (2H, q, J=7 Hz), 5.49 (2H, s), 7.30-7.37 (6H, m), 7.56 (1H, s), 7.71-7.75 (4H, m), 7.85 (1H, s), 8.51 (1H, s), 8.60 (1H, s), 10.10 (1H, s)

MS (ESI$^+$) m/z 535 (M+1)

EXAMPLE 41

Ethyl 3-[1-ethyl-6-formyl-4-(5-methyl-3-pyridyl)-1H-pyrazolo[3,4-b]pyridin-5-yl]propanoate $^1$H-NMR (CDCl$_3$) δ 1.20 (3H, t, J=7 Hz), 1.60 (3H, t, J=7 Hz), 2.45 (3H, s), 2.46 (2H, t, J=7 Hz), 4.05 (2H, q, J=7 Hz), 4.69 (2H, q, J=7 Hz), 7.50 (1H, t, J=1 Hz), 7.70 (1H, s), 8.45 (1H, d, J=1 Hz), 8.60 (1H, d, J=1 Hz), 10.26 (1H, s)

MS (ESI$^+$) m/z 367 (M+1)

EXAMPLE 42

Ethyl 3-[6-acetyl-1-ethyl-4-(5-methyl-3-pyridyl)-1H-pyrazolo[3,4-b]pyridin-5-yl]propanoate $^1$H-NMR (CDCl$_3$) δ 1.17 (3H, t, J=7 Hz), 1.59 (3H, t, J=7 Hz), 2.45 (3H, s), 2.46 (2H, t, J=7 Hz), 2.84 (3H, s), 3.19 (2H, t, J=7 Hz), 4.09 (214, q, J=7 Hz), 4.64 (2H, q, J=7 Hz), 7.50 (1H, s), 7.54(1H, s), 8.44 1H, d, J=1 Hz), 8.55 (1H, d, J=1 Hz)

MS (ESI$^+$) m/z 381 (M+1)

EXAMPLE 43

A mixture of [4-(2-chloro-4-pyridyl)-1-ethyl-6-methyl-1H-pyrazolo[3,4-b]pyridin-5-yl]methanol (30 mg), pyridinium chlorochromate (34.2 mg), sodium acetate (5.7 mg) in DCM (2 ml) was stirred at room temperature for 2 hours. The reaction mixture was diluted with diethylether and filtrated through celite pad. After evaporation of filtrate, the residue was purified by flash column chromatography on silica gel eluting with a mixture of EtOAc and n-hexane (1:4) to give 4-(2-chloro-4-pyridyl)-1-ethyl-6-methyl-1H-pyrazolo[3,4-b]pyridine-5-carbaldehyde (29 mg) as a white crystal.

$^1$H-NMR (CDCl$_3$) δ 1.55 (3H, t, J=7 Hz), 3.00 (3H, s), 4.64 (2H, d, J=7 Hz), 7.32 (1H, dd, J=7,1 Hz), 7.45 (1H, s), 7.80 (1H, s), 8.60 (1H, d, J=7 Hz), 10.13 (1H, s)

MS (ESI$^+$) m/z 301 (M+1)

EXAMPLE 44

To a suspension of sodium hydride (20.2 mg) in THF (0.8 ml) was added a solution of triethyl phosphonoacetate (117 mg) in THF (1.6 ml) at 0° C. and the mixture was stirred at room temperature for 30 minutes. A solution of 1-ethyl-6-(methoxymethyl)-4-(5-methyl-3-pyridyl)-1H-pyrazolo[3,4-b]pyridine-5-carbaldehyde (108 mg) in THF (4 ml) was added at 0° C. and the mixture was stirred at room temperature for 1 hour. The reaction mixture was diluted with water and extracted with EtOAc. The organic layer was washed with water, brine, dried over anhydrous MgSO$_4$ and concentrated in vacuo. The residue was purified by flash column chromatography on silica gel eluting with a mixture of EtOAc and n-hexane (3:1) then a mixture of MeOH and CHCl$_3$ (1:40) to give ethyl (2E)-3-[1-ethyl-6-(methoxymethyl)-4-(5-methyl-3-pyridyl)-1H-pyrazolo[3,4-b]pyridin-5-yl]acrylate (127 mg) as a yellow oil.

$^1$H-NMR (CDCl$_3$) δ 1.26 (3H, t, J=7 Hz), 1.57 (3H, t, J=7 Hz), 2.43 (3H, s), 3.55 (3H, s), 4.20 (2H, q, J=7 Hz), 4.64 (2H, q, J=7 Hz), 4.71 (2H, s), 6.04 (1H, d, J=16 Hz), 7.56 (1H, s), 7.80 (1H, s), 7.81 (1H, d, J=16 Hz), 8.50 (1H, s), 8.57 (1H, s)

MS (ESI$^+$) m/z 381 (M+1)

The following compound(s) was(were) obtained in a similar manner to that of Example 44.

EXAMPLE 45

Ethyl (2E)-3-[4-(2-chloro-4-pyridyl)-1-ethyl-6-methyl-1H-pyrazolo[3,4-b]pyridin-5-yl]acrylate $^1$H-NMR (CDCl$_3$) δ 1.29 (3H, t, J=7 Hz), 1.55 (3H, t, J=7 Hz), 2.77 (3H, s), 4.20 (2H, q, J=7 Hz), 4.59 (2H, q, J=7 Hz), 5.77 (1H, d, J=15 Hz), 7.26 (1H, s), 7.39 (1H, s), 7.71 (1H, s), 7.74 (1H, d, J=15 Hz), 8.53 (1H, d, J=5 Hz),
MS (ESI$^+$) m/z 381 (M+1)

EXAMPLE 46

Ethyl (2E)-3-[4-(5-bromo-3-pyridyl)-1-ethyl-6-methyl-1H-pyrazolo[3,4-b]pyridin-5-yl]acrylate $^1$H-NMR (CDCl$_3$) δ 1.29 (3H, t, J=7 Hz), 1.55 (3H, t, J=7 Hz), 2.78 (3H, s), 4.20 (2H, q, J=7 Hz), 4.59 (2H, q, J=7 Hz), 5.28 (1H, d, J=15 Hz), 7.75 (1H, d, J=1 Hz), 7.76 (1H, d, J=15 Hz), 7.90 (1H, t, J=1 Hz), 8.58 (1H, d, J=1 Hz), 8.78 (1H, d, J=1 Hz)

EXAMPLE 47

Ethyl (2E)-3-[1-ethyl-6-methyl-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 1.55 (3H, t, J=7 Hz), 2.43 (3H, s), 2.79 (3H, s), 4.19 (2H, q, J=7 Hz), 4.58 (2H, q, J=7 Hz), 5.29 (1H, d, J=15 Hz), 7.54 (1H, s), 7.74 (1H, s), 7.76 (1H, d, J=15 Hz), 8.48 (1H, t, J=1 Hz), 8.54 (1H, d, J=1 Hz)
MS (ESI$^+$) m/z 351 (M+1)

EXAMPLE 48

To a solution of triethyl phosphonoacetate (219 mg) in THF (2 ml) was added potassium tert-butoxide (103 mg) at 0° C. and the mixture was stirred at room temperature for 30 minutes. A solution of 6-[(cyclopropylmethoxy)methyl]-1-ethyl-4-(5-methyl-3-pyridyl)-1H-pyrazolo[3,4-b]pyridine-5-carbaldehyde (190 mg) in THF (4 ml) was added at 0° C. and the mixture was stirred at room temperature for 1 hour. The reaction mixture was diluted with water and extracted with EtOAc. The organic layer was washed with water, brine, dried over anhydrous MgSO$_4$ and concentrated in vacuo. The residue was purified by flash column chromatography on silica gel eluting with a mixture of EtOAc and n-hexane (1:1) to give ethyl (2E)-3-[6-[(cyclopropylmethoxy)methyl]-1-ethyl-4-(5-methyl-3-pyridyl)-1H-pyrazolo[3,4-b]pyridin-5-yl]acrylate (183 mg) as a yellow oil.

$^1$H-NMR (CDCl$_3$) δ 0.30-0.34 (2H, m), 0.57-0.61 (2H, m), 1.28 (3H, t, J=7 Hz), 1.33-1.37 (1H, m), 1.55 (3H, t, J=7 Hz), 2.44 (3H, s), 3.49 (2H, d, J=7 Hz), 4.19 (2H, q, J=7 Hz), 4.63 (2H, q, J=7 Hz), 4.75 (2H, s), 6.09 (1H, d, J=15 Hz), 7.55 (1H, s), 7.80 (1H, s), 7.84 (1H, d, J=15 Hz), 8.50 (1H, s), 8.55 (1H, s)
MS (ESI$^+$) m/z 421 (M+1)

The following compound(s) was(were) obtained in a similar manner to that of Example 48.

EXAMPLE 49

Ethyl (2E)-3-{4-(5-bromo-3-pyridyl)-6-[(cyclopropylmethoxy)methyl]-1-ethyl-5-methyl-1H-pyrazolo[3,4-b]pyridin-5-yl}acrylate $^1$H-NMR (CDCl$_3$) δ 0.28-0.34 (2H, m), 0.56-0.62 (2H, m), 1.14-1.20 (1H, m), 1.29 (3H, t, J=7 Hz), 1.55 (3H, t, J=7 Hz), 3.49 (2H, d, J=7 Hz), 4.20 (2H, q, J=7 Hz), 4.63 (2H, q, J=7 Hz), 4.76 (2H, s), 6.07 (1H, d, J=15 Hz), 7.81 (1H, s), 7.82 (1H, s), 7.89 (1H, d, J=15 Hz), 8.60 (1H, d, J=1 Hz), 8.80 (1H, d, J=1 Hz)
MS (ESI$^+$) m/z 487 (M+2), 485 (M)

EXAMPLE 50

Ethyl (2E)-3-[6-[(cyclohexylmethoxy)methyl]-1-ethyl-4-(5-methyl-3-pyridyl)-1H-pyrazolo[3,4-b]pyridin-5-yl]acrylate $^1$H-NMR (CDCl$_3$) δ 0.30-0.34 (2H, m), 0.57-0.61 (2H, m), 1.28 (3H, t, J=7 Hz), 1.33-1.37 (1H, m), 1.55 (3H, t, J=7 Hz), 2.44 (3H, s), 3.49 (2H, d, J=7 Hz), 4.19 (2H, q, J=7 Hz), 4.63 (2H, q, J=7 Hz), 4.75 (2H, s), 6.09 (1H, d, J=15 Hz), 7.55 (1H, s), 7.80 (1H, s), 7.84 (1H, d, J=15 Hz), 8.50 (1H, s), 8.55 (1H, s)
MS (ESI$^+$) m/z 421 (M+1)

EXAMPLE 51

Ethyl (2E)-3-[1,6-dimethyl-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 2.44 (3H, s), 2.80 (3H, s), 4.15 (3H, s), 4.19 (2H, q, J=7 Hz), 5.80 (1H, d, J=15 Hz), 7.55 (1H, d, J=1 Hz), 7.75 (1H, s), 7.78 (1H, d, J=15 Hz), 8.48 (1H, d, J=1 Hz), 8.57 (1H, d, J=1 Hz)
MS (ESI$^+$) m/z 337 (M+1)

EXAMPLE 52

Ethyl (2E)-3-[1-ethyl-4-(5-methyl-3-pyridyl)-6-phenyl-1H-pyrazolo[3,4-b]pyridin-5-yl]acrylate $^1$H-NMR (CDCl$_3$) δ 1.18 (3H, t, J=7 Hz), 1.57 (3H, t, J=7 Hz), 2.45 (3H, s), 4.09 (2H, q, J=7 Hz), 4.64 (2H, q, J=7 Hz), 5.42 (1H, d, J=15 Hz), 7.45-7.50 (3H, m), 7.57-7.60 (3H, m), 7.62 (1H, d, J=15 Hz), 7.80 (1H, s), 8.50 (1H, d, J=1 Hz), 8.57 (1H, s)
MS (ESI$^+$) m/z 413 (M+1)

EXAMPLE 53

Ethyl (2E)-3-[6-({[tert-butyl(diphenyl)silyl]oxy}methyl)-1-ethyl-4-(5-methyl-3-pyridyl)-1H-pyrazolo[3,4-b]pyridin-5-yl]acrylate $^1$H-NMR (CDCl$_3$) δ 1.08 (9H,s), 1.29 (3H, t, J=7 Hz), 1.54 (3H, t, J=7 Hz), 2.44 (3H, s), 4.20 (2H, q, J=7 Hz), 4.55 (2H, q, J=7 Hz), 4.99 (2H, s), 6.23 (1H, d, J=15 Hz), 7.33-7.42 (6H, m), 7.57 (1H, s), 7.75-7.79 (5H, m), 7.89 (1H, d, J=15 Hz), 8.50 (1H, d, J=1 Hz), 8.55 (1H, d, J=1 Hz)
MS (ESI$^+$) m/z 605 (M+1)

EXAMPLE 54

A mixture of ethyl (2E)-3-[1-ethyl-6-(methoxymethyl)-4-(5-methyl-3-pyridyl)-1H-pyrazolo[3,4-b]pyridin-5-yl]acrylate (50 mg) in EtOH (3 ml) was hydrogenated (3 atm) over platinum oxide (25 mg) at room temperature for 7 hours. The catalyst was filtered off through celite pad and the filtrate was concentrated in vacuo. The residue was purified by flash column chromatography on silica gel eluting with a mixture of EtOAc and n-hexane (1:1) then a mixture of MeOH and CHCl$_3$ (1:40) to give ethyl 3-[1-ethyl-6-(methoxymethyl)-4-(5-methyl-3-pyridyl)-1H-pyrazolo[3,4-b]pyridin-5-yl]propanoate (29 mg) as a colorless crystal.

$^1$H-NMR (CDCl$_3$) δ 1.20 (3H, t, J=7 Hz), 1.55 (3H, t, J=7 Hz), 2.40 (2H, t, J=7 Hz), 2.45 (3H, s), 3.10 (2H, t, J=7 Hz), 3.52 (3H, s), 4.06 (2H, q, J=7 Hz), 4.60 (2H, q, J=7 Hz), 4.78 (2H, s), 7.53 (1H, s), 7.59 (1H, d, J=1 Hz), 8.45 (1H, d, J=1 Hz), 8.57 (1H, s)

MS (ESI$^+$) m/z 383 (M+1)

EXAMPLE 55

To a solution of ethyl (2E)-3-[4-(5-bromo-3-pyridyl)-1-ethyl-6-methyl-1H-pyrazolo[3,4-b]pyridin-5-yl]acrylate (47 mg) in MeOH (2 ml) was added nickel chloride hexahydrate (7.26 mg) and sodium borohydride (10.7 mg) at −10° C. and the mixture was stirred at −10° C. for 15 minutes. The reaction mixture was diluted with water and extracted with EtOAc. The organic layer was washed with water and dried over anhydrous MgSO$_4$ and concentrated in vacuo. The residue was purified by preparative thin layer chromatography eluting with a mixture of EtOAc and n-hexane (1:1.5) to give ethyl 3-[4-(5-bromo-3-pyridyl)-1-ethyl-6-methyl-1H-pyrazolo[3,4-b]pyridin-5-yl]propanoate (12 mg) as a light yellow oil.

$^1$H-NMR (CDCl$_3$) δ 1.20 (3H, t, J=7 Hz), 1.55 (3H, t, J=7 Hz), 2.39 (2H, t, J=7 Hz), 2.77 (3H, s), 3.00 (2H, t, J=7 Hz), 4.18 (2H, q, J=7 Hz), 4.57 (2H, q, J=7 Hz), 7.55 (1H, s), 7.89 (1H, t, J=1 Hz), 8.55 (1H, s), 8.82 (1H, d, J=1 Hz)

MS (ESI$^+$) m/z 419 (M+2), 417 (M)

The following compound(s) was(were) obtained in a similar manner to that of Example 55.

EXAMPLE 56

Methyl 3-[1-ethyl-6-methyl-4-(5-methyl-3-pyridyl)-1H-pyrazolo[3,4-b]pyridin-5-yl]propanoate $^1$H-NMR (CDCl$_3$) δ 1.54 (3H, t, J=7 Hz), 2.40 (2H, t, J=7 Hz), 2.45 (3H, s), 2.77 (3H, s), 3.00 (2H, t, J=7 Hz), 3.63 (3H, s), 4.57 (2H, q, J=7 Hz), 7.50 (1H, t, J=1 Hz), 7.54 (1H, s), 8.44 (1H, d, J=1 Hz), 8.56 (1H, d, J=1 Hz)

MS (ESI$^+$) m/z 339 (M+1)

EXAMPLE 57

Ethyl 3-[6-[(cyclopropylmethoxy)methyl]-1-ethyl-4-(5-methyl-3-pyridyl)-1H-pyrazolo[3,4-b]pyridin-5-yl]propanoate $^1$H-NMR (CDCl$_3$) δ 0.23-0.27 (2H, m), 0.54-0.59 (2H, m), 0.93-0.99 (1H, m), 1.18 (3H, t, J=7Hz), 1.55 (3H, t, J=7Hz), 2.44 (2H, t, J=7Hz), 2.45 (3H, s), 3.12 (2H, t, J=7Hz), 4.05 (2H, q, J=7Hz), 4.60 (2H, q, J=7Hz), 4.75 (2H, s), 7.53 (1H, s), 7.58 (1H, s), 8.45 (1H, d, J=1 Hz), 8.59 (1H, d, J=1 Hz)

MS (ESI$^+$) m/z 423(M+1)

EXAMPLE 58

Ethyl 3-[6-[(cyclohexylmethoxy)methyl]-1-ethyl-4-(5-methyl-3-pyridyl)-1H-pyrazolo[3,4-b]pyridin-5-yl]propanoate $^1$H-NMR (CDCl$_3$) δ 0.89-1.01 (2H, m), 1.17 (3H, t, J=7 Hz), 1.18-1.29 (3H, m), 1.56 (3H, t, J=7 Hz), 1.62-1.80 (6H, m), 2.40 (2H, t, J=7 Hz), 2.45 (3H, s), 3.10 (2H, t, J=7 Hz), 3.42 (3H, d, J=7Hz), 4.05 (2H, q, J=7 Hz), 4.60 (2H, q, J=7 Hz), 4.80 (2H, s), 7.52 (1H, s), 7.59 (1H, s), 8.45 (1H, s), 8.58 (1H, s)

MS (ESI$^+$) m/z 465 (M+1)

EXAMPLE 59

Ethyl 3-[1,6-dimethyl-4-(5-methyl-3-pyridyl)-1H-pyrazolo[3,4-b]pyridin-5-yl]propanoate $^1$H-NMR (CDCl$_3$) δ 1.20 (3H, t, J=7 Hz), 2.37 (2H, t, J=7 Hz), 2.45 (3H, s), 2.77 (3H, s), 3.00 (2H, t, J=7 Hz), 4.15 (3H, s), 4.18 (2H, q, J=7 Hz), 7.50 (1H, s), 7.55 (1H, s), 8.45 (1H, s), 8.59 (1H, d, J=1 Hz)

EXAMPLE 60

Methyl 3-[1-ethyl-4-(5-methyl-3-pyridyl)-6-phenyl-1H-pyrazolo[3,4-b]pyridin-5-yl]propanoate $^1$H-NMR (CDCl$_3$) δ 1.54 (3H, t, J=7 Hz), 2.09 (2H, t, J=7 Hz), 2.47 (3H, s), 3.04 (2H, t, J=7 Hz), 3.45 (3H, s), 4.60 (2H, q, J=7 Hz), 7.44-7.59 (6H, m), 7.65 (1H, s), 8.51 (1H, s), 8.58 (1H, s)

MS (ESI$^+$) m/z 401 (M+1)

EXAMPLE 61

Ethyl 3-[6-({[tert-butyl(diphenyl)silyl]oxy}methyl)-1-ethyl-4-(5-methyl-3-pyridyl)-1H-pyrazolo[3,4-b]pyridin-5-yl]propanoate $^1$H-NMR (CDCl$_3$) δ 1.07 (9H, s), 1.17 (3H, t, J=7 Hz), 1.52 (3H, t, J=7 Hz), 2.42 (2H, t, J=7 Hz), 2.45 (3H, s), 3.15 (2H, t, J=7 Hz), 4.04(2H, q, J=7 Hz), 4.52 (2H, q, J=7 Hz), 5.04 (2H, s), 7.34-7.44 (6H, m), 7.53 (1H, s), 7.58 (1H, s), 7.74-7.77 (4H, m), 8.46 (1H, s), 8.57 (1H, s)

MS (ESI$^+$) m/z 607 (M+1)

EXAMPLE 62

A mixture of (2E)-3-[1-ethyl-6-(methoxymethyl)-4-(5-methyl-3-pyridyl)-1H-pyrazolo[3,4-b]pyridin-5-yl]-2-propen-1-ol (40 mg), ethyl (triphenylphosphanylidene)-acetate (49 mg), manganese dioxide (103 mg) and DCM (2 ml) was stirred at room temperature for 1 h. The reaction mixture was filtrated through celite pad. The solvent was evaporated and the residue was purified by flash column chromatography on silica gel (CHCl$_3$-MeOH 95:5) to give ethyl (2E,4E)-5-[1-ethyl-6-(methoxymethyl)-4-(5-methyl-3-pyridyl)-1H-pyrazolo[3,4-b]pyridin-5-yl]-2,4-pentadienoate (53 mg) as a colorless solid.

$^1$H-NMR (CDCl$_3$) δ 1.29 (3H, t, J=7 Hz), 1.56 (3H, t, J=7 Hz), 2.41 (3H, s), 3.52 (3H, s), 4.20 (2H, q, J=7 Hz), 4.62 (2H, q, J=7 Hz), 4.68 (2H, s), 5.78 (1H, d, J=11 Hz), 6.36 (1H, dd, J=11,13 Hz), 7.00 (1H, d, J=13 Hz), 7.30 (1H, dd, J=11,13 Hz), 7.58 (1H, s), 7.77 (1H, s), 8.50 (1H, s), 8.54 (1H, s)

EXAMPLE 63

A mixture of (2E,4E)-5-[1-ethyl-6-(methoxymethyl)-4-(5-methyl-3-pyridyl)-1H-pyrazolo[3,4-b]pyridin-5-yl]-2,4-pentadienoate (53 mg), palladium hydroxide on carbon (3.7 mg) and MeOH (2 ml) was shaken under hydrogen atmosphere (3 atm) at room temperature for 6 hours. The reaction mixture was filtrated through celite pad and the solvent was removed under reduced pressure to give ethyl 5-[1-ethyl-6-(methoxymethyl)-4-(5-methyl-3-pyridyl)-1H-pyrazolo[3,4-b]pyridin-5-yl]pentanoate (48 mg) as a colorless oil.

$^1$H-NMR (CDCl$_3$) δ 1.22 (3H, t, J=7 Hz), 1.31-1.64 (4H, m), 1.55 (3H, t, J=7 Hz), 2.21 (2H, t, J=6 Hz), 2.73 (3H, s), 3.51 (3H, s), 4.08 (2H, q, J=7 Hz), 4.69 (2H, q, J=7 Hz), 4.81 (2H, s), 7.60 (1H, s), 7.75 (1H, s), 8.25 (1H, s), 8.64 (1H, s)

EXAMPLE 64

To a stirred solution of ethyl 1-ethyl-4-(5-methyl-3-pyridyl)-6-phenyl-1H-pyrazolo[3,4-b]pyridine-5-carboxylate (257 mg) in a mixture of EtOH (2.5 ml) and water (2 ml) was added potassium hydroxide (1.32 g) and the mixture was refluxed for 12 hours. Another potassium hydroxide (439 mg) was added and the mixture was refluxed for 4.5 hours. After cooling, the reaction mixture was diluted with water and extracted with CHCl$_3$. The aqueous layer was acidified to pH3-4 by adding HCl and extracted with CHCl$_3$. The organic layer was washed with water, dried over anhydrous MgSO$_4$ and concentrated in vacuo. The residue was crystallized from EtOAc and n-hexane to give 1-ethyl-4-(5-methyl-3-pyridyl)-6-phenyl-1H-pyrazolo [3,4-b]pyridine-5-carboxylic acid (168 mg) as a light yellow crystal.

$^1$H-NMR (CDCl$_3$) δ 1.57 (3H, t, J=7Hz), 2.47 (3H, s), 4.67 (2H, q, J=7Hz), 7.45-7.53 (3H, m), 7.84-7.89 (3H, m), 7.92 (1H, s), 8.42 (1H, s), 8.72 (1H, s)

EXAMPLE 65

To a stirred solution of 1-ethyl-4-(5-methyl-3-pyridyl)-6-phenyl-1H-pyrazolo[3,4-b]pyridine-5-carboxylic acid (18 mg) and 4-methoxybenzyl amine (10.3 mg) in DMF (1 ml) was added O-(7-azabenzotriazol-1-yl)-N,N,N',N'-tetramethyluronium hexafluorophosphate (28.6 mg) and N,N-dimethylaminopyridine (9.2 mg). The reaction mixture was stirred at room temperature for 18 hours and at 50° for 5 hours. After cooling, the reaction mixture was diluted with water and extracted with EtOAc. The organic layer was washed with diluted HCl, water, saturated aqueous NaHCO$_3$, water, brine, dried over anhydrous MgSO4 and concentrated in vacuo. The crystalline residue was recrystallized from EtOAc and n-hexane to give 1-ethyl-N-(4-methoxybenzyl)-4-(5-methyl-3-pyridyl)-6-phenyl-1H-pyrazolo[3,4-b]pyridine-5-carboxamide (15.8 mg) as a colorless crystal.

$^1$H-NMR (CDCl$_3$) δ 1.57 (3H, t, J=7 Hz), 2.43 (3H, s), 3.76 (3H, s), 4.12 (2H, d, J=7 Hz), 4.65 (2H, q, J=7 Hz), 5.53 (1H, t, J=7 Hz), 6.65 (4H, q, J=7 Hz), 7.47-7.50(3H, m), 7.78-7.83 (3H, m), 7.89 (1H, s), 8.57 (1H, s), 8.65 (1H, s)

MS (ESI$^+$) m/z 478 (M+1)

mp. 203-204° C.

The following compound(s) was(were) obtained in a similar manner to that of Example 65.

EXAMPLE 66

N-(2,3-Dihydro-1H-inden-2-yl)-1-ethyl-4-(5-methyl-3-pyridyl)-6-phenyl-1H-pyrazolo[3,4-b]pyridine-5-carboxamide $^1$H-NMR (CDCl$_3$) δ 1.55 (3H, t, J=7 Hz), 2.21 (2H, dd, J=15, 3 Hz), 2.47 (3H, s), 3.00 (2H, dd, J=15, 7 Hz), 4.50-4.55 (1H, m), 4.64 (2H, q, J=7 Hz), 5.55 (1H, d, J=7 Hz), 7.04-7.12 (4H, m), 7.47-7.51 (3H, m), 7.73-7.79 (3H, m), 7.88 (1H, s), 8.58-8.63 (2H, m)

MS (ESI$^+$) m/z 474 (M+1)

mp. 269-270° C.

EXAMPLE 67

[1-Ethyl-6-(methoxymethyl)-4-(5-methyl-3-pyridyl)-1H-pyrazolo[3,4-b]pyridin-5-yl]methanol (57 mg), toluene (0.3 ml), 50% aqueous NaOH solution and tetrabutylammonim sulfate (32 mg) were stirred at room temperature. tert-Butyl bromoacetate (53 mg) was added dropwise and stirring was continued for 2 hours. Water (3 ml) was added and organic layer was separated. Water layer was extracted with EtOAc (×2). Organic layer was combined and dried over MgSO$_4$. The solvent was evaporated to give dark brown oil. The crude compound was purified by flash column chromatography on silica gel (CHCl$_3$:MeOH=50:1) to give tert-butyl {[1-ethyl-6-(methoxymethyl)-4-(5-methyl-3-pyridyl)-1H-pyrazolo[3,4-b]pyridin-5-yl]methoxy}acetate (53 mg) as colorless oil $^1$H-NMR (CDCl$_3$) δ 1.46 (9H, s), 1.54 (3H, t, J=7 Hz), 2.45 (3H, s), 3.55 (3H, s), 3.97 (2H, s), 4.62 (2H, s), 4.63 (2H, q, J=7 Hz), 4.96 (2H, s), 7.74 (1H, s), 7.78 (1H, s), 8.58 (2H, s)

The following compound(s) was(were) obtained in a similar manner to that of Example 67.

EXAMPLE 68

[6-[(Benzyloxy)methyl]-1-ethyl-4-(5-methyl-3-pyridyl)-1H-pyrazolo[3,4-b]pyridin-5-yl]methanol $^1$H-NMR (CDCl$_3$) δ 1.55 (3H, t, J=7 Hz), 2.43 (3H, s), 4.40 (2H, s), 4.49 (2H, s), 4.59-4.66 (3H, m), 4.89 (2H, s), 7.29-7.38 (5H, m), 7.69 (1H, s), 7.75 (1H, s), 8.57 (1H, s), 8.62 (1H, s)

MS (ESI$^+$) m/z 389 (M+1)

[5-[(Benzyloxy)methyl]-1-ethyl-4-(5-methyl-3-pyridyl)-1H-pyrazolo[3,4-b]pyridin-6-yl]methanol $^1$H-NMR (CDCl$_3$) δ 1.57 (3H, t, J=7 Hz), 2.46 (3H, s), 3.57 (1H, t, J=7Hz), 4.57-4.64 (4H, m), 4.74 (2H, s), 5.04 (2H, s), 7.32-7.43 (5H, m), 7.83 (1H, s), 7.85 (1H, s), 8.59 (1H, s), 8.67 (1H, s)

MS (ESI$^+$) m/z 389 (M+1)

EXAMPLE 69 tert-Butyl {[1-ethyl-6-(methoxymethyl)-4-(5-methyl-3-pyridyl)-1H-pyrazolo[3,4-b]pyridin-5-yl]methoxy}acetate (50 mg) was dissolved in 80% trifluoroacetic acid-DCM (2 ml) and stirred at room temperature for 30 minutes. Solvent was evaporated and the residue was purified by flash column chromatography on silica gel (CHCl$_3$-MeOH 95:5) to give {[1-ethyl-6-(methoxymethyl)-4-(5-methyl-3-pyridyl)-1H-pyrazolo[3,4-b]pyridin-5-yl]methoxy}acetic acid (25 mg) as colorless solid.

$^1$H-NMR (CDCl$_3$) δ 1.51 (3H, t, J=6 Hz), 2.36 (3H, s), 3.47 (3H, s), 4.54 (2H, s), 4.56 (2H, q, J=6 Hz), 4.87 (2H, s), 7.68 (1H, s), 7.73 (1H, s), 8.51 (1H, s), 8.72 (1H, s)

EXAMPLE 70

To a solution of 4-(5-bromo-3-pyridyl)-1-ethyl-6-methyl-1H-pyrazolo[3,4-b]pyridine-5-carbaldehyde (34 mg) in DMF (1 ml) was added pyridine (0.032 ml) and hydroxylamine hydrochloride (13.7 mg) at room temperature and the mixture was stirred at room temperature for 2 hours. The reaction mixture was diluted with water and extracted with EtOAc. The organic layer was washed with water, brine, dried over anhydrous MgSO$_4$ and concentrated in vacuo to give 4-(5-bromo-3-pyridyl)-1-ethyl-6-methyl-1H-pyrazolo[3,4-b]pyridine-5-carbaldehyde oxime (35 mg) as a yellow crystal.

$^1$H-NMR (CDCl$_3$) δ 1.55 (3H, t, J=7 Hz), 2.84 (3H, s), 4.60 (2H, q, J=7 Hz), 7.49 (1H, s), 7.75 (1H, s), 7.91 (1H, t, J=1 Hz), 8.23 (1H, s), 8.60 (1H, d, J=1 Hz), 8.78 (1H, d, J=1 Hz)

MS (ESI$^+$) m/z 362 (M+2), 360 (M)

The following compound(s) was(were) obtained in a similar manner to that of Example 70.

EXAMPLE 71

1-Ethyl-6-methyl-4-(5-methyl-3-pyridyl)-1H-pyrazolo[3,4-b]pyridine-5-carbaldehyde oxime $^1$H-NMR (CDCl$_3$) δ 1.56 (3H, t, J=7 Hz), 2.45 (3H, s), 2.85 (3H, s), 4.60 (2H, q, J=7 Hz), 7.56 (1H, s), 7.75 (1H, s), 8.20 (1H, s), 8.50 (1H, s), 8.55 (1H, s)

MS (ESI$^+$) m/z 296 (M+1)

EXAMPLE 72

Ethyl 3-[1-ethyl-6-[(E)-(hydroxyimino)methyl]-4-(5-methyl-3-pyridyl)-1H-pyrazolo[3,4-b]pyridin-5-yl]propanoate $^1$H-NMR (CDCl$_3$) δ 1.20 (3H, t, J=7 Hz), 1.55 (3H, t, J=7 Hz), 2.45 (2H, t, J=7 Hz), 2.46 (3H, s), 3.23 (2H, t, J=7 Hz), 4.05 (2H, q, J=7 Hz), 4.61 (2H, q, J=7 Hz), 7.51 (1H, t, J=1 Hz), 7.62 (1H, s), 8.45 (1H, s), 8.59 (1H, s), 8.60 (1H, s)

MS (ESI$^+$) m/z 382 (M+1)

EXAMPLE 73

A mixture of 4-(5-bromo-3-pyridyl)-1-ethyl-6-methyl-1H-pyrazolo[3,4-b]pyridine-5-carbaldehyde oxime (34 mg) and acetic anhydride (1 ml) was stirred at 90° C. for 2 hours and 150° C. for 2 hours. The reaction mixture was diluted with water and extracted with EtOAc. The organic layer was washed with water, brine, dried over anhydrous MgSO$_4$ and concentrated in vacuo. The residue was purified by flash column chromatography on silica gel eluting with a mixture of EtOAc and n-hexane (1:2). The crystalline residue was recrystallized from EtOAc and n-hexane to give 4-(5-bromo-3-pyridyl)-1-ethyl-6-methyl-1H-pyrazolo[3,4-b]pyridine-5-carbonitrile (15.5 mg) as a colorless crystal.

$^1$H-NMR (CDCl$_3$) δ 1.56 (3H, t, J=7 Hz), 2.95 (3H, s), 4.61 (2H, q, J=7 Hz), 7.96 (1H, s), 8.19 (1H, t, J=1 Hz), 8.85 (1H, d, J=1 Hz), 8.90 (1H, d, J=1 Hz)

MS (ESI$^+$) m/z 344 (M+2), 342 (M)

mp. 165-166° C.

The following compound(s) was(were) obtained in a similar manner to that of Example 73.

EXAMPLE 74

1-Ethyl-6-methyl-4-(5-methyl-3-pyridyl)-1H-pyrazolo[3,4-b]pyridine-5-carbonitrile $^1$H-NMR (CDCl$_3$) δ 1.56 (3H, t, J=7Hz), 2.49 (3H, s), 2.94 (3H, s), 4.60 (2H, q, J=7 Hz), 7.87 (1H, s), 7.97 (1H, s), 8.65 (1H, s), 8.74 (1H, s)

MS (ESI$^+$) m/z 278 (M+1)

mp. 160-161° C.

EXAMPLE 75

Ethyl 3-[6-cyano-1-ethyl-4-(5-methyl-3-pyridyl)-1H-pyrazolo[3,4-b]pyridin-5-yl]propanoate $^1$H-NMR (CDCl$_3$) δ 1.20 (3H, t, J=7 Hz), 1.57 (3H, t, J=7 Hz), 2.48 (3H, s), 2.54 (2H, t, J=7 Hz), 3.26 (2H, t, J=7 Hz), 4.06 (2H, q, J=7 Hz), 4.63 (2H, q, J=7 Hz), 7.54 (1H, s), 7.75 (1H, s), 8.46 (1H, s), 8.64 (1H, s)

MS (ESI$^+$) m/z 364 (M+1)

EXAMPLE 76

To a stirred solution of ethyl 3-[6-({[tert-butyl(diphenyl)silyl]oxy}methyl)-1-ethyl-4-(5-methyl-3-pyridyl)-1H-pyrazolo[3,4-b]pyridin-5-yl]propanoate (313 mg) in THF (10 ml) was added 1N tetrabutyl ammonium fluoride in THF (0.52 ml) at 0° C. and the reaction mixture was stirred at room temperature for 2 hours. The reaction mixture was diluted with water and extracted with EtOAc. The organic layer was washed with water, brine, dried over anhydrous MgSO$_4$ and concentrated in vacuo. The residue was purified by flash column chromatography on silica gel eluting with a mixture of EtOAc and n-hexane (3:1) then a mixture of MeOH and CHCl$_3$ (1:50) to give ethyl 3-[1-ethyl-6-(hydroxymethyl)-4-(5-methyl-3-pyridyl)-1H-pyrazolo[3,4-b]pyridin-5-yl]propanoate (100 mg) as a yellow oil.

$^1$H-NMR (CDCl$_3$) δ 1.19 (3H, t, J=7 Hz), 1.57 (3H, t, J=7 Hz), 2.33 (2H, t, J=7 Hz), 2.46 (3H, s), 2.93 (2H, t, J=7 Hz), 4.05 (2H, q, J=7 Hz), 4.62 (2H, q, J=7 Hz), 4.73 (1H, t, J=5 Hz), 4.96 (2H, d, J=5 Hz), 7.53 (1H, s), 7.63 (1H, t, J=1 Hz), 8.47 (1H, s), 8.60 (1H, s)

MS (ESI$^+$) m/z 369 (M+1)

EXAMPLE 77

To a stirred solution of ethyl 3-[1-ethyl-6-formyl-4-(5-methyl-3-pyridyl)-1H-pyrazolo[3,4-b]pyridin-5-yl]propanoate (42 mg) in THF (1 ml) was added 0.93M methylmagnesium bromide in THF (0.18 ml) at 0° C. and the reaction mixture was stirred at 0° C. for 1 hour. Another 0.93M methylmagnesium bromide in THF (0.18 ml) was added at 0° C. and the reaction mixture was stirred at 0° C. for 1 hour. The reaction mixture was diluted with saturated aqueous ammonium chloride and extracted with EtOAc. The organic layer was washed with water, brine, dried over anhydrous MgSO$_4$ and concentrated in vacuo. The residue was purified by preparative thin layer chromatography on silica gel eluting with a mixture of EtOAc and n-hexane (3:1) to give ethyl 3-[1-ethyl-6-(1-hydroxyethyl)-4-(5-methyl-3-pyridyl)-1H-pyrazolo[3,4-b]pyridin-5-yl]propanoate (34 mg) as a colorless oil.

$^1$H-NMR (CDCl$_3$) δ 1.19 (3H, t, J=7 Hz), 1.54 (3H, s), 1.59 (3H, t, J=7 Hz), 2.23-2.40 (2H, m), 2.46 (3H, s), 3.00 (2H, t, J=7 Hz), 4.07 (2H, q, J=7 Hz), 4.50 (1H, d, J=7 Hz), 4.60 (2H, q, J=7 Hz), 5.15-5.23 (1H, m), 7.52 (1H, s), 7.60 (1H, s), 8.46 (1H, s), 8.60 (1H, s)

MS (ESI$^+$) m/z 383 (M+1)

EXAMPLE 78

To a mixture of ethyl 3-[1-ethyl-6-formyl-4-(5-methyl-3-pyridyl)-1H-pyrazolo[3,4-b]pyridin-5-yl]propanoate (30 mg), morpholine (36 μl) and AcOH (0.1 ml) in EtOH (1 ml) was added sodium cyanoborohydride (15 mg) at room temperature and stirred at room temperature for 5 hours. The reaction mixture was acidified to pH 3 with HCl and stirred for 30 minutes. The solution was neutralized with aqueous NaOH and extracted with EtOAc (×3). The organic layer was combined, washed with brine and dried over MgSO$_4$. The solvent was removed under reduced pressure. The residue was purified by flash column chromatography on silica gel (CHCl$_3$-MeOH 97:3) to give ethyl 3-[1-ethyl-4-(5-methyl-3-pyridyl)-6-(4-morpholinylmethyl)-1H-pyrazolo[3,4-b]pyridin-5-yl]propanoate (35 mg) as an oil.

$^1$H-NMR (CDCl$_3$) δ 1.19 (3H, t, J=6 Hz), 1.56 (3H, t, J=6 Hz), 2.46 (3H, s), 2.62 (4H, s), 3.10 (2H, t, J=6 Hz), 3.69 (2H, t, J=6 Hz), 4.06 (2H, q, J=6 Hz), 4.59 (2H, q, J=6 Hz), 7.51 (1H, s), 7.55 (1H, s), 8.45 (1H, s), 8.58 (1H, s)

EXAMPLE 79

A mixture of ethyl 3-[1-ethyl-6-formyl-4-(5-methyl-3-pyridyl)-1H-pyrazolo[3,4-b]pyridin-5-yl]propanoate (30 mg), 1-[(1-isocyanoethyl)sulfonyl]-4-methylbenzene (17.6 mg), potassium carbonate (17 mg) in MeOH (1 ml) was refluxed for 1.5 hours. After cooling, the mixture was diluted with water and extracted with EtOAc. The aqueous layer was acidified to pH3-4 by adding 1N HCl and extracted with CHCl$_3$. The organic layer was washed with water, dried over anhydrous MgSO$_4$ and concentrated in vacuo. The residue was purified by preparative thin layer chromatography eluting with a mixture of MeOH and CHCl$_3$ (1:10). Crystallization from EtOAc-n-hexane gave 3-[1-ethyl-6-(4-methyl-1,3-oxazol-5-yl)-4-(5-methyl-3-pyridyl)-1H-pyrazolo[3,4-b]pyridin-5-yl]propanoic acid (10 mg) as a colorless crystal.

$^1$H-NMR (CDCl$_3$) δ 1.57 (3H, t, J=7 Hz), 2.38 (2H, t, J=7 Hz), 2.47 (3H, s), 2.58 (3H, s), 3.20 (2H, t, J=7 Hz), 4.60 (2H, q, J=7Hz), 4.80(2H, s), 7.58 (1H, s), 7.60 (1H, s), 7.97 (1H, s), 8.48 (1H, s), 8.57 (1H, s)

MS (ESI$^+$) m/z 392 (M+1)

mp. 184-185.5° C.

EXAMPLE 80

To a suspension of diethyl (cyanomethyl)phosphonate (17.4 mg) in THF (0.5 ml) was added potassium tert-butoxide (11.3 mg) at 0° C. and the mixture was stirred at room temperature for 30 minutes. A solution of ethyl 3-[1-ethyl-6-formyl-4-(5-methyl-3-pyridyl)-1H-pyrazolo[3,4-b]pyridin-5-yl]propanoate (20 mg) in THF (0.5 ml) was added at 0° C. and the mixture was stirred at room temperature for 1.5 hours. The reaction mixture was diluted with water and extracted with EtOAc. The organic layer was washed with water, brine, dried over anhydrous MgSO$_4$ and concentrated in vacuo. The residue was purified by preparative thin layer chromatography eluting with a mixture of EtOAc and n-hexane (1:1) to give ethyl 3-[6-[(E)-2-cyanovinyl]-1-ethyl-4-(5-methyl-3-pyridyl)-1H-pyrazolo[3,4-b]pyridin-5-yl]propanoate (17 mg) as a colorless crystal.

$^1$H-NMR (CDCl$_3$) δ 1.24 (3H, t, J=7 Hz), 1.57 (3H, t, J=7Hz), 2.39 (2H, t, J=7 Hz), 2.48 (3H, s), 3.09 (2H, t, J=7 Hz), 4.10 (2H, q, J=7 Hz), 4.60(2H, q, J=7 Hz), 6.93 (1H, d, J=15 Hz), 7.50 (1H, s), 7.63 (1H, s), 7.86 (1H, d, J=15 Hz), 8.44 (1H, s), 8.61 (1H, s),

MS (ESI$^+$) m/z 390 (M+1)

EXAMPLE 81

To a mixture of ethyl 3-[1-ethyl-6-(1-hydroxyethyl)-4-(5-methyl-3-pyridyl)-1H-pyrazolo[3,4-b]pyridin-5-yl]propanoate (103 mg), Et$_3$N (72 μl) and N,N-dimenthylaminopyridine (2.1 mg) in DCM (1 ml) was added N,N-dimethylcarbamyl chloride (72 μl) and stirred for 5 hours at room temperature. The reaction mixture was diluted with CHCl$_3$, washed with water and brine and dried over MgSO$_4$. The solvent was removed under reduced pressure. The residue was purified by flash column chromatography on silica gel (CHCl$_3$-MeOH 97:3) to give [1-ethyl-5-(hydroxymethyl)-4-(5-methyl-3-pyridyl)-1H-pyrazolo[3,4-b]pyridin-6-yl]methyl dimethylcarbamate (85 mg) as an oil.

$^1$H-NMR (CDCl$_3$) δ 1.55 (3H, t, J=7 Hz), 2.45 (3H, s), 2.94 (3H, s), 3.01 (3H, s), 3.95 (1H, br), 4.60 (2H, q, J=7 Hz), 4.70 (2H, s), 5.54 (2H, s), 7.77 (1H, s), 7.82 (1H, s), 8.55 (1H, s), 8.61 (1H, s)

EXAMPLE 82

To a stirred solution of ethyl (2E)-3-[1-ethyl-6-(methoxymethyl)-4-(5-methyl-3-pyridyl)-1H-pyrazolo[3,4-b]pyridin-5-yl]acrylate (30 mg) in EtOH (2 ml) was added 1N aqueous NaOH (0.16 ml) and the mixture was stirred at 40° C. for 1 hour. After cooling, the reaction mixture was acidified to pH3-4 by adding 1N HCl (0.16 ml). The mixture was diluted with brine and extracted with CHCl$_3$. The organic layer was dried over anhydrous MgSO$_4$ and concentrated in vacuo. The residue was purified by preparative thin layer chromatography eluting with a mixture of MeOH and CHCl$_3$ (1:10). The residue was recrystallized from EtOAc-n-hexane to give (2E)-3-[1-ethyl-6-(methoxymethyl)-4-(5-methyl-3-pyridyl)-1H-pyrazolo[3,4-b]pyridin-5-yl]acrylic acid (15 mg) as a colorless crystal.

$^1$H-NMR (CDCl$_3$) δ 1.59 (3H, t, J=7 Hz), 2.47 (3H, s), 3.55 (3H, s), 4.65 (2H, q, J=7 Hz), 4.75 (2H, s), 6.05 (1H, d, J=15 Hz), 7.64 (1H, s), 7.84 (1H, s), 7.89 (1H, d, J=15 Hz), 8.53 (1H, d, J=1 Hz), 8.57 (1H, s)

MS (ESI$^+$) m/z 353 (M+1)

mp. 195-196° C.

The following compound(s) was(were) obtained in a similar manner to that of Example 82.

EXAMPLE 83

(2E)-3-[4-(2-Chloro-4-pyridyl)-1-ethyl-6-methyl-1H-pyrazolo[3,4-b]pyridin-5-yl]acrylic acid $^1$H-NMR (CDCl$_3$) δ 1.57 (3H, t, J=7 Hz), 2.79 (3H, s), 4.60 (2H, q, J=7 Hz), 5.82 (1H, d, J=15 Hz), 7.27 (1H, s), 7.40 (1H, s), 7.73 (1H, s), 7.84 (1H, d, J=15 Hz), 8.55 (1H, d, J=5 Hz), MS (ESI$^+$) m/z 341 (M+1)

mp. 180° C.

EXAMPLE 84

(2E)-3-[4-(5-Bromo-3-pyridyl)-1-ethyl-6-methyl-1H-pyrazolo[3,4-b]pyridin-5-yl]acrylic acid $^1$H-NMR (CDCl$_3$) δ 1.57 (3H, t, J=7 Hz), 2.80 (3H, s), 4.60 (2H, q, J=7 Hz), 5.80 (1H, d, J=15 Hz), 7.77 (1H, s), 7.84 (1H, d, J=15 Hz), 7.94 (1H, t, J=1 Hz), 8.60 (1H, d, J=1 Hz), 8.79 (1H, d, J=1 Hz)

MS (ESI$^+$) m/z 389 (M+2), 387 (M)

mp. 189-190° C.

EXAMPLE 85

(2E)-3-[1-Ethyl-6-methyl-4-(5-methyl-3-pyridyl)-1H-pyrazolo[3,4-b]pyridin-5-yl]acrylic acid $^1$H-NMR (CDCl$_3$) δ 1.56 (3H, t, J=7 Hz), 2.47 (3H, s), 2.80 (3H, s), 4.60 (2H, q, J=7 Hz), 5.82 (1H, d, J=15 Hz), 7.70 (1H, s), 7.77 (1H, s), 7.82 (1H, d, J=15 Hz), 8.50 (1H, s), 8.53 (1H, s)

MS (ESI⁺) m/z 323 (M+1)
mp. 239-241° C.

EXAMPLE 86

4-(5-Bromo-3-pyridyl)-1-ethyl-6-(methoxymethyl)-1H-pyrazolo[3,4-b]pyridine-5-carboxylic acid ¹H-NMR (CDCl₃) δ 1.55 (3H, t, J=7 Hz), 3.45 (3H, s), 4.65 (2H, q, J=7 Hz), 5.52 (2H, s), 7.90 (1H, s), 8.10 (1H, s), 8.77 (2H, s)
MS (ESI⁺) m/z 393 (M+2), 391 (M)
mp. 162-163° C.

EXAMPLE 87

(2E)-3-[6-[(Cyclopropylmethoxy)methyl]-1-ethyl-4-(5-methyl-3-pyridyl)-1H-pyrazolo[3,4-b]pyridin-5-yl]acrylic acid ¹H-NMR (CDCl₃) δ 0.24-0.33 (2H, m), 0.55-0.60 (2H, m), 1.17-1.23 (1H, m), 1.56 (3H, t, J=7 Hz), 2.46 (3H, s), 3.50 (2H, d, J=7 Hz), 4.64 (2H, q, J=7 Hz), 4.80 (2H, s), 6.10 (1H, d, J=15 Hz), 7.67 (1H, s), 7.84 (1H, s), 7.91 (1H, d, J=7Hz), 8.53 (1H, s), 8.56 (1H, s)
MS (ESI⁺) m/z 393 (M+1)
mp. 187-189° C.

EXAMPLE 88

(2E)-3-{4-(5-Bromo-3-pyridyl)-6-[(cyclopropylmethoxy)methyl]-1-ethyl-1H-pyrazolo[3,4-b]pyridin-5-yl}acrylic acid ¹H-NMR (CDCl₃) δ 0.28-0.34 (2H, m), 0.55-0.61 (2H, m), 1.12-1.20 (1H, m), 1.57 (3H, t, J=7 Hz), 3.48 (2H, d, J=7 Hz), 4.64 (2H, q, J=7 Hz), 4.78 (2H, s), 6.08 (1H, d, J=15 Hz), 7.82 (1H, s), 7.84 (1H, d, J=15 Hz), 7.85 (1H, t, J=1 Hz), 8.64 (1H, d, J=1 Hz), 8.80 (1H, d, J=1 Hz)
MS (ESI⁺) m/z 459 (M+2), 457 (M)
mp. 183-184° C.

EXAMPLE 89

(2E)-3-[6-[(Cyclohexylmethoxy)methyl]-1-ethyl-4-(5-methyl-3-pyridyl)-1H-pyrazolo[3,4-b]pyridin-5-yl]acrylic acid ¹H-NMR (CDCl₃) δ 0.95-1.05 (2H, m), 1.15-1.29 (3H, m), 1.59 (3H, t, J=7 Hz), 1.65-1.85 (6H, m), 2.45 (3H, s), 3.43 (2H, d, J=7 Hz), 4.64 (2H, q, J=7 Hz), 4.74 (2H, s), 6.05 (1H, d, J=15 Hz), 7.64 (1H, s), 7.81 (1H, s), 7.89 (1H, d, J=15 Hz), 8.51 (1H, s), 8.55 (1H, s)
MS (ESI⁺) m/z 435 (M+1)
mp. 172-173° C.

EXAMPLE 90

(2E)-3-[1,6-Dimethyl-4-(5-methyl-3-pyridyl)-1H-pyrazolo[3,4-b]pyridin-5-yl]acrylic acid ¹H-NMR (CDCl₃-CD₃OD) δ 2.45 (3H, s), 2.80 (3H, s), 4.17 (3H, s), 5.78 (1H, d, J=15 Hz), 7.60 (1H, s), 7.75 (1H, s), 7.76 (1H, d, J=15 Hz), 8.43 (1H, s), 8.50 (1H, s),
MS (ESI⁺) m/z 309 (M+1)
mp. 269-272° C.

EXAMPLE 91

(2E)-3-[1-Ethyl-4-(5-methyl-3-pyridyl)-6-phenyl-1H-pyrazolo[3,4-b]pyridin-5-yl]acrylic acid ¹H-NMR (CDCl₃) δ 1.57 (3H, t, J=7 Hz), 2.45 (3H, s), 4.64 (2H, q, J=7 Hz), 5.42 (1H, d, J=15 Hz), 7.43-7.48 (3H, m), 7.55-7.60 (2H, m), 7.65 (1H, d, J=15 Hz), 7.67 (1H, s), 7.82 (1H, s), 8.49 (1H, d, J=1 Hz), 8.55 (1H, s)
MS (ESI⁺) m/z 385 (M+1)
mp. 254-255° C.

EXAMPLE 92

3-[1-Ethyl-6-(methoxymethyl)-4-(5-methyl-3-pyridyl)-1H-pyrazolo[3,4-b]pyridin-5-yl]propanoic acid ¹H-NMR (CDCl₃) δ 1.55 (3H, t, J=7 Hz), 2.45 (3H, s), 2.50 (2H, t, J=7 Hz), 3.10 (2H, t, J=7 Hz), 3.52 (3H, s), 4.61 (2H, q, J=7 Hz), 4.80 (2H, s), 7.56 (1H, s), 7.59 (1H, d, J=1 Hz), 8.46 (1H, s), 8.55 (1H, s)
MS (ESI⁺) m/z 355 (M+1)
mp. 154-155° C.

EXAMPLE 93

3-[4-(5-Bromo-3-pyridyl)-1-ethyl-6-methyl-1H-pyrazolo[3,4-b]pyridin-5-yl]propanoic acid ¹H-NMR (CDCl₃) δ 1.54 (3H, t, J=7Hz), 2.46 (2H, t, J=7 Hz), 2.76 (3H, s), 3.02 (2H, t, J=7 Hz), 4.57 (2H, q, J=7 Hz), 7.55 (1H, s), 7.87 (1H, s), 8.55 (1H, s), 8.80 (1H, s)
MS (ESI⁺) m/z 391 (M+2), 389 (M)
mp. 178-179.5° C.

EXAMPLE 94

3-[1-Ethyl-6-methyl-4-(5-methyl-3-pyridyl)-1H-pyrazolo[3,4-b]pyridin-5-yl]propanoic acid ¹H-NMR (CDCl₃) δ 1.55 (3H, t, J=7 Hz), 2.45 (3H, s), 2.50 (2H, t, J=7 Hz), 2.78 (3H, s), 3.04 (2H, t, J=7 Hz), 4.57 (2H, q, J=7 Hz), 7.53 (1H, s), 7.55 (1H, s), 8.45 (1H, d, J=1 Hz), 8.55 (1H, s)
MS (ESI⁺) m/z 325 (M+1)
mp. 179-181° C.

EXAMPLE 95

3-[6-[(Cyclopropylmethoxy)methyl]-1-ethyl-4-(5-methyl-3-pyridyl)-1H-pyrazolo[3,4-b]pyridin-5-yl]propanoic acid ¹H-NMR (CDCl₃) δ 0.24-0.29 (2H, m), 0.55-0.60 (2H, m), 1.1-1.17 (1H, m), 1.55 (3H, t, J=7 Hz), 2.45 (3H, s), 2.55 (2H, t, J=7 Hz), 3.14 (2H, t, J=7 Hz), 3.48 (2H, d, J=7 Hz), 4.60 (2H, q, J=7 Hz), 4.86 (2H, s), 7.55 (1H, s), 7.57 (1H, d, J=1 Hz), 8.46 (1H, d, J=1 Hz), 8.55 (1H, d, J=1 Hz)
MS (ESI⁺) m/z 393 (M+1)
mp. 179-180° C.

EXAMPLE 96

3-[6-[(Cyclohexylmethoxy)methyl]-1-ethyl-4-(5-methyl-3-pyridyl)-1H-pyrazolo[3,4-b]pyridin-5-yl]propanoic acid $^1$H-NMR (CDCl$_3$) δ 0.91-1.01 (2H, m), 1.15-1.27 (3H, m), 1.54 (3H, t, J=7 Hz), 1.61-1.82 (6H, m), 2.45 (3H, s), 2.51 (2H, t, J=7 Hz), 3.12 (2H, t, J=7 Hz), 3.42 (2H, d, J=7 Hz), 4.60 (2H, q, J=7 Hz), 4.80 (2H, s), 7.55 (1H, s), 7.57 (1H, s), 8.47 (1H, s), 8.55 (1H, s)
MS (ESI$^+$) m/z 437 (M+1)
mp. 183-184° C.

EXAMPLE 97

3-[1,6-Dimethyl-4-(5-methyl-3-pyridyl)-1H-pyrazolo[3,4-b]pyridin-5-yl]propanoic acid $^1$H-NMR (CDCl$_3$) δ 2.45 (3H, s), 2.50 (2H, t, J=7 Hz), 2.79 (3H, s), 3.04 (2H, t, J=7 Hz), 4.15 (3H, s), 5.80 (1H, d, J=15 Hz), 7.53 (1H, s), 7.55 (1H, s), 8.45 (1H, s), 8.54 (1H, s)
MS (ESI$^+$) m/z 311 (M+1)
mp. 205-207° C.

EXAMPLE 98

3-[1-Ethyl-4-(5-methyl-3-pyridyl)-6-phenyl-1H-pyrazolo[3,4-b]pyridin-5-yl]propanoic acid $^1$H-NMR (CDCl$_3$) δ 1.52 (3H, t, J=7 Hz), 2.10 (2H, t, J=7 Hz), 2.45 (3H, s), 3.06 (2H, t, J=7 Hz), 4.59 (2H, q, J=7 Hz), 7.48-7.58 (6H, m), 7.63 (1H, s), 8.49 (1H, s), 8.54 (1H, s)
MS (ESI$^+$) m/z 387 (M+1)
mp. 235-237° C.

EXAMPLE 99

5-[1-Ethyl-6-(methoxymethyl)-4-(5-methyl-3-pyridyl)-1H-pyrazolo[3,4-b]pyridin-5-yl]pentanoic acid $^1$H-NMR (CDCl$_3$) δ 1.41-1.64 (4H, m), 1.55 (3H, t, J=7 Hz), 2.22 (2H, t, J=7 Hz), 2.45 (3H, s), 2.67-2.80 (2H, m), 3.51 (3H, s), 4.59 (2H, q, J=7 Hz), 4.76 (2H, s), 7.55 (2H, s), 8.45 (1H, s), 8.56 (1H, s)

EXAMPLE 100

3-[6-Cyano-1-ethyl-4-(5-methyl-3-pyridyl)-1H-pyrazolo[3,4-b]pyridin-5-yl]propanoic acid $^1$H-NMR (CDCl$_3$) δ 1.58 (3H, t, J=7 Hz), 2.47 (3H, s), 2.70 (2H, t, J=7 Hz), 3.30 (2H, t, J=7 Hz), 4.63 (2H, q, J=7 Hz), 7.58 (1H, s), 7.71 (1H, s), 8.45 (1H, d, J=1 Hz), 8.57 (1H, s)
MS (ESI$^+$) m/z 336 (M+1)
mp. 209-210° C.

EXAMPLE 101

3-[6-Acetyl-1-ethyl-4-(5-methyl-3-pyridyl)-1H-pyrazolo[3,4-b]pyridin-5-yl]propanoic acid $^1$H-NMR (CDCl$_3$) δ 1.59 (3H, t, J=7 Hz), 2.44 (3H, s), 2.54 (2H, t, J=7 Hz), 2.86 (3H, s), 3.20-3.30 (2H, m), 4.64 (2H, q, J=7Hz), 7.53 (1H, s), 7.61 (1H, s), 8.42 (1H, s), 8.55 (1H, s)
MS (ESI$^+$) m/z 336 (M+1)

EXAMPLE 102

3-[6-[(E)-2-Cyanovinyl]-1-ethyl-4-(5-methyl-3-pyridyl)-1H-pyrazolo[3,4-b]pyridin-5-yl]propanoic acid $^1$H-NMR (CDCl$_3$) δ 1.57 (3H, t, J=7 Hz), 2.46 (3H, s), 2.47 (2H, t, J=7 Hz), 3.13 (2H, t, J=7 Hz), 4.60 (2H, q, J=7 Hz), 6.94 (1H, d, J=15 Hz), 7.53 (1H, s), 7.87 (1H, d, J=15 Hz), 8.44 (1H, s), 8.57 (1H, s)
MS (ESI$^+$) m/z 362 (M+1)

EXAMPLE 103

3-[1-Ethyl-4-(5-methyl-3-pyridyl)-6-(4-morpholinylmethyl)-1H-pyrazolo[3,4-b]pyridin-5-yl]propanoic acid $^1$H-NMR (CDCl$_3$) δ 1.54 (3H, t, J=7 Hz), 2.44 (3H, s), 2.52 (2H, t, J=8 Hz), 2.68 (4H, t, J=5 Hz), 3.13 (2H, t, J=8 Hz), 3.70 (4H, t, J=5 Hz), 3.90 (2H, s), 4.58 (2H, q, J=7 Hz), 7.72 (2H, s), 8.45 (1H, s), 8.55 (1H, s)

EXAMPLE 104

A mixture of benzoylacetonitrile (365 mg), tetrahydropyran-4-carbaldehyde (287 mg), 5-amino-1-methylpyrazole (289 mg) in pyridine (7.3 ml) was stirred for 2 days at 110° C. The solvent was removed under reduced pressure. The residue was purified with silica gel column chromatography to give pure 1-ethyl-6-phenyl-4-(tetrahydro-2H-pyran-4-yl)-1H-pyrazolo[3,4-b]pyridine-5-carbonitrile (359 mg).

$^1$H-NMR (CDCl$_3$) δ 1.56 (3H, t, J=6.6 Hz), 1.94 (2H, d, J=12.2 Hz), 2.25-2.42 (2H, m), 3.62-3.79 (3H, m), 4.16-4.24 (2H, m), 4.62 (2H, q, J=6.6 Hz), 7.51-7.58 (3H, m), 7.85-7.93 (2H, m), 8.35 (1H, s)

The following compound(s) was(were) obtained in a similar manner to that of Example 104.

EXAMPLE 105

1-Ethyl-4-isopropyl-6-phenyl-1H-pyrazolo[3,4-b]pyridine-5-carbonitrile $^1$H-NMR (CDCl$_3$) δ 1.55 (3H, t, J=6.7 Hz), 1.60 (6H, d, J=6.6 Hz), 3.81 (1H, h, J=6.6 Hz), 4.61 (2H, q, J=6.7 Hz), 7.51-7.56 (3H, m), 7.88-7.92 (2H, m)

EXAMPLE 106

4-Cyclohexyl-1-ethyl-6-phenyl-1H-pyrazolo[3,4-b]pyridine-5-carbonitrile $^1$H-NMR (CDCl$_3$) δ 1.38-1.62 (4H, m), 1.52 (3H, t, J=6.5 Hz), 1.84-2.10 (6H, m), 3.38-3.50 (1H, m), 4.59 (2H, q, J=6.5 Hz), 7.50-7.56 (3H, m), 7.85-7.91 (2H, m), 8.29 (1H, s)

EXAMPLE 107

1-Ethyl-6-phenyl-4-(2-phenylethyl)-1H-pyrazolo[3,4-b]pyridine-5-carbonitrile $^1$H-NMR (CDCl$_3$) δ 1.56 (3H, t, J=6.7 Hz), 3.13 (2H, t, J=7.1 Hz), 3.52 (2H, t, J=7.1 Hz), 4.60 (2H, q, J=6.7 Hz), 7.19-7.33 (5H, m), 7.52 (3H, m), 7.88-7.94 (2H, m), 7.95 (1H, s)

EXAMPLE 108

A mixture of methyl 3-cyclohexyl-2-(cyclopropylcarbonyl)acrylate (6.01 g) and 1-ethyl-1H-pyrazol-5-amine (2.97 mg) in tert-BuOH (60 ml) was refluxed for 22 hours. The solvent was evaporated off, and the residue was dissolved in dioxane (60 ml). To the mixture was added 4,5-dichloro-3,6-dioxo-1,4-cyclohexadiene-1,2-dicarbonitrile (5.77 g). The mixture was stirred for 6 h at room temperature. The mixture was filtered off, and the filtrate was evaporated. The residue was dissolved in EtOAc (20 ml), and to the solution was added silicagel, followed by hexanes (100 ml). The mixture was filtered, and filter cake was washed with EtOAc-hexanes (1-5). The filtrate was evaporated off. Silicagel column chromatography (EtOAc-hexanes, a linear gradient of EtOAc from 0 to 15%) afforded methyl 4-cyclohexyl-6-cyclopropyl-1-ethyl-1H-pyrazolo[3,4-b]pyridine-5-carboxylate as a colorless oil, which was crystallized upon standing (4.36 g).

$^1$H-NMR (CDCl$_3$) δ 1.00 (2H, m), 1.23 (2H, m), 1.37-1.44 (3H, m), 1.47 (3H, t, J=7.3 Hz), 1.81-2.05 (8H, m), 2.66 (1H, m), 3.98 (3H, s), 4.46 (2H, q, J=7.3 Hz), 8.08 (1H, s)

The following compound(s) was(were) obtained in a similar manner to that of Example 108.

EXAMPLE 109

Methyl 4-(4-amino-3,5-dichlorophenyl)-6-cyclopropyl-1-ethyl-1H-pyrazolo[3,4-b]pyridine-5-carboxylate $^1$H-NMR (CDCl$_3$) δ 1.06 (2H, m), 1.28 (2H, m), 1.50 (3H, t, J=7.3 Hz), 2.19 (1H, m), 3.77 (3H, s), 4.50 (2H, q, J=7.3 Hz), 4.67 (2H, br s), 7.39 (2H, s), 7.85 (1H, s).

EXAMPLE 110

Methyl 4-(5-bromo-3-pyridyl)-6-cyclopropyl-1-ethyl-1H-pyrazolo[3,4-b]pyridine-5-carboxylate $^1$H-NMR (CDCl$_3$) δ 1.09 (2H, m), 1.31 (2H, m), 1.51 (3H, t, J=7.2 Hz), 2.27 (1H, m), 3.73 (3H, s), 4.53 (2H, q, J=7.2 Hz), 7.79 (1H, s), 7.98 (1H, m), 8.07 (1H, d, J=1.6 Hz), 8.79 (1H, d, J=2.1 Hz).

The following compound(s) was(were) obtained in a similar manner to that of Example 25.

EXAMPLE 111

[6-Cyclohexyl-1-ethyl-4-(5-methyl-3-pyridyl)-1H-pyrazolo[3,4-b]pyridin-5-yl]methanol $^1$H-NMR (CDCl$_3$) δ 1.41-1.50 (4H, m), 1.55 (3H, t, J=7 Hz), 1.87-1.95 (6H, m), 2.46 (3H, s), 3.22-3.33 (1H, m), 4.60 (2H, q, J=7 Hz), 4.67 (2H, d, J=5 Hz), 7.67 (1H, s), 7.69 (1H, s), 8.56-8.60 (2H, m)

EXAMPLE 112

[4-(Cyclohexylmethyl)-1-ethyl-6-phenyl-1H-pyrazolo[3,4-b]pyridin-5-yl]methanol $^1$H-NMR (CDCl$_3$) δ 1.10-1.22 (5H, m), 1.52 (3H, t, J=7 Hz), 1.65-1.78 (6H, m), 3.09 (2H, d, J=7 Hz), 4.57 (2H, q, J=7 Hz), 4.73 (2H, d, J=5 Hz), 7.48-7.52 (3H, m), 7.65-7.69 (2H, m), 8.05 (1H, s)

EXAMPLE 113

[4-(6-Chloro-3-pyridyl)-1-ethyl-6-phenyl-1H-pyrazolo[3,4-b]pyridin-5-yl]methanol $^1$H-NMR (CDCl$_3$) δ 1.56 (3H, t, J=7 Hz), 1.73 (1H, t, J=7 Hz), 4.47 (2H, d, J=7 Hz), 4.64 (2H, q, J=7 Hz), 7.50-7.57 (4H, m), 7.74-7.77 (2H, m), 7.82 (1H, s), 8.07 (1H, dd, J=7, 1 Hz), 8.74 (1H, d, J=1 Hz)

EXAMPLE 114

[1-Ethyl-6-(5-methyl-3-isoxazolyl)-4-(5-methyl-3-pyridyl)-1H-pyrazolo[3,4-b]pyridin-5-yl]methanol $^1$H-NMR (CDCl$_3$) δ 1.59 (3H, t, J=7 Hz), 2.49 (3H, s), 2.59 (3H, s), 4.63 (2H, s), 4.65 (2H, q, J=7 Hz), 6.79 (1H, s), 7.89 (1H, s), 7.90 (1H, s), 8.60 (1H, s), 8.69 (1H, s).

The following compound(s) was(were) obtained in a similar manner to that of Example 32.

EXAMPLE 115

6-Cyclohexyl-1-ethyl-4-(5-methyl-3-pyridyl)-1H-pyrazolo[3,4-b]pyridine-5-carbaldehyde $^1$H-NMR (CDCl$_3$) δ 1.25-1.54 (4H, m), 1.58 (3H, t, J=7 Hz), 1.72-1.97 (6H, m), 2.46 (3H, s), 3.22-3.31 (1H, m), 4.62 (2H, q, J=7Hz), 7.58 (1H, s), 7.81(1H, s), 8.54 (1H, d, J=1 Hz), 8.62 (1H, d, J=1 Hz), 10.12 (1H, s)

EXAMPLE 116

4-(5-Bromo-3-pyridyl)-6-cyclopropyl-1-ethyl-1H-pyrazolo[3,4-b]pyridine-5-carbaldehyde $^1$H-NMR (CDCl$_3$) δ 1.16 (2H, m), 1.36 (2H, m), 1.53 (3H, t, J=7.2 Hz), 3.29 (1H, m), 4.53 (2H, q, J=7.2 Hz), 7.77 (1H, s), 7.95 (1H, m), 8.63 (1H, m), 8.85 (1H, m), 10.26 (1H, s).

EXAMPLE 117

1-Ethyl-6-isopropyl-4-(2-methyl-4-pyridyl)-1H-pyrazolo[3,4-b]pyridine-5-carbaldehyde $^1$H-NMR (CDCl$_3$) δ 1.39 (6H, d, J=7 Hz), 1.59 (3H, t, J=7 Hz), 2.69 (3H, s), 4.09-4.19 (1H, m), 4.63 (2H, q, J=7 Hz), 7.20 (1H, dd, J=4, 1 Hz), 7.24 (1H, d, J=1 Hz), 7.79 (1H, s), 8.70 (1H, d, J=4 Hz), 10.12 (1H, s)

MS (ESI$^+$) m/z 309 (M+1)

EXAMPLE 118

1-Ethyl-6-(isopropoxymethyl)-4-(5-methyl-3-pyridyl)-1H-pyrazolo[3,4-b]pyridine-5-carbaldehyde $^1$H-NMR (CDCl$_3$) δ 1.28 (6H, d, J=7 Hz), 1.57 (3H, t, J=7 Hz), 2.47 (3H, 2), 3.86 (1H, sep, J=7 Hz), 4.65 (2H, q, J=7 Hz), 5.08 (2H, s), 7.60 (1H, s), 7.87 (1H, s), 8.55 (1H, d, J=1 Hz), 8.63 (1H, d, J=1 Hz), 10.19 (1H, s)

MS (ESI$^+$) m/z 339 (M+1)

EXAMPLE 119

4-(5-Chloro-3-pyridyl)-1-ethyl-6-isopropyl-1H-pyrazolo[3,4-b]pyridine-5-carbaldehyde ¹H-NMR (CDCl₃) δ 1.40 (6H, d, J=7 Hz), 1.58 (3H, t, J=7 Hz), 4.09 (1H, sep, J=7 Hz), 4.64 (2H, q, J=7 Hz), 7.79 (1H, t, J=1 Hz), 7.80 (1H, s), 8.60 (1H, d, J=1 Hz), 8.75 (1H, d, J=1 Hz), 10.21 (1H, s)

EXAMPLE 120

4-(4-Amino-3,5-dichlorophenyl)-6-cyclopropyl-1-ethyl-1H-pyrazolo[3,4-b]pyridine-5-carbaldehyde ¹H-NMR (CDCl₃) δ 1.11 (2H, m), 1.31 (2H, m), 1.51 (3H, t, J=7.3 Hz), 3.41 (1H, m), 4.51 (2H, q, J=7.3 Hz), 4.77 (2H, br s), 7.34 (2H, s), 7.85 (1H, s), 10.15 (1H, s).

EXAMPLE 121

6-(Cyclopropylmethyl)-1-ethyl-4-(5-methyl-3-pyridyl)-1H-pyrazolo[3,4-b]pyridine-5-carbaldehyde ¹H-NMR (CDCl₃) δ 0.34-0.38 (2H, m), 0.48-0.54 (2H, m), 1.28-1.39 (1H, m), 1.59 (3H, t, J=7 Hz), 2.47 (3H, s), 3.27 (2H, d, J=7 Hz), 4.63 (2H, q, J=7Hz), 7.61 (1H, s), 7.84 (1H, s), 8.58 (1H, d, J=1 Hz), 8.65 (1H, d, J=1 Hz), 10.14 (1H, s)
MS (ESI⁺) m/z 321 (M+1)

EXAMPLE 122

6-(Ethoxymethyl)-1-ethyl-4-(5-methyl-3-pyridyl)-1H-pyrazolo [3,4-b]pyridine-5-carbaldehyde ¹H-NMR (CDCl₃) δ 1.31 (3H, t, J=7 Hz), 1.57 (3H, t, J=7 Hz), 2.47 (3H, s), 3.74 (2H, q, J=7 Hz), 4.65 (2H, q, J=7 Hz), 5.09 (2H, s), 7.61 (1H, s), 7.88 (1H, s), 8.55 (1H, d, J=1 Hz), 8.63 (1H, d, J=1 Hz), 10.16 (1H, s)
MS (ESI⁺) m/z 325 (M+1)

EXAMPLE 123

4-(5-Bromo-3-pyridyl)-1-ethyl-6-phenyl-1H-pyrazolo[3,4-b]pyridine-5-carbaldehyde ¹H-NMR (CDCl₃) δ 1.59 (3H, t, J=6.6 Hz), 4.66 (2H, q, J=6.6 Hz), 7.53-7.58 (3H, m), 7.62-7.68 (2H, m), 7.89 (1H, s), 7.97 (1H, s), 8.61 (1H, s), 8.81 (1H, s), 10.14 (1H, s)

EXAMPLE 124

A mixture of [4-(6-chloro-3-pyridyl)-1-ethyl-6-phenyl-1H-pyrazolo[3,4-b]pyridin-5-yl]methanol (730 mg), 4-methylmorpholine N-oxide (352 mg) in DCM (20 ml) was added tetrapropylammonium perrutenate (70.3 mg) at room temperature and the mixture was stirred at room temperature for 3 hours. The reaction mixture was filtered through celite pad. The filtrate was washed with saturated aqueous ammonium chloride, saturated aqueous NaHCO₃, water, brine, dried over anhydrous MgSO₄ and concentrated in vacuo. The residue was purified by flash column chromatography on silica gel eluting with a mixture of MeOH and CHCl₃ (1:10) to give 4-(6-chloro-3-pyridyl)-1-ethyl-6-phenyl-1H-pyrazolo[3,4-b]pyridine-5-carbaldehyde (660 mg) as a yellow oil.

¹H-NMR (CDCl₃) δ 1.59 (3H, t, J=7 Hz), 4.67 (2H, q, J=7 Hz), 7.50 (1H, d, J=7 Hz), 7.54-5.79 (3H, m), 7.64-7.68 (2H, m), 7.83 (1H, dd, J=7, 1 Hz), 7.89 (1H, s), 8.50 (1H, d, J=1 Hz), 9.98 (1H, s)

The following compound(s) was(were) obtained in a similar manner to that of Example 124.

EXAMPLE 125

4-(5-Chloro-2-thienyl)-6-cyclopropyl-1-ethyl-1H-pyrazolo[3,4-b]pyridine-5-carbaldehyde ¹H-NMR (CDCl₃) δ 1.09-1.16 (2H, m), 1.25-1.35 (2H, m), 1.51 (3H, t, J=7 Hz), 3.26-3.37 (1H, m), 4.50 (2H, q, J=7 Hz), 7.05 (1H, d, J=4 Hz), 7.10 (1H, d, J=4 Hz), 8.09 (1H, s), 10.30 (1H, s)

EXAMPLE 126

6-Cyclopentyl-1-ethyl-4-(5-methyl-3-pyridyl)-1H-pyrazolo[3,4-b]pyridine-5-carbaldehyde ¹H-NMR (CDCl₃) δ 1.56 (3H, t, J=7 Hz), 1.70-1.84 (2H, m), 1.86-1.97 (2H, m), 2.03-2.18 (4H, m), 2.46 (3H, s), 4.21 (1H, tt, J=7, 7 Hz), 4.60 (2H, q, J=7 Hz), 7.59 (1H, s), 7.81 (1H, s), 8.55 (1H, d, J=2 Hz), 8.61 (1H, d, J=2 Hz), 10.14 (1H, s)

EXAMPLE 127

4-(2-Chloro-4-pyridyl)-1-ethyl-6-phenyl-1H-pyrazolo[3,4-b]pyridine-5-carbaldehyde ¹H-NMR-(CDCl₃) δ 1.58 (3H, t, J=8 Hz), 4.67 (2H, q, J=8 Hz), 7.28 (1H, d, J=5 Hz), 7.54-7.69 (5H, m), 7.83 (1H, s), 8.55 (1H, d, J=5 Hz), 9.99 (1H, s)

EXAMPLE 128

1-Ethyl-6-phenyl-4-(3-pyridyl)-1H-pyrazolo[3,4-b]pyridine-5-carbaldehyde

¹H-NMR (CDCl₃) δ 1.60 (3H, t, J=8 Hz), 4.67 (2H, q, J=8 Hz), 7.48 (1H, dd, J=8, 5 Hz), 7.51-7.60 (3H, m), 7.64-7.70 (2H, m), 7.85 (1H, dt, J=8, 1 Hz), 7.98 (1H, s), 8.70-8.80 (2H, m), 9.99 (1H, s)

EXAMPLE 129

4-(Cyclohexylmethyl)-1-ethyl-6-phenyl-1H-pyrazolo[3,4-b]pyridine-5-carbaldehyde

¹H-NMR (CDCl₃) δ 1.14-1.21 (5H, m), 1.56 (3H, t, J=7 Hz), 1.63-1.76 (6H, m), 3.25 (2H, d, J=7 Hz), 4.61 (2H, q, J=7 Hz), 7.51-7.55 (3H, m), 7.59-7.63 (2H, m), 8.10 (1H, s), 10.00 (1H, s)

EXAMPLE 130

4-(5-Chloro-2-thienyl)-1-ethyl-6-phenyl-1H-pyrazolo[3,4-b]pyridine-5-carbaldehyde ¹H-NMR (CDCl₃) δ 1.58 (3H, t, J=8 Hz), 4.65 (2H, q, J=8 Hz), 7.06 (1H, d, J=5 Hz), 7.23 (1H, d, J=5 Hz), 7.49-7.65 (5H, m), 8.18 (1H, s), 10.06 (1H, s)

EXAMPLE 131

1-Ethyl-6-isopropyl-4-(5-methyl-3-pyridyl)-1H-pyrazolo[3,4-b]pyridine-5-carbaldehyde $^1$H-NMR (CDCl$_3$) δ 1.37 (6H, d, J=7 Hz), 1.57 (3H, t, J=7 Hz), 2.47 (3H, s), 4.14 (1H, sep, J=7 Hz), 4.63 (2H, q, J=7 Hz), 7.59 (1H, s), 7.83 (1H, s), 8.57 (1H, d, J=1 Hz), 8.68 (1H, d, J=1 Hz), 10.12 (1H, s)

EXAMPLE 132

1-Ethyl-4,6-diphenyl-1H-pyrazolo[3,4-b]pyridine-5-carbaldehyde $^1$H-NMR (CDCl$_3$) δ 1.58 (3H, t, J=8 Hz), 4.65 (2H, q, J=8 Hz), 7.46-7.65 (9H, m), 7.91 (1H, s), 10.04 (1H, s)

EXAMPLE 133

4-(5-Chloro-3-pyridyl)-1-ethyl-6-phenyl-1H-pyrazolo[3,4-b]pyridine-5-carbaldehyde $^1$H-NMR (CDCl$_3$) δ 1.58 (3H, t, J=7 Hz), 4.69 (2H, q, J=7 Hz), 7.55-7.58 (3H, m), 7.64-7.68 (2H, m), 7.83 (1H, t, J=1 Hz), 7.88 (1H, s), 8.58 (1H, d, J=1 Hz), 8.73 (1H, d, J=1 Hz), 9.97 (1H, s)

EXAMPLE 134

4-(2-Chloro-4-pyridyl)-1-ethyl-6-isopropyl-1H-pyrazolo[3,4-b]pyridine-5-carbaldehyde $^1$H-NMR (CDCl$_3$) δ 1.40 (6H, d, J=7 Hz), 1.58 (3H, t, J=7 Hz), 4.09 (1H, qq, J=6 Hz), 4.62 (2H, q, J=7 Hz), 7.30 (1H, d, J=6 Hz), 7.42 (1H, s), 7.77 (1H, s), 8.58 (1H, d, J=6 Hz), 10.20 (1H, s)

EXAMPLE 135

6-Cyclopropyl-1-ethyl-4-(5-methyl-3-pyridyl)-1H-pyrazolo[3,4-b]pyridine-5-carbaldehyde $^1$H-NMR (CDCl$_3$) δ 1.14-1.20 (2H, m), 1.34-1.39 (2H, m), 1.53 (3H, t, J=7 Hz), 2.48 (3H, s), 3.33-3.38 (1H, m), 4.54 (2H, q, J=7 Hz), 7.64 (1H, s), 7.78 (1H, s), 8.56 (1H, d, J=1 Hz), 8.63 (1H, d, J=1 Hz), 12.00 (1H, s)
MS (ESI$^+$) m/z 307 (M)

EXAMPLE 136

1-Ethyl-6-phenyl-4-(3-quinolinyl)-1H-pyrazolo[3,4-b]pyridine-5-carbaldehyde $^1$H-NMR (CDCl$_3$) δ 1.53 (3H, t, J=6.7 Hz), 4.70 (2H, q, J=6.7 Hz), 7.52-7.78 (6H, m), 7.82 (1H, dd, J=7.7, 7.7 Hz), 7.89-8.00 (2H, m), 8.23 (1H, d, J=7.7 Hz), 8.30 (1H, s), 9.00 (1H, s), 10.03 (1H, s)

EXAMPLE 137

1-Ethyl-6-isobutyl-4-(5-methyl-3-pyridyl)-1H-pyrazolo[3,4-b]pyridine-5-carbaldehyde $^1$H-NMR (CDCl$_3$) δ 1.02 (6H, d, J=7 Hz), 1.57 (3H, t, J=7 Hz), 2.24 (1H, sep, J=7 Hz), 2.48 (3H, s), 3.23 (2H, d, J=7 Hz), 4.63 (2H, q, J=7 Hz), 7.62 (1H, s), 7.84 (1H, s), 8.55 (1H, s), 8.64 (1H, s), 10.14 (1H, s)

EXAMPLE 138

4-(5-Bromo-3-pyridyl)-1-ethyl-6-isopropyl-1H-pyrazolo[3,4-b]pyridine-5-carbaldehyde $^1$H-NMR (CDCl$_3$) δ 1.40 (6H, d, J=7 Hz), 1.58 (3H, t, J=8 Hz), 4.09 (1H, m), 4.63 (2H, q, J=8 Hz), 7.81 (1H, s), 7.94 (1H, br s), 8.62 (1H, d, J=1 Hz), 8.84 (1H, d, J=1 Hz), 10.21 (1H, s)

EXAMPLE 139

4-(3-Chlorophenyl)-1-ethyl-6-(methoxymethyl)-1H-pyrazolo[3,4-b]pyridine-5-carbaldehyde $^1$H-NMR (CDCl$_3$) δ 1.58 (3H, t, J=8 Hz), 3.59 (3H, s), 4.66 (2H, q, J=8 Hz), 5.07 (2H, s), 7.36 (1H, dt, J=7, 1 Hz), 7.46-7.58 (3H, m), 7.89 (1H, s), 10.09 (1H, s)

EXAMPLE 140

4-(5-Chloro-3-pyridyl)-1-ethyl-6-(methoxymethyl)-1H-pyrazolo[3,4-b]pyridine-5-carbaldehyde $^1$H-NMR (CDCl$_3$) δ 1.59 (3H, t, J=8 Hz), 3.57 (3H, s), 4.67 (2H, q, J=8 Hz), 5.05 (2H, s), 7.81 (1H, t, J=1 Hz), 7.88 (1H, s), 8.59 (1H, d, J=1 Hz), 8.75 (1H, d, J=1 Hz), 10.21 (1H, s)

EXAMPLE 141

4-Cyclohexyl-6-cyclopropyl-1-ethyl-1H-pyrazolo[3,4-b]pyridine-5-carbaldehyde $^1$H-NMR (CDCl$_3$) δ 1.08 (2H, m), 1.29 (2H, m), 1.40-1.51 (3H, m), 1.49 (3H, t, J=7.3 Hz), 1.83-1.93 (7H, m), 2.68 (1H, m), 3.67 (1H, m), 4.47 (2H, q, J=7.3 Hz), 8.20 (1H, s), 10.87 (1H, s)

EXAMPLE 142

1-Ethyl-6-(5-methyl-3-isoxazolyl)-4-(5-methyl-3-pyridyl)-1H-pyrazolo[3,4-b]pyridine-5-carbaldehyde $^1$H-NMR (CDCl$_3$) δ 1.60 (3H, t, J=7 Hz), 2.46 (3H, s), 2.58 (3H, s), 4.67 (2H, q, J=7 Hz), 6.65 (1H, s), 7.62 (1H, s), 7.91 (1H, s), 8.50 (1H, s), 8.58 (1H, s), 10.40 (1H, s)

The following compound(s) was(were) obtained in a similar manner to that of Example 48.

EXAMPLE 143

Ethyl (2E)-3-[6-cyclohexyl-1-ethyl-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 1.37-1.46 (4H, m), 1.57 (3H, t, J=7 Hz), 1.75-1.93 (6H, m), 2.41 (3H, s), 2.99-3.10 (1H, m), 4.19 (2H, q, J=7Hz), 4.60 (2H, q, J=7Hz), 5.64 (1H, d, J=15 Hz), 7.54 (1H, s), 7.73 (1H, s), 7.87 (1H, d, J=15 Hz), 8.47 (1H, d, J=1 Hz), 8.52 (1H, d, J=1 Hz)

EXAMPLE 144

Ethyl (2E)-3-(1-ethyl-4,6-diphenyl-1H-pyrazolo[3,4-b]pyridin-5-yl)acrylate $^1$H-NMR (CDCl$_3$) δ 1.17 (3H, t, J=8 Hz), 1.57 (3H, t, J=8 Hz), 4.06 (2H, q, J=8 Hz), 4.63 (2H, q, J=9 Hz), 5.40 (1H, d, J=15 Hz), 7.40-7.69 (10H, m), 7.81 (1H, s)

EXAMPLE 145

Ethyl (2E)-3-[6-(ethoxymethyl)-1-ethyl-4-(5-methyl-3-pyridyl)-1H-pyrazolo[3,4-b]pyridin-5-yl]acrylate $^1$H-NMR (CDCl$_3$) δ 1.29 (3H, t, J=7 Hz), 1.36 (3H, t, J=7 Hz), 1.55 (3H, t, J=7 Hz), 2.43 (3H, s), 3.73 (2H, q, J=7 Hz), 4.20 (2H, q, J=7 Hz), 4.64 (2H, q, J=7 Hz), 4.75 (2H, s), 6.03 (1H, d, J=15 Hz), 7.57 (1H, s), 7.80 (1H, s), 7.84 (1H, d, J=15 Hz), 8.50 (1H, d, J=1 Hz), 8.55 (1H, d, J=1 Hz)

MS (ESI$^+$) m/z 395 (M+1)

EXAMPLE 146

Ethyl (2E)-3-[1,6-diethyl-4-(5-methyl-3-pyridyl)-1H-pyrazolo[3,4-b]pyridin-5-yl]acrylate $^1$H-NMR (CDCl$_3$) δ 1.25 (3H, t, J=7 Hz), 1.40 (3H, t, J=7 Hz), 1.58 (3H, t, J=7 Hz), 2.44 (3H, s), 3.06 (2H, q, J=7 Hz), 4.19 (2H, q, J=7 Hz), 4.60 (2H, q, J=7 Hz), 5.70 (1H, d, J=13 Hz), 7.52 (1H, s), 7.73 (1H, s), 7.82 (1H, d, J=13 Hz), 8.46 (1H, s), 8.52 (1H, s)

EXAMPLE 147

Ethyl (2E)-3-[1-ethyl-6-(5-ethyl-3-isoxazolyl)-4-(5-methyl-3-pyridyl)-1H-pyrazolo[3,4-b]pyridin-5-yl]acrylate $^1$H-NMR (CDCl$_3$) δ 1.36 (3H, t, J=7 Hz), 1.57 (3H, t, J=7 Hz), 2.45 (3H, s), 2.55 (3H, s), 4.14 (2H, q, J=7 Hz), 4.64 (2H, q, J=7 Hz), 5.54 (1H, d, J=17 Hz), 6.50 (1H, s), 7.56 (1H, s), 7.84 (1H, s), 8.01 (1H, d, J=17 Hz), 8.51 (1H, s), 8.56 (1H, s)

EXAMPLE 148

Ethyl (2E)-3-[4-(4-amino-3,5-dichlorophenyl)-6-cyclopropyl-1-ethyl-1H-pyrazolo[3,4-b]pyridin-5-yl]acrylate $^1$H-NMR (CDCl$_3$) δ 1.08 (2H, m), 1.30 (2H, m), 1.31 (3H, t, J=7.1 Hz), 1.51 (3H, t, J=7.1 Hz), 2.39 (1H, m), 4.24 (2H, q, J=7.1 Hz), 4.50 (2H, q, J=7.2 Hz), 4.67 (2H, br s), 6.12 (1H, d, J=16.1 Hz), 7.28 (2H, s), 7.75 (1H, s), 7.89 (1H, d, J=16.1 Hz)

EXAMPLE 149

Ethyl (2E)-3-[4-(5-bromo-3-pyridyl)-6-cyclopropyl-1-ethyl-1H-pyrazolo[3,4-b]pyridin-5-yl]acrylate $^1$H-NMR (CDCl$_3$) δ 1.10 (2H, m), 1.29 (3H, t, J=7.3 Hz), 1.33 (2H, m), 1.52 (3H, t, J=7.2 Hz), 2.36 (1H, m), 4.21 (2H, q, J=7.1 Hz), 4.52 (2H, q, J=7.2 Hz), 5.96 (1H, d, J=16.2 Hz), 7.70 (1H, s), 7.72 (1H, d, J=16.0 Hz), 7.91 (1H, m), 8.58 (1H, d, J=1.7 Hz), 8.77 (1H, d, J=2.1 Hz)

EXAMPLE 150

Ethyl (2E)-3-[4-(2-chloro-4-pyridyl)-6-cyclopentyl-1-ethyl-1H-pyrazolo[3,4-b]pyridin-5-yl]acrylate $^1$H-NMR (CDCl$_3$) δ 1.28 (3H, t, J=7 Hz), 1.55 (3H, t, J=7 Hz), 1.68-1.78 (2H, m), 1.87-1.95 (2H, m), 1.97-2.08 (4H, m), 3.53 (1H, quintet, J=7 Hz), 4.20 (2H, q, J=7 Hz), 4.58 (2H, q, J=7 Hz), 5.64 (1H, d, J=15 Hz), 7.23 (1H, dd, J=4, 1 Hz), 7.38 (1H, d, J=1 Hz), 7.69 (1H, s), 7.88 (1H, d, J=15 Hz), 8.51 (1H, d, J=4 Hz)

EXAMPLE 151

Ethyl (2E)-3-[1-ethyl-4-(5-ethynyl-3-pyridyl)-6-isopropyl-1H-pyrazolo[3,4-b]pyridin-5-yl]acrylate $^1$H-NMR (CDCl$_3$) δ 1.25 (3H, t, J=6.7 Hz), 1.36 (6H, d, J=6.5 Hz), 1.56 (3H, t, J=6.5 Hz), 3.30 (1H, s), 3.45 (1H, h, J=6.5 Hz), 4.18 (2H, q, J=6.7 Hz), 4.60 (2H, q, J=6.5 Hz), 5.62 (1H, d, J=12.3 Hz), 7.70 (1H, s), 7.82 (1H, s), 7.88 (1H, d, J=12.3 Hz), 8.56 (1H, bs), 8.77 (1H, bs)

EXAMPLE 152

Ethyl (2E)-3-[1-ethyl-6-phenyl-4-(tetrahydro-2H-pyran-4-yl)-1H-pyrazolo[3,4-b]pyridin-5-yl]acrylate $^1$H-NMR (CDCl$_3$) δ 1.28 (3H, t, J=6.7 Hz), 1.55 (3H, t, J=6.8 Hz), 1.77 (2H, d, J=12.3 Hz), 2.28-2.50 (2H, m), 3.43-3.64 (3H, m), 4.10-4.26 (4H, m), 4.60 (2H, q, J=6.7 Hz), 5.75 (1H, d, J=13.4 Hz), 7.38-7.48 (3H, m), 7.48-7.56 (2H, m), 7.83 (1H, d, J=13.4 Hz), 8.30 (1H, s)

EXAMPLE 153

Ethyl (2E)-3-[1-ethyl-6-(1-ethylpropyl)-4-(5-methyl-3-pyridyl)-1H-pyrazolo[3,4-b]pyridin-5-yl]acrylate $^1$H-NMR (CDCl$_3$) δ 0.82 (6H, t, J=7 Hz), 1.27 (3H, t, J=7 Hz), 1.55 (3H, t, J=7 Hz), 1.68-1.82 (2H, m), 1.87-2.00 (2H, m), 2.41 (3H, s), 3.02-3.12 (1H, m), 4.17 (2H, q, J=7 Hz), 4.59 (2H, q, J=7 Hz), 5.58 (1H, d, J=15 Hz), 7.54 (1H, s), 7.73 (1H, s), 7.87 (1H, d, J=15 Hz), 8.48 (1H, d, J=1 Hz), 8.51 (1H, d, J=1 Hz)

EXAMPLE 154

Ethyl (2E)-3-[4-(2-chloro-4-pyridyl)-1-ethyl-6-phenyl-1H-pyrazolo[3,4-b]pyridin-5-yl]acrylate $^1$H-NMR (CDCl$_3$) δ 1.21 (3H, t, J=8 Hz), 1.57 (3H, t, J=8 Hz), 4.11 (2H, q, J=8 Hz), 4.64 (2H, q, J=8 Hz), 5.47 (1H, d, J=15 Hz), 7.30 (1H, br d, J=5 Hz), 7.44-7.64 (6H, m), 7.78 (1H, s), 8.56 (1H, d, J=5 Hz)

EXAMPLE 155

Ethyl (2E)-3-[1-ethyl-6-phenyl-4-(3-pyridyl)-1H-pyrazolo[3,4-b]pyridin-5-yl]acrylate $^1$H-NMR (CDCl$_3$) δ 1.18 (3H, t, J=8 Hz), 1.58 (3H, t, J=8 Hz), 4.07 (2H, q, J=8 Hz), 4.64 (2H, q, J=8 Hz), 7.44-7.52 (4H, m), 7.55-7.67 (3H, m), 7.75-7.84 (2H, m), 8.70-8.78 (2H, m)

EXAMPLE 156

Ethyl (2E)-3-[4-(3-chlorophenyl)-1-ethyl-6-(methoxymethyl)-1H-pyrazolo[3,4-b]pyridin-5-yl]acrylate $^1$H-NMR (CDCl$_3$) δ 1.29 (3H, t, J=8 Hz), 1.57 (3H, t, J=8 Hz), 3.54 (3H, s), 4.20 (2H, q, J=8 Hz), 4.63 (2H, q, J=8 Hz), 4.71 (2H, s), 6.04 (1H, d, J=15 Hz), 7.30 (1H, m), 7.40-7.49 (3H, m), 7.76-7.84 (2H, m)

EXAMPLE 157

Ethyl (2E)-3-[4-(cyclohexylmethyl)-1-ethyl-6-phenyl-1H-pyrazolo[3,4-b]pyridin-5-yl]acrylate $^1$H-NMR (CDCl$_3$) δ 1.10-1.18 (5H, m), 1.26 (3H, t, J=7 Hz), 1.50-1.54 (3H, m), 1.56 (3H, t, J=7 Hz), 1.64-1.73 (3H, m), 2.97 (2H, d, J=7 Hz), 4.18 (2H, q, J=7 Hz), 4.58 (2H, q, J=7 Hz), 5.70 (1H, d, J=15 Hz), 7.40-7.45 (3H, m), 7.53-7.57 (2H, m), 7.84 (1H, d, J=15 Hz), 8.07 (1H, s)

EXAMPLE 158

Ethyl (2E)-3-[4-(6-chloro-3-pyridyl)-1-ethyl-6-phenyl-1H-pyrazolo[3,4-b]pyridin-5-yl]acrylate $^1$H-NMR (CDCl$_3$) δ 1.21 (3H, t, J=7 Hz), 1.56 (3H, t, J=7 Hz), 4.10 (2H, q, J=7 Hz), 4.64 (2H, q, J=7 Hz), 5.45 (1H, d, J=15 Hz), 7.45-7.50 (4H, m), 7.56-7.59(2H, m), 7.60 (1H, d, J=15 Hz), 7.74 (1H, dd, J=7, 1 Hz), 7.80 (1H, s), 8.52 (1H, d, J=1 Hz)

EXAMPLE 159

Ethyl (2E)-3-[4-(5-chloro-2-thienyl)-1-ethyl-6-phenyl-1H-pyrazolo[3,4-b]pyridin-5-yl]acrylate $^1$H-NMR (CDCl$_3$) δ 1.23 (3H, t, J=8 Hz), 1.56 (3H, t, J=8 Hz), 4.14 (2H, q, J=8 Hz), 4.61 (2H, q, J=8 Hz), 5.57 (1H, d, J=15 Hz), 7.04 (1H, d, J=5 Hz), 7.09 (1H, d, J=5 Hz), 7.35-7.58 (5H, m), 7.81 (1H, d, J=15 Hz), 8.09 (1H, s)

EXAMPLE 160

Ethyl (2E)-3-[1-ethyl-6-isopropyl-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 1.37 (6H, d, J=7 Hz), 1.57 (3H, t, J=7 Hz), 2.42 (3H, s), 3.47 (1H, sep, J=7 Hz), 4.19 (2H, q, J=7 Hz), 4.60 (2H, q, J=7 Hz), 5.65 (1H, d, J=15 Hz), 7.53 (1H, s), 7.73 (1H, s), 7.87 (1H, d, J=15 Hz), 8.47 (1H, s), 8.52 (1H, s)

EXAMPLE 161

Ethyl (2E)-3-[4-(5-chloro-3-pyridyl)-1-ethyl-6-phenyl-1H-pyrazolo[3,4-b]pyridin-5-yl]acrylate $^1$H-NMR (CDCl$_3$) δ 1.20 (3H, t, J=7 Hz), 1.58 (3H, t, J=7 Hz), 4.10 (2H, q, J=7 Hz), 4.65 (2H, q, J=7 Hz), 5.43 (1H, d, J=15 Hz), 7.45-7.49 (3H, m), 7.57-7.60 (2H, m), 7.61 (1H, d, J=15 Hz), 7.79 (1H, t, J=1 Hz), 7.81 (1H, s), 8.59 (1H, d, J=1 Hz), 8.71 (1H, d, J=1 Hz)
MS (ESI$^+$) m/z 433 (M+1)

EXAMPLE 162

Ethyl (2E)-3-[6-cyclopropyl-1-ethyl-4-(5-methyl-3-pyridyl)-1H-pyrazolo[3,4-b]pyridin-5-yl]acrylate $^1$H-NMR (CDCl$_3$) δ 1.07-1.13 (2H, m), 1.28 (3H, t, J=7 Hz), 1.33-1.36 (2H, m), 1.52 (3H, t, J=7 Hz), 2.34-2.41 (1H, m), 2.44 (3H, s), 4.19 (2H, q, J=7 Hz), 4.53 (2H, q, J=7 Hz), 5.97 (1H, d, J=15 Hz), 7.57 (1H, s), 7.69 (1H, s), 7.89 (1H, d, J=15 Hz), 8.47 (1H, d, J=1 Hz), 8.54 (1H, d, J=1 Hz)
MS (ESI$^+$) m/z 377 (M+1)

EXAMPLE 163

Ethyl (2E)-3-[1-ethyl-6-isobutyl-4-(5-methyl-3-pyridyl)-1H-pyrazolo[3,4-b]pyridin-5-yl]acrylate $^1$H-NMR (CDCl$_3$) δ 1.00 (6H, d, J=7 Hz), 1.27 (3H, t, J=7 Hz), 1.56 (3H, t, J=7 Hz), 2.31 (1H, sep, J=7Hz), 2.43 (3H, s), 2.90 (2H, d, J,=7Hz), 4.19 (2H, q, J=7 Hz), 4.60 (2H, q, J=7 Hz), 5.63 (1H, d, J=15 Hz), 7.57 (1H, s), 7.74 (1H, s), 7.84 (1H, d, J=15 Hz), 8.49 (1H, s), 8.55 (1H, s)
MS (ESI$^+$) m/z 393 (M+1)

EXAMPLE 164

Ethyl (2E)-3-[4-(2-chloro-4-pyridyl)-1-ethyl-6-isopropyl-1H-pyrazolo[3,4-b]pyridin-5-yl]acrylate $^1$H-NMR (CDCl$_3$) δ 1.38 (3H, t, J=7 Hz), 1.36 (6H, d, J=6 Hz), 1.57 (3H, t, J=7 Hz), 3.45 (1H, qq, J=6, 6 Hz), 4.20 (2H, q, J=7 Hz), 4.60 (2H, q, J=7 Hz), 5.65 (1H, d, J=17 Hz), 7.26 (1H, d, J=5 Hz), 7.39 (1H, s), 7.72 (1H, s), 7.86 (1H, d, J=17 Hz), 8.51 (1H, d, J=5 Hz)

EXAMPLE 165

Ethyl (2E)-3-[6-butyl-1-ethyl-4-(5-methyl-3-pyridyl)-1H-pyrazolo[3,4-b]pyridin-5-yl]acrylate $^1$H-NMR (CDCl$_3$) δ 0.99 (3H, t, J=7 Hz), 1.26 (3H, t, J=7 Hz), 1.48 (2H, tq, J=7.7 Hz), 1.75-1.87 (2H, m), 2.42 (3H, s), 3.02 (2H, t, J=7 Hz), 4.18 (2H, q, J=7 Hz), 4.59 (2H, q, J=7 Hz), 5.66 (1H, d, J=13 Hz), 7.54 (1H, s), 7.72 (1H, s), 7.84 (1H, d, J=13 Hz), 8.46 (1H, s), 8.53 (1H, s)

EXAMPLE 166

Ethyl (2E)-3-[1-ethyl-4-(5-methoxy-3-pyridyl)-6-phenyl-1H-pyrazolo[3,4-b]pyridin-5-yl]acrylate $^1$H-NMR (CDCl$_3$) δ 1.20 (3H, t, J=7 Hz), 1.59 (3H, t, J=7 Hz), 3.91 (3H, s), 4.09 (2H, q, J=7 Hz), 4.64 (2H, q, J=7 Hz), 5.45 (1H, d, J=15 Hz), 7.30 (1H, s), 7.45-7.48 (3H, m), 7.57-7.60 (2H, m), 7.62 (1H, d, J=15 Hz), 7.84 (1H, s), 8.33 (1H, d, J=1 Hz), 8.44 (1H, d, J=1 Hz)

EXAMPLE 167

Ethyl (2E)-3-[1-ethyl-6-(4-fluorophenyl)-4-(5-methyl-3-pyridyl)-1H-pyrazolo[3,4-b]pyridin-5-yl]acrylate $^1$H-NMR (CDCl$_3$) δ 1.20 (3H, t, J=7 Hz), 1.32 (3H, t, J=7 Hz), 2.43 (3H, s), 4.14 (2H, q, J=7 Hz), 4.53 (2H, q, J=7 Hz), 5.43 (1H, d, J=12 Hz), 7.17 (2H, dd, J=7,7 Hz), 7.56-7.66 (3H, m), 7.80 (1H, s), 8.54 (2H, br)

EXAMPLE 168

Ethyl (2E)-3-[4-(5-chloro-2-thienyl)-1-ethyl-6-isopropyl-1H-pyrazolo[3,4-b]pyridin-5-yl]acrylate $^1$H-NMR (CDCl$_3$) δ 1.33 (6H, d, J=7 Hz), 1.35 (3H, t, J=7 Hz), 1.54 (3H, t, J=7 Hz), 3.49 (1H, sep, J=7 Hz), 4.27 (2H, q, J=7 Hz), 4.59 (2H, q, J=7 Hz), 5.99 (1H, d, J=15 Hz), 6.99 (1H, d, J=1 Hz), 7.05 (1H, d, J=1 Hz), 7.92 (1H, d, J=15 Hz), 7.99 (1H, s)

EXAMPLE 169

Ethyl (2E)-3-[1-ethyl-6-phenyl-4-(3-quinolinyl)-1H-pyrazolo[3,4-b]pyridin-5-yl]acrylate $^1$H-NMR (CDCl$_3$) δ 1.11 (3H, t, J=6.7 Hz), 1.60 (3H, t, J=6.7 Hz), 4.04 (2H, q, J=6.7 Hz), 4.66 (2H, q, J=6.7 Hz), 5.45 (1H, d, J=12.3 Hz), 7.45-7.54 (3H, m), 7.59-7.71 (5H, m), 7.80-7.90 (2H, m), 8.21 (1H, d, J=7.6 Hz), 8.33 (1H, s), 8.94 (1H, s)

EXAMPLE 170

Ethyl (2E)-3-[4-(5-bromo-3-pyridyl)-1-ethyl-6-isopropyl-1H-pyrazolo[3,4-b]pyridin-5-yl]acrylate $^1$H-NMR (CDCl$_3$) δ 1.29 (3H, t, J=8 Hz), 1.36 (6H, d, J=7 Hz), 1.57 (3H, t, J=8 Hz), 3.45 (1H, m), 4.19 (2H, q, J=8 Hz), 4.61 (2H, q, J=8 Hz), 5.65 (1H, d, J=15 Hz), 7.73 (1H, s), 7.86 (1H, d, J=15 Hz), 7.89 (1H, br s), 8.56 (1H, d, J=1 Hz), 8.74 (1H, d, J=1 Hz)

EXAMPLE 171

Ethyl (2E)-3-[4-(2-chloro-4-pyridyl)-6-cyclopropyl-1-ethyl-1H-pyrazolo[3,4-b]pyridin-5-yl]acrylate $^1$H-NMR (CDCl$_3$) δ 1.08-1.15 (2H, m), 1.30 (3H, t, J=6.5 Hz), 1.28-1.36 (2H, m), 1.52 (3H, t, J=6.7 Hz), 2.30-2.40 (1H, m), 4.20 (2H, q, J=6.5 Hz), 4.53 (2H, q, J=6.7 Hz), 5.94 (1H, d, J=12.8 Hz), 7.25 (1H, d, J=4.8 Hz), 7.4 (1H, s), 7.69 (1H, s), 7.89 (1H, d, J=12.8 Hz), 8.53 (1H, d, J=4.8 Hz)

EXAMPLE 172

Ethyl (2E)-3-[4-(5-bromo-3-pyridyl)-6-cyclopentyl-1-ethyl-1H-pyrazolo[3,4-b]pyridin-5-yl]acrylate $^1$H-NMR (CDCl$_3$) δ 1.28 (3H, t, J=6.7 Hz), 1.56 (3H, t, J=7.1 Hz), 1.66-1.80 (2H, m), 1.86-1.96 (2H, m), 2.00-2.09 (4H, m), 3.54 (1H, tt, J=7.2, 7.2 Hz), 4.19 (2H, q, J=6.7 Hz), 4.59 (2H, q, J=6.7 Hz), 5.65 (1H, d, J=13.2 Hz), 7.72 (1H, s), 7.86 (1H, d, J=13.2 Hz), 7.88 (1H, s), 8.56 (1H, d, J=1 Hz), 8.75 (1H, s)

EXAMPLE 173

Ethyl (2E)-3-[4-(5-bromo-3-pyridyl)-1-ethyl-6-(methoxymethyl)-1H-pyrazolo[3,4-b]pyridin-5-yl]acrylate $^1$H-NMR (CDCl$_3$) δ 1.30 (3H, t, J=7 Hz), 1.57 (3H, t, J=7 Hz), 3.54 (3H, s), 4.22 (2H, q, J=7 Hz), 4.64 (2H, q, J=7 Hz), 4.71 (2H, s), 6.02 (1H, d, J=15 Hz), 7.81 (1H, d, J=15Hz), 7.82 (1H, s), 7.93 (1H, t, J=1 Hz), 8.62 (1H, d, J=1 Hz), 8.80 (1H, d, J=1 Hz)

MS (ESI$^+$) m/z 447 (M+2)

EXAMPLE 174

Ethyl (2E)-3-[1-ethyl-4-(5-methyl-3-pyridyl)-6-propyl-1H-pyrazolo[3,4-b]pyridin-5-yl]acrylate $^1$H-NMR (CDCl$_3$) δ 1.04 (3H, t, J=7 Hz), 1.26 (3H, t, J=7 Hz), 1.56 (3H, t, J=6 Hz), 1.86 (2H, tq, J=7,7 Hz), 2.42 (3H, s), 2.99 (2H, t, J=7 Hz), 4.17 (2H, q, J=7 Hz), 4.59 (2H, q, J=6 Hz), 5.67 (1H, d, J=13 Hz), 7.53 (1H, s), 7.72 (1H, s), 7.82 (1H, d, J=13 Hz), 8.45 (1H, s), 8.52 (1H, s)

EXAMPLE 175

Ethyl (2E)-3-[4-(5-chloro-3-pyridyl)-1-ethyl-6-isopropyl-1H-pyrazolo[3,4-b]pyridin-5-yl]acrylate $^1$H-NMR (CDCl$_3$) δ 1.28 (3H, t, J=7 Hz), 1.37 (6H, d, J=7 Hz), 1.57 (3H, t, J=7 Hz), 3.45 (1H, sep, J=7 Hz), 4.19 (2H, q, J=7 Hz), 4.62 (2H, q, J=7 Hz), 5.64 (1H, d, J=15 Hz), 7.72 (1H, s), 7.73 (1H, t, J=1 Hz), 7.87 (1H, d, J=15Hz), 8.53 (1H, d, J=1 Hz), 8.66 (1H, d, J=1 Hz)

EXAMPLE 176

Ethyl (2E)-3-[6-cyclobutyl-1-ethyl-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 1.59 (3H, t, J=7 Hz), 1.92-1.97 (1H, m), 2.06-2.14 (1H, m), 2.30-2.40 (2H, m), 2.41 (3H, s), 2.57-2.65 (2H, m), 3.99 (1H, quintet, J=7 Hz), 4.17 (2H, q, J=7 Hz), 4.66 (2H, q, J=7 Hz), 5.63 (1H, d, J=15Hz), 7.53 (1H, d, J=1 Hz), 7.73 (1H, s), 7.76 (1H, d, J=15 Hz), 8.45 (1H, d, J=1 Hz), 8.53 (1H, d, J=1 Hz)

MS (ESI$^+$) m/z 391 (M+1)

EXAMPLE 177

Ethyl (2E)-3-[4-(5-chloro-3-pyridyl)-6-cyclopropyl-1-ethyl-1H-pyrazolo[3,4-b]pyridin-5-yl]acrylate $^1$H-NMR (CDCl$_3$) δ 1.07-1.14 (2H, m), 1.29 (3H, t, J=7 Hz), 1.30-1.35 (2H, m), 1.52 (3H, t, J=7 Hz), 2.33-2.42 (1H, m), 4.20 (2H, q, J=7 Hz), 4.52 (2H, q, J=7 Hz), 5.96 (1H, d, J=13 Hz), 7.70 (1H, s), 7.74 (1H, s), 7.88 (1H, d, J=13 Hz), 8.53 (1H, s), 8.67 (1H, s)

EXAMPLE 178

Ethyl (2E)-3-[4-(5-chloro-3-pyridyl)-1-ethyl-6-(methoxymethyl)-1H-pyrazolo[3,4-b]pyridin-5-yl]acrylate $^1$H-NMR (CDCl$_3$) δ 1.30 (3H, t, J=8 Hz), 1.58 (3H, t, J=8 Hz), 3.54 (3H, s), 4.21 (2H, q, J=8 Hz), 4.64 (2H, q, J=8 Hz), 4.72 (2H, s), 6.00 (1H, d, J=15 Hz), 7.79-7.85 (3H, m), 8.56 (1H, d, J=1 Hz), 8.69 (1H, d, J=1 Hz)

EXAMPLE 179

Ethyl (2E)-3-(1-ethyl-4-isopropyl-6-phenyl-1H-pyrazolo[3,4-b]pyridin-5-yl)acrylate $^1$H-NMR (CDCl$_3$) δ 1.26 (3H, t, J=6.5 Hz), 1.53 (3H, t, J=6.7 Hz), 1.58 (6H, d, J=6.7 Hz), 3.60 (1H, h, J=6.7 Hz), 4.18 (2H, q, J=6.5 Hz), 4.58 (2H, q, J=6.7 Hz), 5.75 (1H, d, J=12.0 Hz), 7.38-7.45 (3H, m), 7.49-7.55 (2H, m), 7.80 (1H, d, J=12.0 Hz), 8.30 (1H, s)

EXAMPLE 180

Ethyl (2E)-3-[6-(cyclopropylmethyl)-1-ethyl-4-(5-methyl-3-pyridyl)-1H-pyrazolo[3,4-b]pyridin-5-yl]acrylate $^1$H-NMR (CDCl$_3$) δ 0.30-0.35 (2H, m), 0.50-0.57 (2H, m), 1.27 (3H, t, J=7 Hz), 1.57 (3H, t, J=7 Hz), 2.42 (3H, s), 2.97 (2H, d, J=7 Hz), 4.18 (2H, q, J=7 Hz), 4.60 (2H, q, J=7 Hz), 5.68 (1H, d, J=15 Hz), 7.56 (1H, s), 7.75 (1H, s), 7.87 (1H, d, J=15 Hz), 8.50 (1H, d, J=1 Hz), 8.54 (1H, d, J=1 Hz)

EXAMPLE 181

Ethyl (2E)-3-(4-cyclohexyl-6-cyclopropyl-1-ethyl-1H-pyrazolo[3,4-b]pyridin-5-yl)acrylate $^1$H-NMR (CDCl$_3$) δ 0.98 (2H, m), 1.21 (2H, m), 1.35-1.51 (3H, m), 1.38 (3H, t, J=7.2 Hz), 1.48 (3H, t, J=7.3 Hz), 1.81-1.91 (7H, m), 2.20 (1H, m), 3.04 (1H, m), 4.31 (2H, q, J=7.1 Hz), 4.46 (2H, q, J=7.2 Hz), 6.08 (1H, d, J=16.1 Hz), 8.08 (1H, s), 8.09 (1H, d, J=16.1 Hz)

EXAMPLE 182

Ethyl (2E)-3-[6-(2,2-dimethylpropyl)-1-ethyl-4-(5-methyl-3-pyridyl)-1H-pyrazolo[3,4-b]pyridin-5-yl]acrylate $^1$H-NMR (CDCl$_3$) δ 1.05 (9H, s), 1.26 (3H, t, J=7 Hz), 1.56 (3H, t, J=7 Hz), 2.42 (3H, s), 2.97 (2H, s), 4.17 (2H, q, J=7 Hz), 4.59 (2H, q, J=7 Hz), 5.54 (1H, d, J=15 Hz), 7.53 (1H, s), 7.72 (1H, s), 7.90 (1H, d, J=15 Hz), 8.46 (1H, s), 8.53 (1H, s)

EXAMPLE 183

Ethyl (2E)-3-[6-cyclopentyl-1-ethyl-4-(5-methyl-3-pyridyl)-1H-pyrazolo[3,4-b]pyridin-5-yl]acrylate $^1$H-NMR (CDCl$_3$) δ 1.29 (3H, t, J=7 Hz), 1.56 (3H, t, J=7 Hz), 1.78-1.79 (2H, m), 1.86-2.04 (2H, m), 2.05-2.10 (4H, m), 2.42 (3H, s), 3.56 (1H, tt, J=7, 7 Hz), 4.17 (2H, q, J=7 Hz), 4.59 (2H, q, J=7 Hz), 5.65 (1H, d, J=17 Hz), 7.54 (1H, s), 7.71 (1H, s), 7.89 (1H, d, J=17 Hz), 8.46 (1H, d, J=2 Hz), 8.52 (1H, d, J=2 Hz)

EXAMPLE 184

Ethyl (2E)-3-[1-ethyl-6-(isopropoxymethyl)-4-(5-methyl-3-pyridyl)-1H-pyrazolo[3,4-b]pyridin-5-yl]acrylate $^1$H-NMR (CDCl$_3$) δ 1.27 (3H, t, J=7 Hz), 1.30 (6H, d, J=7 Hz), 1.56 (3H, t, J=7 Hz), 2.43 (3H, s), 3.85 (1H, sep, J=7 Hz), 4.19 (2H, q, J=7 Hz), 4.62 (2H, q, J=7 Hz), 4.74 (2H, s), 5.98 (1H, d, J=15 Hz), 7.57 (1H, s), 7.78 (1H, s), 7.89 (1H, d, J=15 Hz), 8.50 (1H, d, J=1 Hz), 8.55 (1H, d, J=1 Hz)

EXAMPLE 185

Ethyl (2E)-3-[1-ethyl-6-isopropyl-4-(2-methyl-4-pyridyl)-1H-pyrazolo[3,4-b]pyridin-5-yl]acrylate $^1$H-NMR (CDCl$_3$) δ 1.27 (3H, t, J=7 Hz), 1.36 (6H, d, J=7 Hz), 1.56 (3H, t, J=7 Hz), 2.63 (3H, s), 3.45 (1H, sep, J=7 Hz), 4.19 (2H, q, J=7 Hz), 4.60 (2H, q, J=7 Hz), 5.65 (1H, d, J=15 Hz), 7.13 (1H, dd, J=4, 1 Hz), 7.19 (1H, d, J=1 Hz), 7.69 (1H, s), 7.87 (1H, d, J=15 Hz), 8.63 (1H, d, J=4 Hz)

MS (ESI$^+$) m/z 379 (M+1)

EXAMPLE 186

Ethyl (2E)-3-(4-cyclohexyl-1-ethyl-6-phenyl-1H-pyrazolo[3,4-b]pyridin-5-yl)acrylate $^1$H-NMR (CDCl$_3$) δ 1.28 (3H, t, J=6.6 Hz), 1.38-1.52 (2H, m), 1.53 (3H, t, J=6.6 Hz), 1.82-2.09 (8H, m), 3.15-3.28 (1H, m), 4.19 (2H, q, J=6.6 Hz), 4.57 (2H, q, J=6.6 Hz), 5.73 (1H, d, J=12.1 Hz), 7.37-7.45 (3H, m), 7.48-7.53 (2H, m), 7.81 (1H, d, J=12.1 Hz), 8.24 (1H, s)

EXAMPLE 187

Ethyl (2E)-3-[4-(5-chloro-2-thienyl)-6-cyclopropyl-1-ethyl-1H-pyrazolo[3,4-b]pyridin-5-yl]acrylate $^1$H-NMR (CDCl$_3$) δ 1.04-1.10 (2H, m), 1.25-1.34 (2H, m), 1.35 (3H, t, J=7 Hz), 1.51 (3H, t, J=7 Hz), 2.36-2.46 (1H, m), 4.26 (2H, q, J=7 Hz), 4.50 (2H, q, J=7 Hz), 6.30 (1H, d, J=17 Hz), 7.03 (1H, d, J=4 Hz), 7.07 (1H, d, J=4 Hz), 8.00 (1H, s), 8.01 (1H, d, J=17 Hz)

EXAMPLE 188

Ethyl (2E)-3-[1-ethyl-6-(2-fluorophenyl)-4-(-methyl-3-pyridyl)-1H-pyrazolo[3,4-b]pyridin-5-yl]acrylate $^1$H-NMR (CDCl$_3$) δ 1.27 (3H, t, J=6.7 Hz), 1.56 (3H, t, J=6.7 Hz), 2.45 (3H, s), 4.06 (2H, q, J=6.7 Hz), 4.62 (2H, q, J=6.7 Hz), 5.48 (1H, d, J=12.4 Hz), 7.13 (1H, dd, J=7.7, 7.7 Hz), 7.30 (1H, dd, J=7.7, 7.7 Hz), 7.42-7.64 (4H, m), 7.74 (1H, s), 8.46-8.70 (2H, br)

EXAMPLE 189 ethyl (2E)-3-[4-(5-bromo-3-pyridyl)-1-ethyl-6-phenyl-1H-pyrazolo[3,4-b]pyridin-5-yl]acrylate $^1$H-NMR (CDCl$_3$) δ 1.21 (3H, t, J=6.5 Hz), 1.58 (3H, t, J=6.9 Hz), 4.10 (2H, q, J=6.5 Hz), 4.63 (2H, q, J=6.9 Hz), 5.45 (1H, d, J=12.6 Hz), 7.42-7.54 (3H, m), 7.55-7.62 (2H, m), 7.62 (1H, s), 7.81 (1H, s), 7.95 (1H, s), 8.62 (1H, s), 8.80 (1H, s)

The following compound(s) was(were) obtained in a similar manner to that of Example 82.

EXAMPLE 190

(2E)-3-[6-Cyclohexyl-1-ethyl-4-(5-methyl-3-pyridyl)-1H-pyrazolo[3,4-b]pyridin-5-yl]acrylic acid $^1$H-NMR (CDCl$_3$) δ 1.25-1.48 (4H, m), 1.57 (3H, t, J=7 Hz), 1.70-1.90 (6H, m), 2.46 (3H, s), 3.02-3.13 (1H, m), 4.60 (2H, q, J=7Hz), 5.67 (1H, d, J=15 Hz), 7.70 (1H, s), 7.77 (1H, s), 7.93 (1H, d, J=15 Hz), 8.50 (1H, d, J=1 Hz), 8.51 (1H, d, J=1 Hz)

mp. 255-257° C.

EXAMPLE 191

(2E)-3-[4-(3-Chlorophenyl)-1-ethyl-6-(methoxymethyl)-1H-pyrazolo[3,4-b]pyridin-5-yl]acrylic acid $^1$H-NMR (CDCl$_3$) δ 1.57 (3H, t, J=8 Hz), 3.54 (2H, s), 4.63 (2H, q, J=8 Hz), 4.72 (2H, s), 6.04 (1H, d, J=15 Hz), 7.28 (1H, m), 7.40-7.51 (3H, m), 7.81 (1H, s), 7.91 (1H, d, J=15 Hz) mp 234-235° C.

EXAMPLE 192

(2E)-3-(4-Cyclohexyl-1-ethyl-6-phenyl-1H-pyrazolo[3,4-b]pyridin-5-yl)acrylic acid $^1$H-NMR (CDCl$_3$) δ 1.37-1.54 (4H, m), 1.55 (3H, t, J=6.7 Hz), 1.80-2.09 (6H, m), 3.13-3.26 (1H, m), 4.57 (2H, q, J=6.7 Hz), 5.75 (1H, d, J=12.2 Hz), 7.36-7.55 (5H, m), 7.92 (2H, d, J=12.2 Hz), 8.25 (1H, s)

EXAMPLE 193

(2E)-3-[6-Cyclopentyl-1-ethyl-4-(5-methyl-3-pyridyl)-1H-pyrazolo[3,4-b]pyridin-5-yl]acrylic acid $^1$H-NMR (CDCl$_3$) δ 1.56 (3H, t, J=7 Hz), 1.69-1.79 (2H, m), 1.86-2.04 (2H, m), 2.05-2.12 (4H, m), 2.47 (3H, s), 3.56 (1H, tt, J=7, 7 Hz), 4.59 (2H, q, J=7 Hz), 5.69 (1H, d, J=17 Hz), 7.72 (1H, s), 7.75 (1H, s), 7.93 (1H, d, J=17 Hz), 8.50 (1H, d, J=2 Hz), 8.52 (1H, d, J=2 Hz)

EXAMPLE 194

3-[1-Ethyl-6-isopropyl-4-(5-methyl-3-pyridyl)-1H-pyrazolo[3,4-b]pyridin-5-yl]propanoic acid $^1$H-NMR (CDCl$_3$) δ 1.40 (6H, d, J=7 Hz), 1.55 (3H, t, J=7 Hz), 2.49 (3H, s), 2.50 (2H, t, J=7 Hz), 3.00 (2H, t, J=7 Hz), 3.40 (1H, sep, J=7 Hz), 4.58 (2H, q, J=7 Hz), 7.50 (1H, s), 7.67 (1H, s), 8.48 (1H, s), 8.59 (1H, s)
MS (ESI$^+$) m/z 353 (M+1)
mp. 203-205° C.

EXAMPLE 195

(2E)-3-[4-(4-Amino-3,5-dichlorophenyl)-6-cyclopropyl-1-ethyl-1H-pyrazolo[3,4-b]pyridin-5-yl]acrylic acid $^1$H-NMR (DMSO-d$_6$) δ 1.06 (2H, m), 1.18 (2H, m), 1.40 (3H, t, J=7.1 Hz), 2.36 (1H, m), 4.42 (2H, q, J=7.2 Hz), 5.91 (2H, br s), 5.96 (1H, d, J=16.1 Hz), 7.35 (2H, s), 7.78 (1H, d, J=16.1 Hz), 7.85 (1H, s)

EXAMPLE 196

(2E)-3-[4-(5-Bromo-3-pyridyl)-6-cyclopropyl-1-ethyl-1H-pyrazolo[3,4-b]pyridin-5-yl]acrylic acid $^1$H-NMR (CDCl$_3$) δ 1.12 (2H, m), 1.34 (2H, m), 1.53 (3H, t, J=7.2 Hz), 2.37 (1H, m), 4.53 (2H, q, J=7.2 Hz), 6.00 (1H, d, J=16.2 Hz), 7.73 (1H, s), 7.96 (1H, m), 7.98 (1H, d, J=16.0 Hz), 8.61 (1H, m), 8.79 (1H, m)

EXAMPLE 197

(2E)-3-[1-Ethyl-4-(5-ethynyl-3-pyridyl)-6-isopropyl-1H-pyrazolo[3,4-b]pyridin-5-yl]acrylic acid $^1$H-NMR (CDCl$_3$) δ 1.38 (6H, d, J=7.1 Hz), 1.59 (3H, t, J=7.2 Hz), 3.30 (1H, s), 3.45 (1H, h, J=7.1 Hz), 4.61 (2H, q, J=7.2 Hz), 5.65 (1H, d, J=11 Hz), 7.75 (1H, s), 7.91 (1H, s), 7.95 (1H, d, J=11 Hz), 8.61 (1H, bs), 8.78 (1H, bs)

EXAMPLE 198

(2E)-3-[1-Ethyl-6-phenyl-4-(tetrahydro-2H-pyran-4-yl)-1H-pyrazolo[3,4-b]pyridin-5-yl]acrylic acid $^1$H-NMR (CDCl$_3$) δ 1.55 (3H, t, J=6.7 Hz), 1.77 (2H, d, J=11.2 Hz), 2.32-2.51 (2H, m), 3.42-3.54 (3H, m), 4.14-4.22 (2H, m), 4.59 (2H, q, J=6.7 Hz), 5.77 (1H, d, J=13.0 Hz), 7.40-7.49 (3H, m), 7.50-7.56 (2H, m), 7.94 (1H, d, J=13.0 Hz), 8.31 (1H, s)

EXAMPLE 199

(2E)-3-[1,6-Diethyl-4-(5-methyl-3-pyridyl)-1H-pyrazolo[3,4-b]pyridin-5-yl]acrylic acid $^1$H-NMR (CDCl$_3$) δ 1.40 (3H, t, J=7 Hz), 1.58 (3H, t, J=7 Hz), 2.47 (3H, s), 3.16 (2H, q, J=7 Hz), 4.61 (2H, q, J=7 Hz), 5.72 (1H, d, J=14 Hz), 7.72 (1H, s), 7.77 (1H, s), 7.87 (1H, d, J=14 Hz), 8.50 (1H, s), 8.53 (1H, s)

EXAMPLE 200

(2E)-3-(4-Cyclohexyl-6-cyclopropyl-1-ethyl-1H-pyrazolo[3,4-b]pyridin-5-yl)acrylic acid $^1$H-NMR (CDCl$_3$) δ 1.02 (2H, m), 1.24 (2H, m), 1.37-1.51 (3H, m), 1.49 (3H, t, J=7.3 Hz), 1.81-1.93 (7H, m), 2.21 (1H, m), 3.04 (1H, m), 4.47 (2H, q, J=7.2 Hz), 6.14 (1H, d, J=16.1 Hz), 8.11 (1H, s), 8.23 (1H, d, J=16.1 Hz)

EXAMPLE 201

(2E)-3-[1-Ethyl-6-(1-ethylpropyl)-4-(5-methyl-3-pyridyl)-1H-pyrazolo[3,4-b]pyridin-5-yl]acrylic acid $^1$H-NMR (CDCl$_3$) δ 0.83 (6H, t, J=7 Hz), 1.56 (3H, t, J 7 Hz), 1.68-1.83 (2H, m), 1.88-2.00 (2H, m), 2.46 (3H, s), 3.07-3.18 (1H, m), 4.63 (2H, q, J=7 Hz), 5.63 (1H, d, J=15 Hz), 7.74 (1H, s), 7.77 (1H, s), 7.93 (1H, d, J=15 Hz), 8.51 (1H, d, J=1 Hz), 8.52 (1H, d, J=1 Hz)
MS (ESI$^+$) m/z 379 (M+1)
mp. 197-199° C.

EXAMPLE 202

(2E)-3-[4-(5-chloro-2-thienyl)-6-cyclopropyl-1-ethyl-1H-pyrazolo[3,4-b]pyridin-5-yl]acrylic acid $^1$H-NMR (DMSO-d$_6$) δ 1.00-1.07 (2H, m), 1.13-1.20 (2H, m), 1.38 (3H, t, J=7 Hz), 2.35 (1H, qq, J=4, 4 Hz), 4.40 (2H, q, J=7 Hz), 6.15 (1H, d, J=17 Hz), 7.30 (1H, d, J=4 Hz), 7.32 (1H, d, J=4 Hz), 7.32 (1H, d, J=17 Hz), 8.07 (1H, s)

EXAMPLE 203

1-{(2E)-3-[1-Ethyl-6-(methoxymethyl)-4-(5-methyl-3-pyridyl)-1H-pyrazolo[3,4-b]pyridin-5-yl]-2-propen-1-yl}-4-piperidinecarboxylic acid $^1$H-NMR (CDCl$_3$) δ 1.54 (3H, t, J=6.6 Hz), 1.75-1.92 (2H, m), 1.92-2.38 (7H, m), 2.45 (3H, s), 2.86-2.97 (2H, br), 3.33 (2H, d, J=7.5 Hz), 3.49 (3H, s), 4.62 (2H, q, J=6.6 Hz), 4.70 (2H, s), 5.70 (1H, td, J=12.0,6.6 Hz), 6.75 (1H, d, J=12.0 Hz), 7.60 (1H, s), 7.71 (1H, s), 8.45 (1H, s), 8.51 (1H, s)

EXAMPLE 204

(2E)-3-[4-(2-Chloro-4-pyridyl)-1-ethyl-6-phenyl-1H-pyrazolo[3,4-b]pyridin-5-yl]acrylic acid $^1$H-NMR (CDCl$_3$) δ 1.57 (3H, t, J=8 Hz), 4.65 (2H, q, J=8 Hz), 5.47 (1H, d, J=15 Hz), 7.30 (1H, dd, J=5, 1 Hz), 7.41-7.60 (5H, m), 7.65 (1H, d, J=15 Hz), 7.79 (1H, s), 8.58 (1H, d, J=5 Hz)

mp >250° C.

EXAMPLE 205

(2E)-3-[1-Ethyl-6-phenyl-4-(3-pyridyl)-1H-pyrazolo[3,4-b]pyridin-5-yl]acrylic acid $^1$H-NMR (CDCl$_3$) δ 1.59 (3H, t, J=8 Hz), 4.65 (2H, q, J=8 Hz), 7.43-7.53 (4H, m), 7.55-7.87 (5H, m), 8.70-8.78 (2H, m)

EXAMPLE 206

(2E)-3-[4-(Cyclohexylmethyl)-1-ethyl-6-phenyl-1H-pyrazolo[3,4-b]pyridin-5-yl]acrylic acid $^1$H-NMR (CDCl$_3$) δ 1.10-1.19 (5H, m), 1.54 (3H, t, J=7 Hz), 1.65-1.72 (6H, m), 2.97 (2H, d, J=7 Hz), 4.59 (2H, q, J=7 Hz), 5.70 (1H, d, J=15 Hz), 7.42-7.45 (3H, m), 7.52-7.56 (2H, m), 7.82 (1H, d, J=15 Hz), 8.06 (1H, s)

mp. 201-202° C.

EXAMPLE 207

(2E)-3-[4-(5-Chloro-2-thienyl)-1-ethyl-6-phenyl-1H-pyrazolo[3,4-b]pyridin-5-yl]acrylic acid $^1$H-NMR (CDCl$_3$) δ 1.56 (3H, t, J=8 Hz), 4.62 (2H, q, J=8 Hz), 5.58 (1H, d, J=15 Hz), 7.05 (1H, d, J=5 Hz), 7.08 (1H, d, J=5 Hz), 7.43-7.56 (5H, m), 7.90 (1H, d, J=15 Hz), 8.10 (1H, s)

mp 187-188° C.

EXAMPLE 208

(2E)-3-[4-(6-Chloro-3-pyridyl)-1-ethyl-6-phenyl-1H-pyrazolo[3,4-b]pyridin-5-yl]acrylic acid $^1$H-NMR (CDCl$_3$) δ 1.59 (3H, t, J=7 Hz), 4.65 (2H, q, J=7 Hz), 5.45 (1H, d, J=15 Hz), 7.46-7.50 (3H, m), 7.53-7.59 (3H, m), 7.58 (1H, d, J=15 Hz), 7.75 (1H, dd, J=7, 1 Hz), 7.83 (1H, s), 8.51 (1H, d, J=1 Hz)

mp. 255-258° C.

EXAMPLE 209

(2E)-3-[4-(5-Chloro-3-pyridyl)-6-cyclopropyl-1-ethyl-1H-pyrazolo[3,4-b]pyridin-5-yl]acrylic acid $^1$H-NMR (CDCl$_3$) δ 1.09-1.15 (2H, m), 1.32-1.37 (2H, m), 1.53 (3H, t, J=6.6 Hz), 2.31-2.41 (1H, m), 4.53 (2H, q, J=6.6 Hz), 5.99 (1H, d, J=12.9 Hz), 7.72 (1H, s), 7.80 (1H, s), 7.98 (1H, d, J=12.9 Hz), 8.56 (1H, s), 8.69 (1H, s)

EXAMPLE 210

3-[1-Ethyl-6-phenyl-4-(3-pyridyl)-1H-pyrazolo[3,4-b]pyridin-5-yl]propanoic acid $^1$H-NMR (CDCl$_3$) δ 1.54 (3H, t, J=8 Hz), 2.09 (2H, t, J=8 Hz), 3.04 (2H, t, J=8 Hz), 4.59 (2H, q, J=8 Hz), 7.43-7.64 (7H, m), 7.83 (1H, d, J=8 Hz), 8.64-8.74 (2H, m)

EXAMPLE 211

(2E)-3-(1-Ethyl-4,6-diphenyl-1H-pyrazolo[3,4-b]pyridin-5-yl)acrylic acid $^1$H-NMR (CDCl$_3$) δ 1.56 (3H, t, J=8 Hz), 4.62 (2H, q, J=8 Hz), 5.37 (1H, d, J=15 Hz), 7.38-7.62 (9H, m), 7.71 (1H, d, J=15 Hz), 7.81 (1H, s)

mp >250° C.

EXAMPLE 212

(2E)-3-[1-Ethyl-6-isopropyl-4-(5-methyl-3-pyridyl)-1H-pyrazolo[3,4-b]pyridin-5-yl]acrylic acid $^1$H-NMR (CDCl$_3$) δ 1.38 (6H, d, =7 Hz), 1.58 (3H, t, J=7 Hz), 2.49 (3H, s), 3.48 (1H, sep, J=7 Hz), 4.62 (2H, d, J=7 Hz), 5.67 (1H, d, J=15 Hz), 7.74 (1H, s), 7.79 (1H, s), 7.93 (1H, d, J=15 Hz), 8.53 (1H, d, J=1 Hz), 8.54 (1H, d, J=1 Hz)

MS (ESI$^+$) m/z 351 (M+1)

mp. 247-248° C.

EXAMPLE 213

(2E)-3-[4-(5-Chloro-3-pyridyl)-1-ethyl-6-phenyl-1H-pyrazolo[3,4-b]pyridin-5-yl]acrylic acid $^1$H-NMR (CDCl$_3$) δ 1.58 (3H, t, J=7 Hz), 4.65 (2H, q, J=7 Hz), 5.45 (1H, d, J=15 Hz), 7.48-7.50 (3H, m), 7.57-7.60 (2H, m), 7.67 (1H, d, J=15 Hz), 7.81 (1H, s), 7.82 (1H, s), 8.59 (1H, s), 8.72 (1H, s)

mp. 242-244° C.

EXAMPLE 214

(2E)-3-[6-Cyclopropyl-1-ethyl-4-(5-methyl-3-pyridyl)-1H-pyrazolo[3,4-b]pyridin-5-yl]acrylic acid $^1$H-NMR (CDCl$_3$) δ 1.08-1.14 (2H, 1H), 1.32-1.38 (2H, m), 1.53 (3H, t, J=7 Hz), 2.37-2.43 (1H, m), 2.50 (3H, s), 4.54 (2H, q, J=7 Hz), 6.00 (1H, d, J=15 Hz), 7.70 (1H, s), 7.77 (1H, s), 7.93 (1H, d, J=15 Hz), 8.54 (1H, d, J=1 Hz), 8.57 (1H, d, J=1 Hz)

MS (ESI$^+$) m/z 349 (M+1)

mp. 221-222° C.

EXAMPLE 215

(2E)-3-[1-Ethyl-6-isobutyl-4-(5-methyl-3-pyridyl)-1H-pyrazolo[3,4-b]pyridin-5-yl]acrylic acid $^1$H-NMR (CDCl$_3$) δ 1.00 (6H, d, J=7 Hz), 1.57 (3H, t, J=7 Hz), 2.53 (3H, s), 2.91 (2H, d, J=7 Hz), 4.62 (2H, q, J=7 Hz), 5.64 (1H, d, J=15 Hz), 7.72 (1H, s), 7.85 (1H, d, J=1 Hz), 7.87 (1H, d, J=15 Hz), 8.57 (1H, d, J=1 Hz), 8.59 (1H, d, J=1 Hz)
mp. 212-213° C.

EXAMPLE 216

(2E)-3-[1-Ethyl-6-(2-fluorophenyl)-4-(5-methyl-3-pyridyl)-1H-pyrazolo[3,4-b]pyridin-5-yl]acrylic acid $^1$H-NMR (CDCl$_3$) δ 1.57 (3H, t, J=7 Hz), 2.45 (3H, s), 4.62 (2H, q, J=7 Hz), 5.43 (1H, d, J=13 Hz), 7.14 (1H, dd, J=7,7 Hz), 7.30 (1H, dd, J=7,7 Hz), 7.41-7.66 (4H, m), 7.85 (1H, s), 8.54 (2H, br)

EXAMPLE 217

(2E)-3-[4-(2-Chloro-4-pyridyl)-1-ethyl-6-isopropyl-1H-pyrazolo[3,4-b]pyridin-5-yl]acrylic acid $^1$H-NMR (CDCl$_3$) δ 1.38 (6H, d, J=6 Hz), 1.57 (3H, t, J=7 Hz), 3.45 (1H, qq, J=6, 6 Hz), 4.60 (2H, q, J=7 Hz), 5.69 (1H, d, J=17 Hz), 7.26 (1H, d, J=5 Hz), 7.39 (1H, s), 7.72 (1H, s), 7.97 (1H, d, J=17 Hz), 8.54 (1H, d, J=5 Hz)

EXAMPLE 218

(2E)-3-[1-Ethyl-4-(5-methoxy-3-pyridyl)-6-phenyl-1H-pyrazolo[3,4-b]pyridin-5-yl]acrylic acid $^1$H-NMR (CDCl$_3$) δ 1.55 (3H, t, J=7 Hz), 3.93 (3H, s), 4.65 (2H, q, J=7 Hz), 5.45 (1H, d, J=15 Hz), 7.40 (1H, t, J=1 Hz), 7.45-7.50 (3H, m), 7.57-7.60 (2H, m), 7.67 (1H, d, J=15 Hz), 7.84 (1H, s), 8.30 (1H, d, J=1 Hz), 8.44 (1H, d, J=1 Hz)
mp. 253-254° C.

EXAMPLE 219

(2E)-3-[6-Butyl-1-ethyl-4-(5-methyl-3-pyridyl)-1H-pyrazolo[3,4-b]pyridin-5-yl]acrylic acid $^1$H-NMR (CDCl$_3$) δ 0.99 (3H, t, J=7 Hz), 1.47 (2H, tq, J=7,7 Hz), 1.56 (3H, t, J=7 Hz), 1.75-1.86 (2H, m), 2.48 (3H, s), 3.04 (2H, t, J=7 Hz), 4.60 (2H, q, J=7 Hz), 5.70 (1H, d, J=12 Hz), 7.73 (1H, s), 7.75 (1H, s), 7.87 (1H, d, J=12 Hz), 8.51 (2H, br)

EXAMPLE 220

(2E)-3-[1-Ethyl-6-(4-fluorophenyl)-4-(5-methyl-3-pyridyl)-1H-pyrazolo[3,4-b]pyridin-5-yl]acrylic acid $^1$H-NMR (CDCl$_3$) δ 1.56 (3H, t, J=6.7 Hz), 2.49 (3H, s), 4.62 (2H, q, J=6.7 Hz), 5.44 (1H, d, J=13.1 Hz), 7.15 (2H, dd, J=7.8, 7.8 Hz), 7.53-7.66 (3H, m), 7.71 (1H, s), 7.80 (1H, s), 8.46 (1H, s), 8.55 (1H, s)

EXAMPLE 221

(2E)-3-[1-Ethyl-6-phenyl-4-(3-quinolinyl)-1H-pyrazolo[3,4-b]pyridin-5-yl]acrylic acid $^1$H-NMR (CDCl$_3$) δ 1.59 (3H, t, J=6.6 Hz), 4.65 (2H, q, J=6.6 Hz), 5.46 (1H, d, J=13.0 Hz), 7.41-7.51 (3H, m), 7.56-7.72 (3H, m), 7.69-7.83 (2H, m), 7.90 (1H, s), 7.95 (1H, d, J=7.4 Hz), 8.16 (1H, d, J=7.4 Hz), 8.45 (1H, s), 8.96 (1H, s)

EXAMPLE 222

(2E)-3-[4-(2-Chloro-4-pyridyl)-6-cyclopropyl-1-ethyl-1H-pyrazolo[3,4-b]pyridin-5-yl]acrylic acid $^1$H-NMR (CDCl$_3$) δ 1.08-1.15 (2H, m), 1.229-1.36 (2H, m), 1.53 (3H, t, J=6.7 Hz), 2.30-2.40 (1H, m), 4.54 (2H, q, J=6.7 Hz), 5.94 (1H, d, J=12.6 Hz), 7.26 (1H, d, J=4.5 Hz), 7.40 (1H, s), 7.68 (1H, s), 7.88 (1H, d, J=12.6 Hz), 8.52 (1H, d, J=4.5 Hz)

EXAMPLE 223

(2E)-3-[4-(5-Bromo-3-pyridyl)-6-cyclopentyl-1-ethyl-1H-pyrazolo[3,4-b]pyridin-5-yl]acrylic acid $^1$H-NMR (CDCl$_3$) δ 1.55 (3H, t, J=7 Hz), 1.66-2.09 (8H, m), 3.54 (1H, tt, J=7,7 Hz), 4.59 (2H, q, J=7 Hz), 5.68 (1H, d, J=12 Hz), 7.75 (1H, s), 7.94 (1H, s), 7.97 (1H, d, J=12 Hz), 8.60 (1H, s), 8.75 (1H, s)

EXAMPLE 224

(2E)-3-[4-(5-Chloro-2-thienyl)-1-ethyl-6-isopropyl-1H-pyrazolo[3,4-b]pyridin-5-yl]acrylic acid $^1$H-NMR (CDCl$_3$) δ 1.35 (6H, d, J=7 Hz), 1.56 (3H, t, J=7 Hz), 3.49 (1H, sep, J=7 Hz), 4.59 (2H, q, J=7 Hz), 6.02 (1H, d, J=15 Hz), 7.02 (1H, d, J=5 Hz), 7.05 (1H, d, J=5 Hz), 8.01 (1H, d, J=15 Hz), 8.04 (1H, s)
mp. 163-165° C.

EXAMPLE 225

(2E)-3-[4-(5-Bromo-3-pyridyl)-1-ethyl-6-isopropyl-1H-pyrazolo[3,4-b]pyridin-5-yl]acrylic acid $^1$H-NMR (CDCl$_3$) δ 1.36 (6H, d, J=7 Hz), 1.57 (3H, t, J=8 Hz), 3.45 (1H, m), 4.61 (2H, q, J=8 Hz), 5.66 (1H, d, J=15 Hz), 7.76 (1H, s), 7.91-8.00 (2H, m), 8.59 (1H, d, J=1 Hz), 8.76 (1H, d, J=1 Hz)
mp. 234-235° C.

EXAMPLE 226

(2E)-3-[4-(5-Bromo-3-pyridyl)-1-ethyl-6-(methoxymethyl)-1H-pyrazolo[3,4-b]pyridin-5-yl]acrylic acid $^1$H-NMR (CDCl$_3$) δ 1.58 (3H, t, J=7 Hz), 3.54 (3H, s), 4.64 (2H, q, J=7 Hz), 4.73 (2H, s), 6.04 (1H, d, J=15 Hz), 7.84 (1H, s), 7.91 (1H, d, J=15 Hz), 7.96 (1H, t, J=1 Hz), 8.63 (1H, d, J=1 Hz), 8.82 (1H, d, J=1 Hz)
mp. 180-182° C.

EXAMPLE 227

(2E)-3-[1-Ethyl-4-(5-methyl-3-pyridyl)-6-propyl-1H-pyrazolo[3,4-b]pyridin-5-yl]acrylic acid $^1$H-NMR (CDCl$_3$) δ 1.05 (3H, t, J=7 Hz), 1.56 (3H, t, J=7 Hz), 1.78-1.92 (2H, m), 2.46 (3H, s), 3.00 (2H, t, J=7 Hz), 4.60 (2H, q, J=7 Hz), 5.68 (1H, d, J=13 Hz), 7.67 (1H, s), 7.75 (1H, s), 7.86 (1H, d, J=13 Hz), 8.47 (1H, s), 8.53 (1H, s)

EXAMPLE 228

(2E)-3-[4-(5-Chloro-3-pyridyl)-1-ethyl-6-isopropyl-1H-pyrazolo[3,4-b]pyridin-5-yl]acrylic acid $^1$H-NMR (CDCl$_3$) δ 1.37 (6H, d, J=7 Hz), 1.57 (3H, t, J=7 Hz), 3.47 (1H, sep, J=7 Hz), 4.63 (2H, q, J=7 Hz), 5.68 (1H, d, J=15 Hz), 7.77 (1H, s), 7.80 (1H, d, J=1 Hz), 7.98 (1H, d, J=15 Hz), 8.58 (1H, d, J=1 Hz), 8.69 (1H, d, J=1 Hz)

mp. 218-220.5° C.

EXAMPLE 229

(2E)-3-[6-Cyclobutyl-1-ethyl-4-(5-methyl-3-pyridyl)-1H-pyrazolo[3,4-b]pyridin-5-yl]acrylic acid $^1$H-NMR (CDCl$_3$) δ 1.60 (3H, t, J=7 Hz), 1.93-2.17 (2H, m), 2.34-2.43 (2H, m), 2.47 (3H, s), 2.57-2.65 (2H, m), 4.01 (1H, quintet, J=7 Hz), 4.65 (2H, q, J=7 Hz), 5.67 (1H, d, J=15 Hz), 7.68 (1H, d, J=1 Hz), 7.77 (1H, s), 7.82 (1H, d, J=15 Hz), 8.49 (1H, s), 8.53 (1H, s)

mp. 222-223° C.

EXAMPLE 230

3-[6-cyclobutyl-1-ethyl-4-(5-methyl-3-pyridyl)-1H-pyrazolo[3,4-b]pyridin-5-yl]propanoic acid $^1$H-NMR (CDCl$_3$) δ 1.59 (3H, t, J=7 Hz), 1.93-2.04 (1H, m), 2.07-2.17 (1H, m), 2.33-2.45 (4H, m), 2.44 (3H, s), 2.59-2.70 (2H, m), 3.00 (2H, t, J=7 Hz), 3.99 (1H, quintet, J=7 Hz), 4.64 (2H, q, J=7 Hz), 7.51 (1H, s), 7.57 (1H, s), 8.45 (1H, s), 8.54 (1H, s)

MS (ESI$^+$) m/z 365 (M+1)

mp. 212-213° C.

EXAMPLE 231

(2E)-3-[4-(5-chloro-3-pyridyl)-1-ethyl-6-(methoxymethyl)-1H-pyrazolo[3,4-b]pyridin-5-yl]acrylic acid $^1$H-NMR (CDCl$_3$) δ 1.57 (3H, t, J=8 Hz), 3.53 (3H, s), 4.65 (2H, q, J=8 Hz), 4.73 (2H, s), 6.03 (1H, d, J=15 Hz), 7.79-7.85 (2H, m), 7.90 (1H, d, J=15 Hz), 8.60 (1H, d, J=1 Hz), 8.71 (1H, d, J=1 Hz)

mp. 187-188° C.

EXAMPLE 232

(2E)-3-[1-Ethyl-6-(2-fluorophenyl)-4-(5-methyl-3-pyridyl)-1H-pyrazolo[3,4-b]pyridin-5-yl]acrylic acid $^1$H-NMR (CDCl$_3$) δ 1.57 (3H, t, J=6.8 Hz), 2.46 (3H, s), 4.63 (2H, q, J=6.8 Hz), 5.44 (1H, d, J=13.1 Hz), 7.13 (1H, dd, J=7.7, 7.7 Hz), 7.80 (1H, dd, J=7.7, 7.7 Hz), 7.40-7.55 (2H, m), 7.60 (1H, d, J=13.0 Hz), 7.71 (1H, s), 7.85 (1H, s), 8.45-8.70 (2H, br)

EXAMPLE 233

(2E)-3-(1-Ethyl-4-isopropyl-6-phenyl-1H-pyrazolo[3,4-b]pyridin-5-yl)acrylic acid $^1$H-NMR (CDCl$_3$) δ 1.55 (3H, t, J=6.6 Hz), 1.57 (6H, d, J=6.6 Hz), 3.60 (1H, h, J=6.6 Hz), 4.59 (2H, q, J=6.6 Hz), 5.76 (1H, d, J=12.2 Hz), 7.40-7.55 (5H, m), 7.92 (1H, d, J=12.2 Hz), 8.22 (1H, s)

EXAMPLE 234

(2E)-3-[6-(Ethoxymethyl)-1-ethyl-4-(5-methyl-3-pyridyl)-1H-pyrazolo[3,4-b]pyridin-5-yl]acrylic acid $^1$H-NMR (CDCl$_3$) δ 1.31 (3H, t, J=7 Hz), 1.59 (3H, t, J=7 Hz), 2.47 (3H, s), 3.72 (2H, q, J=7 Hz), 4.65 (2H, q, J=7 Hz), 4.79 (2H, s), 6.07 (1H, d, J=15 Hz), 7.68 (1H, s), 7.82 (1H, s), 7.90 (1H, d, J=15 Hz), 8.54 (1H, d, J=1 Hz), 8.57 (1H, d, J=1 Hz)

mp. 187-188° C.

EXAMPLE 235

(2E)-3-[6-(Cyclopropylmethyl)-1-ethyl-4-(5-methyl-3-pyridyl)-1H-pyrazolo[3,4-b]pyridin-5-yl]acrylic acid $^1$H-NMR (CDCl$_3$) δ 0.30-0.35 (2H, m), 0.50-0.58 (2H, m), 1.20-1.30 (1H, m), 1.57 (3H, t, J=7 Hz), 2.46 (3H, s), 2.98 (2H, d, J=7 Hz), 4.61 (2H, q, J=7 Hz), 5.71 (1H, d, J=15 Hz), 7.71 (1H, s), 7.79 (1H, s), 7.89 (1H, d, J=15 Hz), 8.50 (1H, d, J=1 Hz), 8.53 (1H, d, J=1 Hz)

mp. 204-206° C.

EXAMPLE 236

(2E)-3-[6-(2,2-Dimethylpropyl)-1-ethyl-4-(5-methyl-3-pyridyl)-1H-pyrazolo[3,4-b]pyridin-5-yl]acrylic acid $^1$H-NMR (CDCl$_3$) δ 1.05 (9H, s), 1.47 (3H, t, J=7 Hz), 2.47 (3H, s), 3.00 (2H, s), 4.61 (2H, q, J=7 Hz), 5.58 (1H, d, J=15 Hz), 7.70 (1H, s), 7.78 (1H, s), 7.95 (1H, d, J=15 Hz), 8.48 (1H, d, J=1 Hz), 8.52 (1H, d, J=1 Hz)

mp. 216-217.5° C.

EXAMPLE 237

(2E)-3-[1-Ethyl-6-(5-methyl-3-isoxazolyl)-4-(5-methyl-3-pyridyl)-1H-pyrazolo[3,4-b]pyridin-5-yl]acrylic acid $^1$H-NMR (CDCl$_3$) δ 1.58 (3H, t, J=7 Hz), 2.47 (3H, s), 2.54 (3H, s), 4.65 (2H, q, J=7 Hz), 5.54 (1H, d, J=17 Hz), 6.52 (1H, s), 7.68 (1H, s), 7.86 (1H, s), 8.06 (1H, d, J=17 Hz), 8.51 (1H, s), 8.56 (1H, s)

EXAMPLE 238

(2E)-3-[4-(2-Chloro-4-pyridyl)-6-cyclopentyl-1-ethyl-1H-pyrazolo[3,4-b]pyridin-5-yl]acrylic acid $^1$H-NMR (CDCl$_3$) δ 1.56 (3H, t, J=7 Hz), 1.70-1.78 (2H, m), 1.88-1.97 (2H, m), 2.00-2.10 (4H, m), 3.54 (1H, quintet, J=7 Hz), 4.60 (2H, q, J=7 Hz), 5.69 (1H, d, J=15 Hz), 7.25 (1H, dd, J=4, 1 Hz), 7.40 (1H, t, J=1 Hz), 7.71 (1H, s), 7.99 (1H, d, J=15 Hz), 8.54 (1H, d, J=4 Hz)

mp. 206-208° C.

EXAMPLE 239

3-[6-Butyl-1-ethyl-4-(5-methyl-3-pyridyl)-1H-pyrazolo[3,4-b]pyridin-5-yl]propanoic acid $^1$H-NMR (CDCl$_3$) δ 1.00 (3H, t, J=7 Hz), 1.46-1.58 (5H, m), 1.80-1.93 (2H, m), 2.45 (3H, s), 2.47 (2H, t, J=7 Hz), 2.95-3.07 (4H, m), 4.56 (2H, q, J=7 Hz), 7.56 (1H, s), 7.60 (1H, s), 8.45 (1H, s), 8.54 (1H, s)

EXAMPLE 240

(2E)-3-[1-Ethyl-6-(isopropoxymethyl)-4-(5-methyl-3-pyridyl)-1H-pyrazolo[3,4-b]pyridin-5-yl]acrylic acid $^1$H-NMR (CDCl$_3$) δ 1.30 (6H, d, J=7 Hz), 1.57 (3H, t, J=7 Hz), 3.85 (1H, sep, J=7 Hz), 4.63 (2H, q, J=7 Hz), 4.75 (2H, s), 5.03 (1H, d, J=15 Hz), 7.64 (1H, s), 7.80 (1H, s), 7.94 (1H, d, J=15 Hz), 8.51 (1H, d, J=1 Hz), 8.55 (1H, d, J=1 Hz)

MS (ESI$^+$) m/z 381 (M+1)

mp. 198-199° C.

EXAMPLE 241

3-[6-(Cyclopropylmethyl)-1-ethyl-4-(5-methyl-3-pyridyl)-1H-pyrazolo[3,4-b]pyridin-5-yl]propanoic acid $^1$H-NMR (CDCl$_3$) δ 0.33-0.38 (2H, m), 0.54-0.61 (2H, m), 1.28-1.38 (1H, m), 1.55 (3H, t, J=7 Hz), 2.45 (3H, s), 2.46 (2H, t, J=7 Hz), 2.94 (1H, d, J=7 Hz), 3.05 (2H, t, J=7 Hz), 4.59 (2H, q, J=7 Hz), 7.52 (1H, s), 7.58 (1H, s), 8.45 (1H, d, J=1 Hz), 8.54 (1H, d, J=1 Hz)

MS (ESI$^+$) m/z 365 (M+1)

mp. 184-185° C.

EXAMPLE 242

(2E)-3-[1-Ethyl-6-isopropyl-4-(2-methyl-4-pyridyl)-1H-pyrazolo[3,4-b]pyridin-5-yl]acrylic acid $^1$H-NMR (CDCl$_3$) δ 1.39 (6H, d, J=7 Hz), 1.57 (3H, t, J=7 Hz), 2.65 (3H, s), 3.49 (1H, sep, J=7 Hz), 4.60 (2H, q, J=7 Hz), 5.74 (1H, d, J=15 Hz), 7.19 (1H, dd, J=4, 1 Hz), 7.25 (1H, d, J=1 Hz), 7.70 (1H, s), 7.91 (1H, d, J=15 Hz), 8.70 (1H, d, J=4Hz)

mp. 260-262.5° C.

EXAMPLE 243

(2E)-3-[4-(5-Bromo-3-pyridyl)-1-ethyl-6-phenyl-1H-pyrazolo[3,4-b]pyridin-5-yl]acrylic acid $^1$H-NMR (CDCl$_3$) δ 1.55 (3H, t, J=6.7 Hz), 4.65 (2H, q, J=6.7 Hz), 5.44 (1H, d, J=13.2 Hz), 7.40-7.52 (3H, m), 7.52-7.60 (2H, m), 7.77 (1H, d, J=13.2 Hz), 7.82 (1H, s), 7.98 (1H, s), 8.61 (1H, s), 8.80 (1H, s)

EXAMPLE 244

To a solution of bis(N-{[4-(5-bromo-3-pyridyl)-6-cyclopentyl-1-ethyl-1H-pyrazolo[3,4-b]pyridin-5-yl]methyl}-N,N-diethylethanaminium) sulfate (102 mg) in MeOH (0.51 ml) was added sodium methoxide MeOH solution (2M, 0.14 ml) and refluxed for 2 days. The mixture was evaporated and the residue was purified with silica gel column chromatography to give 4-(5-bromo-3-pyridyl)-6-cyclopentyl-1-ethyl-5-(methoxymethyl)-1H-pyrazolo[3,4-b]pyridine as a colorless solid.

$^1$H-NMR (CDCl$_3$) δ 1.54 (3H, t, J=6.6 Hz), 1.66-1.83 (2H, m), 1.88-2.17 (6H, m), 3.39 (3H, s), 3.59-3.71 (1H, m), 4.31 (2H, s), 4.57 (2H, q, J=6.6 Hz), 7.70 (1H, s), 8.09 (1H, s), 8.72 (1H, bs), 8.80 (1H, bs)

The following compound(s) was(were) obtained in a similar manner to that of Example 65.

EXAMPLE 245

1-Ethyl-N-(1-ethylpropyl)-4-(5-methyl-3-pyridyl)-6-phenyl-1H-pyrazolo[3,4-b]pyridine-5-carboxamide $^1$H-NMR (CDCl$_3$) δ 0.40 (6H, t, J=7 Hz), 0.97-1.19 (2H, m), 1.56 (3H, t, J=7 Hz), 2.44 (3H, s), 3.51-3.58 (1H, m), 4.65 (2H, q, J=7 Hz), 5.12 (1H, d, J=7 Hz), 7.43-7.48 (3H, m), 7.80-7.84 (2H, m), 7.87 (1H, t, J=1 Hz), 8.56 (1H, d, J=1 Hz), 8.69 (1H, d, J=1 Hz)

MS (ESI$^+$) m/z 428 (M+1)

mp. 170-172° C.

EXAMPLE 246

1-Ethyl-4-(5-methyl-3-pyridyl)-N-(2-phenoxyethyl)-6-phenyl-1H-pyrazolo[3,4-b]pyridine-5-carboxamide $^1$H-NMR (CDCl$_3$) δ 2.33 (3H, s), 3.45 (2H, q, J=7 Hz), 3.57 (2H, t, J=7 Hz), 4.65 (2H, q, J=7 Hz), 5.86-5.93 (1H, m), 6.65 (2H, d, J=7 Hz), 6.98 (1H, t, J=7 Hz), 7.23-7.27 (2H, m), 7.29-7.34 (3H, m), 7.73-7.77 (3H, m), 7.90 (1H, s), 8.49 (1H, d, J=1 Hz), 8.67 (1H, d, J=1 Hz)

MS (ESI$^+$) m/z 478 (M+1)

mp. 175-176° C.

EXAMPLE 247

N-(Cyclohexylmethyl)-1-ethyl-4-(5-methyl-3-pyridyl)-6-phenyl-1H-pyrazolo[3,4-b]pyridine-5-carboxamide $^1$H-NMR (CDCl$_3$) δ 0.97-1.20 (6H, m), 1.55 (3H, t, J=7 Hz), 2.44 (3H, s), 2.84 (2H, t, J=7 Hz), 4.65 (2H, q, J=7 Hz), 5.41 (1H, t, J=7 Hz), 7.44-7.48 (3H, m), 7.79-7.84 (3H, m), 7.90 (1H, s), 8.55 (1H, d, J=1 Hz), 8.65 (1H, d, J=1 Hz)

mp. 197-199° C.

EXAMPLE 248

A mixture of ethyl (2Z)-2-benzoyl-3-(6-chloro-3-pyridyl) acrylate (2.018 g) and 5-amino-1-ethylpyrazole (710 mg) in N-methylpyrrolidone (15 ml) was heated at 140° C. for 3.5 hours. Another 5-amino-1-ethylpyrazole (200 mg) was added and the mixture was heated at 140° C. for 2 hours. After cooling, 2,3-dichloro-5,6-dicyano-1,4-benzoquinone (1.45 g) was added and the mixture was stirred at room temperature for 1 hour. The reaction mixture was poured into saturated aqueous $NaHCO_3$ and extracted with EtOAc. The organic layer was washed with saturated aqueous $NaHCO_3$ (×4), brine, dried over anhydrous $MgSO_4$ and concentrated in vacuo. The residue was purified by flash column chromatography on silica gel eluting with a mixture of EtOAc and n-hexane (1:7) to give ethyl 4-(6-chloro-3-pyridyl)-1-ethyl-6-phenyl-1H-pyrazolo[3,4-b]pyridine-5-carboxylate (2.024 g) as a brown oil.

$^1$H-NMR ($CDCl_3$) δ 0.87 (3H, t, J=7 Hz), 1.57 (3H, t, J=7 Hz), 3.95 (2H, q, J=7 Hz), 4.67 (2H, q, J=7 Hz), 7.45-7.53 (4H, m), 7.67-7.70 (2H, m), 7.87 (1H, d, J=7 Hz), 7.88 (1H, s), 8.59 (1H, d, J=1 Hz)

The following compound(s) was(were) obtained in a similar manner to that of Example 248.

EXAMPLE 249

Ethyl 1-ethyl-6-isopropyl-4-(2-methyl-4-pyridyl)-1H-pyrazolo[3,4-b]pyridine-5-carboxylate $^1$H-NMR ($CDCl_3$) δ 1.04 (3H, t, J=7 Hz), 1.39 (6H, d, J=7 Hz), 1.56 (3H, t, J=7 Hz), 2.64 (3H, s), 3.29-3.40 (1H, m), 4.14 (2H, q, J=7 Hz), 4.61 (2H, q, J=7 Hz), 7.22-7.26 (2H, m), 7.83 (1H, s), 8.64 (1H, d, J=5 Hz)
MS (ESI$^+$) m/z 353(M+1)

EXAMPLE 250

Ethyl 6-butyl-1-ethyl-4-(5-methyl-3-pyridyl)-1H-pyrazolo[3,4-b]pyridine-5-carboxylate $^1$H-NMR ($CDCl_3$) δ 0.97 (3H, t, J=7 Hz), 1.07 (3H, t, J=7 Hz), 1.45 (2H, qt, J=7,7 Hz), 1.56 (3H, t, J=7 Hz), 1.78-1.88 (2H, m), 2.43 (3H, s), 2.99 (2H, t, J=7 Hz), 4.15 (2H, q, J=7 Hz), 4.61 (2H, q, J=7 Hz), 7.63 (1H, s), 7.83 (1H, s), 8.55 (2H, s)

EXAMPLE 251

Ethyl 1-ethyl-6-(2-fluorophenyl)-4-(5-methyl-3-pyridyl)-1H-pyrazolo[3,4-b]pyridine-5-carboxylate $^1$H-NMR ($CDCl_3$) δ 0.84 (3H, t, J=6.8 Hz), 1.58 (3H, t, J=6.7 Hz), 2.44 (3H, s), 3.91 (2H, q, J=6.8 Hz), 4.64 (2H, q, J=6.7 Hz), 7.16 (1H, dd, J=7.7, 7.9 Hz), 7.25-7.30 (1H, m), 7.40-7.48 (1H, m), 7.55-7.61 (1H, m), 7.68 (1H, s), 7.92 (1H, s), 8.58 (2H, s)

EXAMPLE 252

Ethyl 1-ethyl-6-(4-methoxyphenyl)-4-(5-methyl-3-pyridyl)-1H-pyrazolo[3,4-b]pyridine-5-carboxylate $^1$H-NMR ($CDCl_3$) δ 0.92 (3H, t, J=7 Hz), 1.57 (3H, t, J=7 Hz), 2.43 (3H, s), 3.85 (3H, s), 3.97 (2H, q, J=7 Hz), 4.64 (2H, q, J=7 Hz), 6.98 (2H, d, J=8 Hz), 7.65 (2H, d, J=8 Hz), 7.77 (1H, s), 7.85 (1H, s), 8.55 (1H, s), 8.56 (1H, s)

EXAMPLE 253

Ethyl 1-ethyl-6-phenyl-4-(3-quinolinyl)-1H-pyrazolo[3,4-b]pyridine-5-carboxylate $^1$H-NMR ($CDCl_3$) δ 0.71 (3H, t, J=6.7 Hz), 1.60 (3H, t, J=6.7 Hz), 3.91 (2H, q, J=6.7 Hz), 4.69 (2H, q, J=6.7 Hz), 7.46-7.55 (4H, m), 7.58-7.75 (3H, m), 7.78-7.95 (3H, m), 8.40 (1H, s), 9.09 (1H, s)

EXAMPLE 254

Ethyl 4-(5-chloro-2-thienyl)-1-ethyl-6-methyl-1H-pyrazolo[3,4-b]pyridine-5-carboxylate $^1$H-NMR ($CDCl_3$) δ 1.25 (3H, t, J=8 Hz), 1.54 (3H, t, J=8 Hz), 2.70 (3H, s), 4.30 (2H, q, J=8 Hz), 4.58 (2H, q, J=8 Hz), 7.00 (1H, d, J=5 Hz), 7.14 (1H, d, J=5 Hz), 8.08 (1H, s)

EXAMPLE 255

Ethyl 4-cyclohexyl-1-ethyl-6-phenyl-1H-pyrazolo[3,4-b]pyridine-5-carboxylate $^1$H-NMR ($CDCl_3$) δ 1.03 (3H, t, J=6.6 Hz), 1.38-1.48 (2H, m), 1.54 (3H, t, J=6.6 Hz), 1.82-2.06 (8H, m), 2.89-3.01 (1H, m), 4.10 (2H, q, J=6.6 Hz), 4.59 (2H, q, J=6.6 Hz), 7.41-7.45 (3H, m), 7.62-7.66 (2H, m), 8.23 (1H, s)

EXAMPLE 256

Ethyl 4-(2-chloro-4-pyridyl)-1-ethyl-6-phenyl-1H-pyrazolo[3,4-b]pyridine-5-carboxylate $^1$H-NMR ($CDCl_3$) δ 0.91 (3H, t, J=8 Hz), 1.57 (3H, t, J=8 Hz), 4.07 (2H, q, J=8 Hz), 4.67 (2H, q, J=8 Hz), 7.40 (1H, br d, J=6 Hz), 7.49-7.53 (3H, m), 7.64-7.71 (2H, m), 8.55 (1H, d, J=6 Hz)

EXAMPLE 257

Ethyl 1-ethyl-6-phenyl-4-(3-pyridyl)-1H-pyrazolo[3,4-b]pyridine-5-carboxylate $^1$H-NMR ($CDCl_3$) δ 0.85 (3H, t, J=8 Hz), 1.58 (3H, t, J=8 Hz), 3.93 (2H, q, J=8 Hz), 7.42-7.52 (4H, m), 7.65-7.73 (2H, m), 7.87-7.94 (2H, m), 8.75 (1H, dd, J=7, 1Hz), 8.80 (1H, d, J=1 Hz)

EXAMPLE 258

Ethyl 4-(5-chloro-2-thienyl)-1-ethyl-6-phenyl-1H-pyrazolo[3,4-b]pyridine-5-carboxylate $^1$H-NMR ($CDCl_3$) δ 0.96 (3H, t, J=8 Hz), 1.56 (3H, t, J=8 Hz), 4.04 (2H, q, J=8 Hz), 4.64 (2H, q, J=8 Hz), 7.02 (1H, d, J=5 Hz), 7.20 (1H, d, J=5 Hz), 7.41-7.51 (3H, m), 7.64-7.71 (2H, m), 8.16 (1H, s)

EXAMPLE 259

Ethyl 4-(cyclohexylmethyl)-1-ethyl-6-phenyl-1H-pyrazolo [3,4-b]pyridine-5-carboxylate $^1$H-NMR ($CDCl_3$) δ 0.95 (3H, t, J=7 Hz), 1.04-1.21 (5H, m), 1.55 (3H, t, J=7 Hz), 1.63-1.74 (6H, m), 2.95 (2H, d, J=7

Hz), 4.05 (2H, q, J=7 Hz), 4.60 (2H, q, J=7 Hz), 7.42-7.47 (3H, m), 7.64-7.67 (2H, m), 8.08 (1H, s)

EXAMPLE 260

Ethyl 4-(2-chloro-4-pyridyl)-1-ethyl-6-isopropyl-1H-pyrazolo[3,4-b]pyridine-5-carboxylate $^1$H-NMR (CDCl$_3$) δ 1.10 (3H, t, J=7 Hz), 1.40 (6H, d, J=6 Hz), 1.56 (3H, t, J=7 Hz), 3.35 (1H, qq, J=6, 6 Hz), 4.16 (2H, q, J=7 Hz), 4.61 (2H, q, J=7 Hz), 7.35 (1H, dd, J=5, 1 Hz), 7.47 (1H, d, J=1 Hz), 7.81 (1H, s), 8.54 (1H, d, J=5 Hz)

EXAMPLE 261

Ethyl 1-ethyl-6-isopropyl-4-(5-methyl-3-pyridyl)-1H-pyrazolo[3,4-b]pyridine-5-carboxylate $^1$H-NMR (CDCl$_3$) δ 1.06 (3H, t, J=7 Hz), 1.40 (6H, d, J=7 Hz), 1.56 (3H, t, J=7 Hz), 2.43 (3H, s), 3.33 (1H, sep, J=7 Hz), 4.15 (2H, q, J=7 Hz), 4.62 (2H, q, J=7 Hz), 7.64 (1H, s), 7.81 (1H, s), 8.54 (1H, d, J=1 Hz), 8.57 (1H, d, J=1 Hz)

EXAMPLE 262

Ethyl 1-ethyl-4,6-diphenyl-1H-pyrazolo[3,4-b]pyridine-5-carboxylate $^1$H-NMR (CDCl$_3$) δ 0.84 (3H, t, J=8 Hz), 1.57 (3H, t, J=8 Hz), 3.92 (2H, q, J=8 Hz), 4.65 (2H, q, J=8 Hz), 7.44-7.59 (8H, m), 7.67-7.73 (2H, m), 7.92 (1H, s)

EXAMPLE 263

Ethyl 4-(5-chloro-3-pyridyl)-1-ethyl-6-phenyl-1H-pyrazolo[3,4-b]pyridine-5-carboxylate $^1$H-NMR (CDCl$_3$) δ 0.89 (3H, t, J=7 Hz), 1.58 (6H, d, J=7 Hz), 3.96 (2H, q, J=7 Hz), 4.66 (2H, q, J=7 Hz), 7.45-7.49 (3H, m), 7.65-7.68 (2H, m), 7.89 (1H, s), 7.90 (1H, s), 8.67 (1H, d, J=1Hz), 8.71 (1H, d, J=1 Hz)

EXAMPLE 264

Ethyl 1-ethyl-4-(5-methoxy-3-pyridyl)-6-phenyl-1H-pyrazolo[3,4-b]pyridine-5-carboxylate $^1$H-NMR (CDCl$_3$) δ 0.86 (3H, t, J=7 Hz), 1.58 (3H, d, J=7 Hz), 3.92 (3H, s), 3.95 (2H, q, J=7 Hz), 4.68 (2H, q, J=7 Hz), 7.42-7.44 (1H, m), 7.46-7.49 (3H, m), 7.68-7.70 (2H, m), 7.93 (1H, s), 8.40 (1H, d, J=1 Hz), 8.44 (1H, d, J=1 Hz)
MS (ESI$^+$) m/z 402(M)

EXAMPLE 265

Ethyl 1-ethyl-6-isobutyl-4-(5-methyl-3-pyridyl)-1H-pyrazolo[3,4-b]pyridine-5-carboxylate $^1$H-NMR (CDCl$_3$) δ 0.98 (6H, d, J=7 Hz), 1.07 (3H, t, J=7 Hz), 1.55 (3H, t, J=7 Hz), 2.31 (1H, sep, J=7 Hz), 2.44 (3H, s), 2.88 (2H, d, J=7 Hz), 4.15 (2H, q, J=7 Hz), 4.62 (2H, q, J=7 Hz), 7.65 (1H, s), 7.82 (1H, s), 8.57 (2H, s)

EXAMPLE 266

Ethyl 1-ethyl-6-(4-fluorophenyl)-4-(5-methyl-3-pyridyl)-1H-pyrazolo[3,4-b]pyridine-5-carboxylate $^1$H-NMR (CDCl$_3$) δ 0.9 (3H, t, J=7 Hz), 2.45 (3H, s), 3.95 (2H, q, J=7 Hz), 4.65 (2H, q, J=7 Hz), 7.16 (2H, dd, J=9 Hz), 7.64-7.73 (3H, m), 7.89 (1H, s), 8.59 (2H, s)

EXAMPLE 267

Ethyl 4-(5-chloro-2-thienyl)-1-ethyl-6-isopropyl-1H-pyrazolo[3,4-b]pyridine-5-carboxylate $^1$H-NMR (CDCl$_3$) δ 1.24 (3H, t, J=7 Hz), 1.37 (6H, d, J=7 Hz), 1.54 (3H, d, J=7 Hz), 3.23 (1H, sep, J=7 Hz), 4.29 (2H, q, J=7 Hz), 4.59 (2H, q, J=7 Hz), 6.99 (1H, d, J=1 Hz), 7.14 (1H, d, J=1 Hz), 8.06 (1H, s)

EXAMPLE 268

Ethyl 4-(5-bromo-3-pyridyl)-1-ethyl-6-isopropyl-1H-pyrazolo[3,4-b]pyridine-5-carboxylate $^1$H-NMR (CDCl$_3$) δ 1.11 (3H, t, J=8 Hz), 1.39 (6H, d, J=7 Hz), 1.56 (3H, t, J=8 Hz), 3.33 (1H, m), 4.19 (2H, q, J=8 Hz), 4.62 (2H, q, J=8 Hz), 7.82 (1H, s), 7.99 (1H, br s), 8.67 (1H, br s), 8.78 (1H, br s)

EXAMPLE 269

Ethyl 4-(5-bromo-3-pyridyl)-6-cyclopentyl-1-ethyl-1H-pyrazolo[3,4-b]pyridine-5-carboxylate $^1$H-NMR (CDCl$_3$) δ 1.10 (3H, t, J=7 Hz), 1.55 (3H, t, J=7 Hz), 1.64-2.10 (8H, m), 3.44 (1H, tt, J=7,7 Hz), 4.27 (2H, q, J=7 Hz), 4.51 (2H, q, J=7 Hz), 7.81 (1H, s), 8.00 (1H, s), 8.68 (1H, s), 8.80 (1H, s)

EXAMPLE 270

Methyl 4-(2-chloro-4-pyridyl)-6-cyclopropyl-1-ethyl-1H-pyrazolo[3,4-b]pyridine-5-carboxylate $^1$H-NMR (CDCl$_3$) δ 1.08-1.15 (2H, m), 1.28-1.34 (2H, m), 2.28-2.34 (1H, m), 3.70 (3H, s), 4.57 (2H, q, J=6.7 Hz), 1.53 (3H, t, J=6.7 Hz), 7.34 (1H, d, J=5.2 Hz), 7.46 (1H, s), 7.79 (1H, s), 8.54 (1H, d, J=5.2 Hz)

EXAMPLE 271

Methyl 4-(3-chlorophenyl)-1-ethyl-6-(methoxymethyl)-1H-pyrazolo[3,4-b]pyridine-5-carboxylate $^1$H-NMR (CDCl$_3$) δ 1.56 (3H, t, J=8 Hz), 3.40 (3H, s), 3.66 (3H, s), 4.61 (2H, q, J=8 Hz), 4.83 (2H, s), 7.35-7.52 (4H, m), 7.89 (1H, s)

EXAMPLE 272

Ethyl 6-cyclopropyl-1-ethyl-4-(5-methyl-3-pyridyl)-1H-pyrazolo[3,4-b]pyridine-5-carboxylate $^1$H-NMR (CDCl$_3$) δ 1.05-1.12 (2H, m), 1.28-1.34 (2H, m), 1.51 (3H, t, J=7 Hz), 2.22-2.30 (1H, m), 2.44 (3H, s), 3.69 (3H, s), 4.52 (2H, q, J=7 Hz), 7.65 (1H, s), 7.79 (1H, s), 8.56 (2H, s)

EXAMPLE 273

Methyl 4-(5-chloro-3-pyridyl)-1-ethyl-6-(methoxymethyl)-1H-pyrazolo[3,4-b]pyridine-5-carboxylate $^1$H-NMR (CDCl$_3$) δ 1.56 (3H, t, J=8 Hz), 3.40 (3H, s), 3.71 (3H, s), 4.63 (2H, q, J=8 Hz), 4.84 (2H, s), 7.83 (1H, t, J=1 Hz), 7.87 (1H, s), 8.61 (1H, d, J=1 Hz), 8.70 (1H, d, J=1 Hz)

EXAMPLE 274

Ethyl 4-(5-chloro-3-pyridyl)-1-ethyl-6-isopropyl-1H-pyrazolo[3,4-b]pyridine-5-carboxylate $^1$H-NMR (CDCl$_3$) δ 1.11 (3H, t, J=7 Hz), 1.39 (6H, d, J=7 Hz), 1.56 (3H, t, J=7 Hz), 3.32 (1H, sep, J=7 Hz), 4.19 (2H, q, J=7 Hz), 4.62 (2H, q, J=7 Hz), 7.81 (1H, s), 7.84 (1H, t, J=1 Hz), 8.64 (1H, d, J=1 Hz), 8.70 (1H, d, J=1 Hz)

EXAMPLE 275

Ethyl 1-ethyl-4-(5-methyl-3-pyridyl)-6-propyl-1H-pyrazolo[3,4-b]pyridine-5-carboxylate $^1$H-NMR (CDCl$_3$) δ 1.05 (3H, t, J=3 Hz), 1.07 (3H, t, J=7 Hz), 1.56 (3H, t, J=7 Hz), 1.87 (2H, tq, J=7,7 Hz), 2.42 (3H, s), 2.96 (2H, t, J=7 Hz), 4.15 (2H, q, J=7 Hz), 4.60 (2H, q, J=7 Hz), 7.63 (1H, s), 7.82 (1H, s), 8.56 (2H, s)

EXAMPLE 276

Methyl 6-cyclobutyl-1-ethyl-4-(5-methyl-3-pyridyl)-1H-pyrazolo[3,4-b]pyridine-5-carboxylate $^1$H-NMR (CDCl$_3$) δ 1.57 (3H, t, J=7 Hz), 1.90-2.14 (2H, m), 2.26-2.37 (2H, m), 2.44 (3H, s), 2.54-2.68 (2H, m), 3.67 (3H, s), 3.96 (1H, quintet, J=7 Hz), 4.66 (2H, q, J=7 Hz), 7.64 (1H, s), 7.85 (1H, s), 8.59 (2H, s)

EXAMPLE 277

Ethyl 6-(2,2-dimethylpropyl)-1-ethyl-4-(5-methyl-3-pyridyl)-1H-pyrazolo[3,4-b]pyridine-5-carboxylate $^1$H-NMR (CDCl$_3$) δ 0.99 (3H, t, J=7 Hz), 1.01 (9H, s), 1.56 (3H, t, J=7 Hz), 2.43 (3H, s), 3.01 (2H, s), 4.09 (2H, q, J=7 Hz), 4.61 (2H, q, J=7 Hz), 7.61 (1H, s), 7.82 (1H, s), 8.56 (2H, s)

EXAMPLE 278

Methyl 4-(5-chloro-3-pyridyl)-6-cyclopropyl-1-ethyl-1H-pyrazolo[3,4-b]pyridine-5-carboxylate $^1$H-NMR (CDCl$_3$) δ 1.08-1.13 (2H, m), 1.30-1.35 (2H, m), 1.51 (3H, t, J=7 Hz), 2.23-2.32 (1H, m), 3.71 (3H, s), 4.52 (2H, q, J=7 Hz), 7.79 (1H, s), 7.82 (1H, s), 8.62 (1H, s), 8.69 (1H, s)

EXAMPLE 279

Methyl 4-(5-chloro-2-thienyl)-6-cyclopropyl-1-ethyl-1H-pyrazolo[3,4-b]pyridine-5-carboxylate $^1$H-NMR (CDCl$_3$) δ 1.02-1.10 (2H, m), 1.24-1.32 (2H, m), 1.49 (3H, t, J=7 Hz), 2.07-2.18 (1H, m), 3.85 (3H, s), 4.50 (2H, q, J=7 Hz), 7.00 (1H, d, J=4 Hz), 7.15 (1H, d, J=4 Hz), 8.05 (1H, s)

EXAMPLE 280 tert-Butyl 1-ethyl-6-(isopropoxymethyl)-4-(5-methyl-3-pyridyl)-1H-pyrazolo[3,4-b]pyridine-5-carboxylate $^1$H-NMR (CDCl$_3$) δ 1.22 (6H, d, J=7 Hz), 1.31 (9H, s), 1.57 (3H, t, J=7 Hz), 2.43 (3H, s), 3.73 (1H, sep, J=7 Hz), 4.63 (2H, q, J=7 Hz), 4.91 (2H, s), 7.62 (1H, s), 7.80 (1H, s), 8.57 (2H, s)

MS (ESI$^+$) m/z 411(M+1)

EXAMPLE 281

Ethyl 1,6-diethyl-4-(5-methyl-3-pyridyl)-1H-pyrazolo[3,4-b]pyridine-5-carboxylate $^1$H-NMR (CDCl$_3$) δ 1.15 (3H, t, J=7 Hz), 1.40 (3H, t, J=7 Hz), 1.56 (3H, t, J=7 Hz), 2.43 (3H, s), 3.03 (2H, q, J=7 Hz), 4.24 (2H, q, J=7 Hz), 4.61 (2H, q, J=7 Hz), 7.53 (1H, s), 7.82 (1H, s), 8.55 (1H, s)

EXAMPLE 282

Ethyl 1-ethyl-6-(5-methyl-3-isoxazolyl)-4-(5-methyl-3-pyridyl)-1H-pyrazolo[3,4-b]pyridine-5-carboxylate $^1$H-NMR (CDCl$_3$) δ 1.10 (3H, t, J=7 Hz), 1.60 (3H, t, J=7 Hz), 2.45 (3H, s), 2.53 (3H, s), 4.20 (2H, q, J=7 Hz), 4.66 (2H, q, J=7 Hz), 6.67 (1H, s), 7.70 (1H, s), 7.90 (1H, s), 8.59 (1H, s), 8.61 (1H, s)

EXAMPLE 283

Ethyl 1-ethyl-6-(1-ethylpropyl)-4-(5-methyl-3-pyridyl)-1H-pyrazolo[3,4-b]pyridine-5-carboxylate $^1$H-NMR (CDCl$_3$) δ 0.83 (6H, t, J=7 Hz), 1.08 (3H, t, J=7 Hz), 1.55 (3H, t, J=7 Hz), 1.68-1.80 (2H, m), 1.89-2.01 (2H, m), 2.42 (3H, s), 2.81-2.88 (1H, m), 4.14 (2H, q, J=7 Hz), 4.60 (2H, q, J=7 Hz), 7.67 (1H, s), 7.83 (1H, s), 8.54 (1H, d, J=1 Hz), 8.59 (1H, d, J=1 Hz)

EXAMPLE 284

Ethyl 6-(cyclopropylmethyl)-1-ethyl-4-(5-methyl-3-pyridyl)-1H-pyrazolo[3,4-b]pyridine-5-carboxylate $^1$H-NMR (CDCl$_3$) δ 0.30-0.35 (2H, m), 0.49-0.55 (2H, m), 1.03 (3H, t, J=7 Hz), 1.20-1.31 (1H, m), 1.56 (3H, t, J=7 Hz), 2.43 (3H, s), 2.91 (2H, d, J=7 Hz), 4.13 (2H, q, J=7 Hz), 4.61 (2H, q, J=7 Hz), 7.64 (1H, s), 7.83 (1H, s), 8.55 (1H, d, J=1 Hz), 8.57 (1H, d, J=1 Hz)

EXAMPLE 285

Ethyl 4-(5-bromo-3-pyridyl)-1-ethyl-6-phenyl-1H-pyrazolo[3,4-b]pyridine-5-carboxylate $^1$H-NMR (CDCl$_3$) δ 0.90 (3H, t, J=6.6 Hz), 1.58 (3H, t, J=6.6 Hz), 3.96 (2H, q, J=6.6 Hz), 4.67 (2H, q, J=6.6 Hz), 7.45-7.50 (3H, m), 7.63-7.72 (2H, m), 7.90 (1H, s), 8.05 (1H, s), 8.70 (1H, s), 8.81 (1H, s)

EXAMPLE 286

Ethyl 4-(2-chloro-4-pyridyl)-6-cyclopentyl-1-ethyl-1H-pyrazolo[3,4-b]pyridine-5-carboxylate $^1$H-NMR (CDCl$_3$) δ 1.10 (3H, t, J=7 Hz), 1.55 (3H, t, J=7 Hz), 1.66-1.78 (2H, m), 1.86-1.95 (2H, m), 2.02-2.10 (4H, m), 3.45 (1H, quintet, J=7 Hz), 4.18 (2H, q, J=7 Hz), 4.60 (2H, q, J=7 Hz), 7.37 (1H, dd, J=4, 1 Hz), 7.48 (1H, d, J=1 Hz), 7.79 (1H, s), 8.54 (1H, d, J=4 Hz)

EXAMPLE 287

Ethyl 6-(ethoxymethyl)-1-ethyl-4-(5-methyl-3-pyridyl)-1H-pyrazolo[3,4-b]pyridine-5-carboxylate $^1$H-NMR (CDCl$_3$) δ 1.05 (3H, t, J=7 Hz), 1.20 (3H, t, J=7 Hz), 1.55 (3H, t, J=7 Hz), 2.44 (3H, s), 3.55 (2H, q, J=7 Hz), 4.13 (2H, q, J=7 Hz), 4.62 (2H, q, J=7 Hz), 4.89 (2H, s), 7.65 (1H, s), 7.86 (1H, s), 8.57 (2H, t, J=1 Hz)
MS (ESI$^+$) m/z 369(M+1)

EXAMPLE 288

Ethyl 1-ethyl-6-isopropyl-4-{5-[(trimethylsilyl)ethynyl]-3-pyridyl}-1H-pyrazolo[3,4-b]pyridine-5-carboxylate $^1$H-NMR (CDCl$_3$) δ 0.26 (9H, s), 1.10 (3H, t, J=7.1 Hz), 1.38 (6H, d, J=6.8 Hz), 1.55 (3H, t, J=7.2 Hz), 3.32 (1H, h, J=6.8 Hz), 4.16 (2H, q, J=7.1 Hz), 4.61 (2H, q, J=7.2 Hz), 7.80 (1H, s), 7.88 (1H, s), 8.64 (1H, s), 8.75 (1H, s)

EXAMPLE 289

Ethyl 6-cyclopentyl-1-ethyl-4-(5-methyl-3-pyridyl)-1H-pyrazolo[3,4-b]pyridine-5-carboxylate $^1$H-NMR (CDCl$_3$) δ 1.06 (3H, t, J=7 Hz), 1.56 (3H, t, J=7 Hz), 1.65-1.79 (2H, m), 1.82-1.99 (2H, m), 2.02-2.14 (4H, m), 2.44 (3H, s), 3.45 (1H, tt, J=7, 7 Hz), 4.15 (2H, q, J=7 Hz), 4.60 (2H, q, J=7 Hz), 7.64 (1H, s), 7.81 (1H, s), 8.55 (1H, s), 8.57 (1H, s)

EXAMPLE 290

Ethyl 1-ethyl-6-(4-fluorophenyl)-4-(5-methyl-3-pyridyl)-1H-pyrazolo[3,4-b]pyridine-5-carboxylate $^1$H-NMR (CDCl$_3$) δ 0.90 (3H, t, J=6.8 Hz), 1.58 (3H, t, J=6.7 Hz), 2.45 (3H, s), 3.95 (2H, q, J=6.8 Hz), 4.65 (2H, q, J=6.7 Hz), 7.17 (2H, dd, J=7.6, 7.6 Hz), 7.65-7.71 (3H, m), 7.90 (1H, s), 8.59 (1H, s), 8.66 (1H, s)

The following compound(s) was(were) obtained in a similar manner to that of Example 19.

EXAMPLE 291

[1-Ethyl-6-isopropyl-4-(5-methyl-3-pyridyl)-1H-pyrazolo[3,4-b]pyridin-5-yl]methanol $^1$H-NMR (CDCl$_3$) δ 1.42 (6H, d, J=7 Hz), 1.55 (3H, t, J=7 Hz), 2.44 (3H, s), 3.69 (1H, sep, J=7 Hz), 4.60 (2H, q, J=7 Hz), 4.68 (2H, s), 7.66 (1H, s), 7.68 (1H, s), 8.54 (1H, s), 8.58 (1H, s)
MS (ESI$^+$) m/z 311 (M+1)

EXAMPLE 292

[4-(5-Bromo-3-pyridyl)-6-cyclopropyl-1-ethyl-1H-pyrazolo[3,4-b]pyridin-5-yl]methanol $^1$H-NMR (CDCl$_3$) δ 1.12 (2H, m), 1.33 (2H, m), 1.51 (3H, t, J=7.2 Hz), 1.83 (1H, t, J=4.6 Hz), 2.57 (1H, m), 4.53 (2H, q, J=7.2 Hz), 4.81 (2H, d, J=4.5 Hz), 7.67 (1H, s), 8.09 (1H, m), 8.73 (1H, d, J=1.2 Hz), 8.82 (1H, d, J=2.0 Hz).

EXAMPLE 293

[6-(Ethoxymethyl)-1-ethyl-4-(5-methyl-3-pyridyl)-1H-pyrazolo[3,4-b]pyridin-5-yl]methanol $^1$H-NMR (CDCl$_3$) δ 1.32 (3H, t, J=7 Hz), 1.56 (3H, t, J=7 Hz), 2.47 (3H, s), 3.76 (2H, q, J=7 Hz), 3.84 (1H, t, J=7 Hz), 4.60 (2H, q, J=7 Hz), 4.61 (2H, q, J=7 Hz), 4.96 (2H, s), 7.82 (1H, s), 7.87 (1H, d, J=1 Hz), 8.60 (1H, d, J=1 Hz), 8.68 (1H, d, J=1 Hz)
MS (ESI$^+$) m/z 327(M+1)

EXAMPLE 294

[6-Cyclopentyl-1-ethyl-4-(5-methyl-3-pyridyl)-1H-pyrazolo[3,4-b]pyridin-5-yl]methanol $^1$H-NMR (CDCl$_3$) δ 1.56 (3H, t, J=7 Hz), 1.65-1.79 (2H, m), 1.91-2.04 (2H, m), 2.05-2.15 (4H, m), 2.45 (3H, s), 3.77 (1H, tt, J=7, 7 Hz), 4.59 (2H, q, J=7 Hz), 4.70 (2H, s), 7.66 (1H, s), 7.70 (1H, s), 8.56 (1H, s), 8.59 (1H, s)

EXAMPLE 295

[6-Butyl-1-ethyl-4-(5-methyl-3-pyridyl)-1H-pyrazolo[3,4-b]pyridin-5-yl]methanol 1.01 (3H, t, J=7 Hz), 1.50-1.59 (5H, m), 1.84-1.93 (2H, m), 2.44 (3H, s), 3.15 (2H, t, J=7 Hz), 4.59 (2H, q, J=7 Hz), 4.68 (2H, s), 7.65 (1H, s), 7.69 (1H, s), 8.53 (2H, bs)

EXAMPLE 296

[1-Ethyl-6-(4-methoxyphenyl)-4-(5-methyl-3-pyridyl)-1H-pyrazolo[3,4-b]pyridin-5-yl]methanol $^1$H-NMR (CDCl$_3$) δ 1.57 (3H, t, J=7 Hz), 2.47 (3H, s), 3.88 (3H, s), 4.52 (2H, s), 4.62 (2H, q), 7.05 (2H, d), 7.74-7.85 (4H, m), 8.56 (1H, s), 8.70 (1H, s)

EXAMPLE 297

(2E)-3-[1-Ethyl-6-(methoxymethyl)-4-(5-methyl-3-pyridyl)-1H-pyrazolo[3,4-b]pyridin-5-yl]-2-propen-1-ol $^1$H-NMR (CDCl$_3$) δ 1.56 (3H, t, J=6 Hz), 2.42 (3H, s), 3.50 (3H, s), 4.26 (2H, br), 4.62 (2H, q, J=6 Hz), 4.71 (2H, s), 5.75 (1H, td, J=3,13 Hz), 6.68 (1H, d, J=13 Hz), 7.59 (1H, s), 7.75 (1H, s), 8.49 (2H, s)

EXAMPLE 298

(2E)-3-[1-Ethyl-6-(methoxymethyl)-4-(5-methyl-3-pyridyl)-1H-pyrazolo[3,4-b]pyridin-5-yl]-2-propen-1-ol $^1$H-NMR (CDCl$_3$) δ 1.56 (3H, t, J=7 Hz), 2.42 (3H, s), 3.51 (3H, s), 4.17 (2H, t, J=3 Hz), 4.62 (2H, q, J=7 Hz), 4.71 (2H, s), 5.76 (1H, td, J=11,3 Hz), 6.69 (1H, d, J=11 Hz), 7.60 (1H, s), 7.76 (1H, s), 8.49 (2H, s)

EXAMPLE 299

[4-(2-Chloro-4-pyridyl)-1-ethyl-6-phenyl-1H-pyrazolo[3,4-b]pyridin-5-yl]methanol $^1$H-NMR (CDCl$_3$) δ 1.56 (3H, t, J=8 Hz), 1.75 (1H, t, J=5 Hz), 4.48 (2H, d, J=5 Hz), 4.64 (2H, q, J=8 Hz), 7.48-7.58 (3H, m), 7.69 (1H, br s), 7.71-7.78 (2H, m), 7.80 (1H, s), 8.59 (1H, d, J=6 Hz)

EXAMPLE 300

[1-Ethyl-6-phenyl-4-(3-pyridyl)-1H-pyrazolo[3,4-b]pyridin-5-yl]methanol $^1$H-NMR (CDCl$_3$) δ 1.56 (3H, t, J=8 Hz), 4.50 (2H, br s), 4.64 (2H, q, J=8 Hz), 7.43-7.59 (4H, m), 7.74-7.83 (2H, m), 8.06 (1H, m), 8.87 (1H, dd, J=7, 1 Hz), 8.93 (1H, d, J=1 Hz)

EXAMPLE 301

[4-(5-Chloro-2-thienyl)-1-ethyl-6-phenyl-1H-pyrazolo[3,4-b]pyridin-5-yl]methanol $^1$H-NMR (CDCl$_3$) δ 1.54 (3H, t, J=8 Hz), 1.81 (1H, t, J=5 Hz), 4.55-4.65 (4H, m), 7.09 (1H, d, J=5 Hz), 7.45-7.56 (4H, m), 7.70-7.77 (2H, m), 8.11 (1H, s)

EXAMPLE 302

[4-(5-Chloro-3-pyridyl)-1-ethyl-6-phenyl-1H-pyrazolo[3,4-b]pyridin-5-yl]methanol $^1$H-NMR (CDCl$_3$) δ 1.57 (3H, t, J=7 Hz), 1.73 (1H, t, J=5 Hz), 4.48 (2H, d, J=5 Hz), 4.65 (2H, q, J=7 Hz), 7.50-7.54 (3H, m), 7.75-7.78 (2H, m), 7.83 (1H, s), 8.12 (1H, t, J=1 Hz), 8.74 (1H, d, J=1 Hz), 8.82 (1H, d, J=1 Hz)

EXAMPLE 303

(1-Ethyl-4,6-diphenyl-1H-pyrazolo[3,4-b]pyridin-5-yl)methanol

1H-NMR (CDCl3); 1.52-1.61 (4H, m), 4.54 (1H, d, J=5 Hz), 4.62 (2H, q, J=8 Hz), 7.45-7.66 (8H, m), 7.72-7.80 (3H, m)

EXAMPLE 304

[1-Ethyl-6-phenyl-4-(3-quinolinyl)-1H-pyrazolo[3,4-b]pyridin-5-yl]methanol $^1$H-NMR (CDCl$_3$) δ 1.59 (3H, t, J=6.6 Hz), 1.91 (1H, t, J=3.4 Hz), 4.55 (2H, d, J=3.4 Hz), 4.65 (2H, q, J=6.6 Hz), 7.46-7.60 (3H, m), 7.67 (1H, dd, J=7.8,7.8 Hz), 7.77-7.89 (4H, m), 7.95 (1H, d, J=7.8 Hz), 8.22 (1H, d, J=7.8 Hz), 8.55 (1H, s), 9.21 (1H, s)

EXAMPLE 305

[4-(2-chloro-4-pyridyl)-1-ethyl-6-isopropyl-1H-pyrazolo[3,4-b]pyridin-5-yl]methanol $^1$H-NMR (CDCl$_3$) δ 1.44 (6H, d, J=6 Hz), 1.55 (3H, t, J=7 Hz), 1.70 (1H, t, J=5 Hz), 3.65 (1H, qq, J=6 Hz), 4.60 (2H, q, J=7 Hz), 4.66 (2H, d, J=5 Hz), 7.44 (1H, d, J=6 Hz), 7.55 (1H, s), 7.67 (1H, s), 8.55 (1H, d, J=6 Hz)

EXAMPLE 306

[1-Ethyl-6-isobutyl-4-(5-methyl-3-pyridyl)-1H-pyrazolo[3,4-b]pyridin-5-yl]methanol $^1$H-NMR (CDCl$_3$) δ 1.05(6H, d, J=7 Hz), 1.52 (3H, t, J=7 Hz), 2.22-2.32 (1H, m), 2.45 (3H, s), 3.05 (2H, d, J=7 Hz), 4.55 (2H, q, J=7 Hz), 4.69 (2H, s), 7.72 (1H, s), 7.99 (1H, s), 8.58 (1H, d, J=1 Hz), 8.61 (1H, d, J=1 Hz)

EXAMPLE 307

[1-Ethyl-4-(5-methoxy-3-pyridyl)-6-phenyl-1H-pyrazolo[3,4-b]pyridin-5-yl]methanol $^1$H-NMR (CDCl$_3$) δ 1.56 (3H, t, J=7 Hz), 2.49 (3H, s), 4.50 (2H, s), 4.63 (2H, q, J=7 Hz), 7.50-7.54(3H, m), 7.65 (1H, t, J=1 Hz), 7.75-7.80 (2H, m), 7.85 (1H, s), 8.60 (1H, d, J=1 Hz), 8.70 (1H, d, J=1 Hz)

EXAMPLE 308

(2E)-3-[1-Ethyl-4-(5-methyl-3-pyridyl)-6-phenyl-1H-pyrazolo[3,4-b]pyridin-5-yl]-2-propen-1-ol $^1$H-NMR (CDCl$_3$) δ 1.56 (3H, t), 2.45 (3H, s), 3.93 (2H, d, J=4 Hz), 4.62 (2H, q, J=7 Hz), 5.32 (1H, td, J=11,4 Hz), 6.44 (1H, d, J=11 Hz), 7.40-7.50 (3H, m), 7.56-7.67 (3H, m), 7.76 (1H, s), 8.50 (2H, s)

EXAMPLE 309

[1-Ethyl-6-(4-fluorophenyl)-4-(5-methyl-3-pyridyl)-1H-pyrazolo[3,4-b]pyridin-5-yl]methanol $^1$H-NMR (CDCl$_3$) δ 1.55 (3H, t, J=7 Hz), 2.46 (3H, s), 4.47 (2H, s), 4.61 (2H, q, J=7 Hz), 7.20 (2H, dd, J=8,8 Hz), 7.77-7.98 (4H, m), 8.58 (1H, br), 8.71 (1H, br)

EXAMPLE 310

[4-(5-Chloro-2-thienyl)-1-ethyl-6-isopropyl-1H-pyrazolo[3,4-b]pyridin-5-yl]methanol $^1$H-NMR (CDCl$_3$) δ 1.40 (6H, d, J=7 Hz), 1.54 (3H, t, J=7 Hz), 3.64 (1H, sep, J=7 Hz), 4.59 (2H, q, J=7 Hz), 4.84 (2H, s), 7.05 (1H, d, J=4 Hz), 7.21 (1H, d, J=4 Hz), 7.95 (1H, s)

EXAMPLE 311

[4-(5-Bromo-3-pyridyl)-6-cyclopentyl-1-ethyl-1H-pyrazolo[3,4-b]pyridin-5-yl]methanol $^1$H-NMR (CDCl$_3$) δ 1.55 (3H, t, J=7 Hz), 1.60-2.13 (8H, m), 3.77 (1H, tt, J=7,7 Hz), 4.58 (2H, q, J=7 Hz), 4.70 (2H, s), 7.67 (1H, s), 8.10 (1H, s), 8.72 (1H, s), 8.80 (1H, s)

EXAMPLE 312

[4-(5-Bromo-3-pyridyl)-1-ethyl-6-isopropyl-1H-pyrazolo[3,4-b]pyridin-5-yl]methanol $^1$H-NMR (CDCl$_3$) δ 1.41 (6H, d, J=7 Hz), 1.56 (3H, t, J=8 Hz), 1.72 (1H, br t, J=5 Hz), 3.65 (1H, m), 4.60 (2H, q, J=8 Hz), 4.68 (2H, br d, J=5 Hz), 7.69 (1H, s), 8.09 (1H, br s), 8.73 (1H, br s), 8.80 (1H, br s)

EXAMPLE 313

[6-Cyclopropyl-1-ethyl-4-(5-methyl-3-pyridyl)-1H-pyrazolo[3,4-b]pyridin-5-yl]methanol $^1$H-NMR (CDCl$_3$) δ 1.09-1.15 (2H, m), 1.30-1.34 (2H, m), 1.51 (3H, t, J=7 Hz), 2.46 (3H, s), 2.55-2.63 (1H, m), 4.63 (2H, q, J=7 Hz), 4.83 (2H, s), 7.67 (1H, s), 7.69 (1H, s), 8.58 (1H, s), 8.59 (1H, s)

EXAMPLE 314

[4-(2-Chloro-4-pyridyl)-6-cyclopropyl-1-ethyl-1H-pyrazolo[3,4-b]pyridin-5-yl]methanol $^1$H-NMR (CDCl$_3$) δ 1.08-1.15 (2H, m), 1.28-1.35 (2H, m), 1.50 (3H, t, J=7 Hz), 2.51-2.61 (1H, m), 4.51 (2H, q, J=7 Hz), 4.79 (2H, s), 7.42 (1H, d, J=4 Hz), 7.54 (1H, s), 7.65 (1H, s), 8.54 (1H, d, J=4 Hz)

EXAMPLE 315

(2E)-3-[4-(2-Chloro-4-pyridyl)-6-cyclopropyl-1-ethyl-1H-pyrazolo[3,4-b]pyridin-5-yl]-2-propen-1-ol $^1$H-NMR (CDCl$_3$) δ 1.04-1.09 (2H, m), 1.25-1.31 (2H, m), 1.52 (3H, t, J=6.9 Hz), 2.35-2.44 (1H, m), 4.20 (2H, d, J=5.8 Hz), 4.51 (2H, q, J=6.9 Hz), 5.70 (1H, dd, J=13.2, 5.8 Hz), 6.75 (1H, d, J=13.2 Hz), 7.27 (1H, d, J=5.4 Hz), 7.40 (1H, s), 7.64 (1H, s), 8.48 (1H, d, J=5.4 Hz)

EXAMPLE 316

[4-(3-Chlorophenyl)-1-ethyl-6-(methoxymethyl)-1H-pyrazolo[3,4-b]pyridin-5-yl]methanol $^1$H-NMR (CDCl$_3$) δ 1.56 (3H, t, J=8 Hz), 3.55 (3H, s), 3.61 (1H, t, J=8 Hz), 4.56-4.66 (4H, m), 4.91 (2H, s), 7.47-7.58 (3H, m), 7.64 (1H, br s), 7.81 (1H, s)

EXAMPLE 317

[4-(5-Bromo-3-pyridyl)-1-ethyl-6-(methoxymethyl)-1H-pyrazolo[3,4-b]pyridin-5-yl]methanol $^1$H-NMR (CDCl$_3$) δ 1.57 (3H, t, J=7 Hz), 3.56 (3H, s), 3.59 (1H, t, J=7 Hz), 4.59 (2H, d, J=7 Hz), 4.63 (2H, q, J=7 Hz), 4.92 (2H, s), 7.83 (1H, s), 8.23 (1H, t, J=1 Hz), 8.83 (1H, d, J=1 Hz), 8.85 (1H, d, J=1 Hz)

EXAMPLE 318

[1-Ethyl-4-(5-methyl-3-pyridyl)-6-propyl-1H-pyrazolo[3,4-b]pyridin-5-yl]methanol $^1$H-NMR (CDCl$_3$) δ 1.10 (3H, t, J=7 Hz), 1.53 (3H, t, J=7 Hz), 1.94 (2H, tq, J=7,7 Hz), 2.41 (2H, s), 3.12 (2H, t, J=7 Hz), 4.58 (2H, q, J=7 Hz), 4.67 (2H, s), 7.65 (1H, s), 7.69 (1H, s), 8.48 (1H, s), 8.54 (1H, s)

EXAMPLE 319

[4-(5-chloro-3-pyridyl)-1-ethyl-6-(methoxymethyl)-1H-pyrazolo[3,4-b]pyridin-5-yl]methanol $^1$H-NMR (CDCl$_3$) δ 1.57 (3H, t, J=8 Hz), 3.54-3.61 (4H, m), 4.55-4.68 (4H, m), 4.92 (2H, s), 7.83 (1H, s), 8.07 (1H, t, J=1 Hz), 8.73 (1H, d, J=1 Hz), 8.77 (1H, d, J=1 Hz)

EXAMPLE 320

[4-(5-Chloro-3-pyridyl)-1-ethyl-6-isopropyl-1H-pyrazolo[3,4-b]pyridin-5-yl]methanol $^1$H-NMR (CDCl$_3$) δ 1.42 (6H, d, J=7 Hz), 1.57 (3H, t, J=7 Hz), 1.72 (1H, t, J=7 Hz), 3.67 (1H, sep, J=7 Hz), 4.61 (2H, q, J=7 Hz), 4.68 (2H, d, J=7 Hz), 7.69 (1H, s), 7.95 (1H, t, J=1 Hz), 8.70 (1H, d, J=1 Hz), 8.72 (1H, d, J=1 Hz)

EXAMPLE 321

[6-Cyclobutyl-1-ethyl-4-(5-methyl-3-pyridyl)-1H-pyrazolo [3,4-b]pyridin-5-yl]methanol $^1$H-NMR (CDCl$_3$) δ 1.42 (6H, d, J=7 Hz), 1.55 (3H, t, J=7 Hz), 2.44 (3H, s), 3.69 (1H, sep, J=7 Hz), 4.60 (2H, q, J=7 Hz), 4.68 (2H, s), 7.66 (1H, s), 7.68 (1H, s), 8.54 (1H, s), 8.58 (1H, s)

MS (ESI$^+$) m/z 311 (M+1)

EXAMPLE 322

[4-(5-Chloro-3-pyridyl)-6-cyclopropyl-1-ethyl-1H-pyrazolo[3,4-b]pyridin-5-yl]methanol $^1$H-NMR (CDCl$_3$) δ 1.09-1.15 (2H, m), 1.30-1.35 (2H, m), 1.51 (3H, t, J=7 Hz), 2.53-2.63 (1H, m), 4.51 (2H, q, J=7 Hz), 4.80 (2H, s), 7.66 (1H, s), 7.93 (1H, s), 8.69 (2H, s)

EXAMPLE 323

[4-(5-Chloro-2-thienyl)-6-cyclopropyl-1-ethyl-1H-pyrazolo[3,4-b]pyridin-5-yl]methanol $^1$H-NMR (CDCl$_3$) δ 1.06-1.15 (2H, m), 1.26-1.35 (2H, m), 1.50 (3H, t, J=7 Hz), 1.76 (1H, t, J=6 Hz), 2.50-2.60 (1H, m), 4.50 (2H, q, J=7 Hz), 5.00 (2H, d, J=6 Hz), 7.05 (1H, d, J=4 Hz), 7.25 (1H, d, J=4 Hz), 7.94 (1H, s)

EXAMPLE 324

[1-Ethyl-6-isopropyl-4-(2-methyl-4-pyridyl)-1H-pyrazolo[3,4-b]pyridin-5-yl]methanol $^1$H-NMR (CDCl$_3$) δ 1.42 (6H, d, J=7 Hz), 1.55 (3H, t, J=7 Hz), 2.66 (3H, s), 3.67 (1H, sep, J=7 Hz), 4.61 (2H, q, J=7

Hz), 4.67 (2H, s), 7.25 (1H, dd, J=4, 1 Hz), 7.32 (1H, d, J=1 Hz), 7.64 (1H, s), 8.64 (1H, d, J=4 Hz)
MS (ESI$^+$) m/z 311(M+1)

EXAMPLE 325

[4-(2-Chloro-4-pyridyl)-6-cyclopentyl-1-ethyl-1H-pyrazolo[3,4-b]pyridin-5-yl]methanol $^1$H-NMR (CDCl$_3$) δ 1.54 (3H, t, J=7 Hz), 1.69-1.81 (2H, m), 1.93-2.00 (2H, m), 2.05-2.14 (4H, m), 3.75 (1H, quintet, J=7 Hz), 4.59 (2H, q, J=7 Hz), 4.69 (2H, d, J=4 Hz), 7.44 (1H, dd, J=4, 1 Hz), 7.56 (1H, s), 7.66 (1H, s), 8.56 (1H, d, J=4 Hz)

EXAMPLE 326

[4-(4-Amino-3,5-dichlorophenyl)-6-cyclopropyl-1-ethyl-1H-pyrazolo[3,4-b]pyridin-5-yl]methanol $^1$H-NMR (CDCl$_3$) δ 1.10 (2H, m), 1.30 (2H, m), 1.49 (3H, t, J=7.1 Hz), 1.71 (1H, t, J=5.0 Hz), 2.56 (1H, m), 4.50 (2H, q, J=7.2 Hz), 4.66 (2H, br s), 4.86 (2H, d, J=5.1 Hz), 7.43 (2H, s), 7.71 (1H, s)

EXAMPLE 327

(1-Ethyl-6-isopropyl-4-{5-[(trimethylsilyl)ethynyl]-3-pyridyl}-1H-pyrazolo[3,4-b]pyridin-5-yl)methanol $^1$H-NMR (CDCl$_3$) δ 0.26 (9H, s), 1.41 (6H, d, J=6.7 Hz), 1.54 (3H, t, J=6.5 Hz), 3.67 (1H, h, J=6.7 Hz), 4.59 (2H, q, J=6.5 Hz), 4.65 (2H, s), 7.65 (1H, s), 7.93 (1H, s), 8.68 (1H, s), 8.77 (1H, s)

EXAMPLE 328

[6-(2,2-Dimethylpropyl)-1-ethyl-4-(5-methyl-3-pyridyl)-1H-pyrazolo[3,4-b]pyridin-5-yl]methanol $^1$H-NMR (CDCl$_3$) δ 1.11 (9H, s), 1.55 (3H, t, J=7 Hz), 2.45 (3H, s), 3.09 (2H, s), 4.59 (2H, q, J=7 Hz), 4.71 (2H, s), 7.66 (1H, s), 7.69 (1H, s), 8.57 (2H, s)
MS (ESI$^+$) m/z 339(M+1)

EXAMPLE 329

[4-(5-Bromo-3-pyridyl)-1-ethyl-6-phenyl-1H-pyrazolo[3,4-b]pyridin-5-yl]methanol $^1$H-NMR (CDCl$_3$) δ 1.55 (3H, t, J=6.7 Hz), 1.90 (1H, s), 4.48 (2H, s), 4.55 (2H, q, J=6.7 Hz), 7.45-7.58 (3H, m), 7.72-7.78 (2H, m), 7.80 (1H, s), 8.25 (1H, s), 8.32 (1H, s), 8.34 (1H, s)

EXAMPLE 330

[1-Ethyl-6-(1-ethylpropyl)-4-(5-methyl-3-pyridyl)-1H-pyrazolo[3,4-b]pyridin-5-yl]methanol $^1$H-NMR (CDCl$_3$) δ 0.86 (6H, t, J=7 Hz), 1.54 (3H, t, J=7 Hz), 1.75-1.89 (2H, m), 1.91-2.05 (2H, m), 2.45 (3H, s), 3.18-3.27 (1H, m), 4.59 (2H, q, J=7 Hz), 4.67 (2H, s), 7.68 (1H, s), 7.73 (1H, s), 8.57 (1H, d, J=1 Hz), 8.61 (1H, d, J=1 Hz)

EXAMPLE 331

[6-(Cyclopropylmethyl)-1-ethyl-4-(5-methyl-3-pyridyl)-1H-pyrazolo[3,4-b]pyridin-5-yl]methanol $^1$H-NMR (CDCl$_3$) δ 0.36-0.41 (2H, m), 0.55-0.61 (2H, m), 1.30-1.40 (1H, m), 1.55 (3H, t, J=7 Hz), 2.49 (3H, s), 3.10 (2H, d, J=7 Hz), 4.61 (2H, q, J=7 Hz), 4.69 (2H, s), 7.70 (1H, s), 7.71 (1H, s), 8.58 (1H, s), 8.60 (1H, s)
MS (ESI$^+$) m/z 323(M+1)

EXAMPLE 332

[1,6-Diethyl-4-(5-methyl-3-pyridyl)-1H-pyrazolo[3,4-b]pyridin-5-yl]methanol $^1$H-NMR (CDCl$_3$) δ 1.46 (3H, t, J=7 Hz), 1.55 (3H, t, J=7 Hz), 2.42 (3H, s), 3.20 (2H, q, J=7 Hz), 4.59 (2H, q, J=7 Hz), 4.67 (2H, s), 7.65 (1H, s), 7.68 (1H, s), 8.46 (1H, s), 8.53 (1H, s)

EXAMPLE 333

(4-Cyclohexyl-6-cyclopropyl-1-ethyl-1H-pyrazolo[3,4-b]pyridin-5-yl)methanol $^1$H-NMR (CDCl$_3$) δ 1.04 (2H, m), 1.22 (2H, m), 1.45-1.55 (3H, m), 1.47 (3H, t, J=7.3 Hz), 1.84-1.97 (7H, m), 2.47 (1H, m), 3.25 (1H, m), 4.46 (2H, q, J=7.3 Hz), 5.04 (2H, d, J=5.5 Hz), 8.09 (1H, s)

EXAMPLE 334

[1-Ethyl-6-(2-fluorophenyl)-4-(5-methyl-3-pyridyl)-1H-pyrazolo[3,4-b]pyridin-5-yl]methanol $^1$H-NMR (CDCl$_3$) δ 1.55 (3H, t, J=6.7 Hz), 2.47 (3H, s), 4.45 (2H, s), 4.62 (2H, q, J=6.7 Hz), 7.20-7.35 (3H, m), 7.45-7.60 (2H, m), 7.83 (1H, s), 7.86 (1H, s), 8.58 (1H, s), 8.70 (1H, s)

EXAMPLE 335

To a solution of 1-ethyl-6-phenyl-4-(tetrahydro-2H-pyran-4-yl)-1H-pyrazolo[3,4-b]pyridine-5-carbonitrile (354 mg) in toluene (7 ml) was added diisobutylaluminium hydride toluene solution (1.5M, 1.0 ml) dropwise at −78° C. The mixture was stirred for 5 hours at same temperature. The reaction was quenched with 1N HCl. The organic layer was separated, washed with water and brine and dried over MgSO$_4$. The solvent was evaporated and the residue was purified with silica-gel column chromatography. 1-Ethyl-6-phenyl-4-(tetrahydro-2H-pyran-4-yl)-1H-pyrazolo[3,4-b]pyridine-5-carbaldehyde (229 mg) was obtained as a slightly yellow solid.
$^1$H-NMR (CDCl$_3$) δ 1.57 (3H, t, J=6.6 Hz), 1.89 (2H, d, J=13.2 Hz), 2.26-2.52 (2H, m), 3.65 (2H, dd, J=13.2, 13.2 Hz), 4.12-4.21 (2H, m), 4.30-4.41 (1H, m), 4.62 (2H, q, J=6.6 Hz), 7.50-7.61 (5H, m), 8.45 (1H, s), 10.02 (1H, s)
The following compound(s) was(were) obtained in a similar manner to that of Example 335.

EXAMPLE 336

4-Cyclohexyl-1-ethyl-6-phenyl-1H-pyrazolo[3,4-b]pyridine-5-carbaldehyde $^1$H-NMR (CDCl$_3$) δ 1.40-1.63 (4H, m), 1.57 (3H, t, J=6.6 Hz), 1.81-2.05 (6H, m), 3.96-4.06 (1H, m), 4.60 (2H, q, J=6.6 Hz), 7.48-7.61 (5H, m), 8.39 (1H, s), 10.01 (1H, s)

EXAMPLE 337

1-Ethyl-4-isopropyl-6-phenyl-1H-pyrazolo[3,4-b]pyridine-5-carbaldehyde $^1$H-NMR (CDCl$_3$) δ 1.57 (3H, t, J=6.7 Hz), 1.59 (6H, d, J=6.7 Hz), 4.37 (1H, h, J=6.7 Hz), 4.61 (2H, q, J=6.7 Hz), 7.49-7.60 (5H, m), 8.35 (1H, s), 10.00 (1H, s)

EXAMPLE 338

A solution of ethyl (2E)-3-[1-ethyl-6-isopropyl-4-(5-methyl-3-pyridyl)-1H-pyrazolo[3,4-b]pyridin-5-yl]acrylate (268 mg) in MeOH-AcOH (90:10, 10 ml) was hydrogenated (3 atm) over palladium hydroxide (38 mg) at room temperature for 8 hours. The reaction mixture was filtered through celite pad and the filtrate was concentrated in vacuo. The residue was dissolved in EtOAc and washed with saturated aqueous NaHCO$_3$, water, brine, dried over anhydrous MgSO$_4$ and concentrated in vacuo. The residue was purified by flash column chromatography on silica gel eluting with a mixture of EtOAc and n-hexane (1:2) to give ethyl 3-[1-ethyl-6-isopropyl-4-(5-methyl-3-pyridyl)-1H-pyrazolo[3,4-b]pyridin-5-yl]propanoate (123 mg) as a colorless oil.

$^1$H-NMR (CDCl$_3$) δ 1.21 (3H, t, J=7 Hz), 1.39 (6H, d, J=7 Hz), 1.55 (3H, t, J=7 Hz), 2.39 (2H, t, J=7 Hz), 2.47 (3H, s), 2.99 (2H, t, J=7 Hz), 3.40 (1H, sep, J=7 Hz), 4.18 (2H, q, J=7 Hz), 4.58 (2H, q, J=7 Hz), 7.51 (1H, s), 7.57 (1H, s), 8.47 (1H, d, J=1 Hz), 8.60 (1H, d, J=1 Hz)

The following compound(s) was(were) obtained in a similar manner to that of Example 338.

EXAMPLE 339

Ethyl 3-[6-(cyclopropylmethyl)-1-ethyl-4-(5-methyl-3-pyridyl)-1H-pyrazolo[3,4-b]pyridin-5-yl]propanoate $^1$H-NMR (CDCl$_3$) δ 0.34-0.38 (2H, m), 0.55-0.60 (2H, m), 1.20 (3H, t, J=7 Hz), 1.27-1.35 (1H, m), 1.55 (3H, t, J=7 Hz), 2.35 (2H, t, J=7 Hz), 2.45 (3H, s), 2.94 (2H, d, J=7 Hz), 3.02 (2H, t, J=7 Hz), 4.07 (2H, q, J=7 Hz), 4.58 (2H, q, J=7 Hz), 7.50 (1H, t, J=1 Hz), 7.53 (1H, s), 8.45 (1H, d, J=1 Hz), 8.57 (1H, d, J=1 Hz)

MS (ESI$^+$) m/z 393(M+1)

EXAMPLE 340

Ethyl 3-[1-ethyl-6-phenyl-4-(3-pyridyl)-1H-pyrazolo[3,4-b]pyridin-5-yl]propanoate $^1$H-NMR (CDCl$_3$) δ 1.06 (3H, t, J=8 Hz), 1.55 (3H, t, J=8 Hz), 2.01-2.11 (2H, m), 3.00-3.10 (2H, m), 3.89 (2H, q, J=8 Hz), 4.60 (2H, q, J=8 Hz), 7.43-7.59 (7H, m), 7.65 (1H, s), 7.80 (1H, m), 8.71-8.79 (2H, m)

EXAMPLE 341

3-(1-Ethyl-4,6-diphenyl-1H-pyrazolo[3,4-b]pyridin-5-yl)propanoic acid $^1$H-NMR (CDCl$_3$) δ 1.54 (3H, t, J=8 Hz), 2.09 (2H, br q, J=8 Hz), 3.04 (2H, br q, J=8 Hz), 4.59 (2H, q, J=8 Hz), 7.27 (1H, s), 7.39-7.60 (8H, m), 7.67 (1H, s)

EXAMPLE 342

3-[1-Ethyl-6-(2-fluorophenyl)-4-(5-methyl-3-pyridyl)-1H-pyrazolo[3,4-b]pyridin-5-yl]propanoic acid $^1$H-NMR (CDCl$_3$) δ 1.53 (3H, t, J=7 Hz), 2.12 (2H, t, J=7 Hz), 2.44 (3H, s), 2.96 (2H, t, J=7 Hz), 4.58 (2H, q, J=7 Hz), 7.15-7.35 (2H, m), 7.40-7.51 (2H, m), 7.64 (2H, s), 8.48 (1H, s), 8.53 (1H, s)

EXAMPLE 343

3-[6-Cyclopropyl-1-ethyl-4-(5-methyl-3-pyridyl)-1H-pyrazolo[3,4-b]pyridin-5-yl]propanoic acid $^1$H-NMR (CDCl$_3$) δ 1.07-1.13 (2H, m), 1.29-1.35 (2H, m), 1.51 (3H, t, J=7 Hz), 2.26-2.34 (1H, m), 2.43 (3H, s), 2.65 (2H, t, J=7 Hz), 3.15 (2H, t, J=7 Hz), 4.50 (2H, q, J=7 Hz), 7.48 (1H, s), 7.55 (1H, s), 8.44 (1H, s), 8.53 (1H, s)

mp. 205-207° C.

EXAMPLE 344

3-[1-Ethyl-6-isobutyl-4-(5-methyl-3-pyridyl)-1H-pyrazolo[3,4-b]pyridin-5-yl]propanoic acid $^1$H-NMR (CDCl$_3$) δ 1.04 (6H, d, J=7 Hz), 1.53 (3H, t, J=7 Hz), 2.39-2.47 (3H, m), 2.49 (3H, s), 2.85 (2H, d, J=7 Hz), 3.02 (2H, t, J=7 Hz), 4.58 (2H, q, J=7 Hz), 7.51 (1H, s), 7.68 (1H, s), 8.50 (1H, d, J=1 Hz), 8.59 (1H, d, J=1 Hz)

MS (ESI$^+$) m/z 367(M+1)

mp. 190-191° C.

EXAMPLE 345

3-[1-Ethyl-6-(2-fluorophenyl)-4-(5-methyl-3-pyridyl)-1H-pyrazolo[3,4-b]pyridin-5-yl]propanoic acid $^1$H-NMR (CDCl$_3$) δ 1.55 (3H, t, J=6.8 Hz), 2.13 (3H, t, J=6.4 Hz), 2.45 (3H, s), 2.96 (2H, t, J=6.4 Hz), 4.58 (2H, q, J=6.8 Hz), 7.17-7.35 (2H, m), 7.40-7.55 (2H, m), 7.64 (2H, s), 8.47 (1H, s), 8.53 (1H, s)

EXAMPLE 346

3-[1-Ethyl-6-(1-ethylpropyl)-4-(5-methyl-3-pyridyl)-1H-pyrazolo[3,4-b]pyridin-5-yl]propanoic acid $^1$H-NMR (CDCl$_3$) δ 0.86 (6H, t, J=7 Hz), 1.53 (3H, t, J=7 Hz), 1.73-1.84 (2H, m), 1.89-2.00 (2H, m), 2.44 (3H, s), 2.51 (2H, t, J=7 Hz), 2.94-3.05 (3H, m), 4.67 (2H, q, J=7 Hz), 7.50 (1H, s), 7.57 (1H, s), 8.45 (1H, s), 8.55 (1H, s)

MS (ESI$^+$) m/z 381(M+1)

mp. 144-145° C.

EXAMPLE 347

3-(4-Cyclohexyl-1-ethyl-6-phenyl-1H-pyrazolo[3,4-b]pyridin-5-yl)propanoic acid $^1$H-NMR (CDCl$_3$) δ 1.38-1.57 (2H, m), 1.49 (3H, t, J=6.5 Hz), 1.80-2.10 (8H, m), 2.38 (2H, t, J=9.5 Hz), 3.04 (2H, t, J=9.5 Hz), 3.06-3.14 (1H, m), 4.56 (2H, q, J=6.5 Hz), 7.34-7.51 (5H, m), 8.20 (1H, s)

EXAMPLE 348

3-[1-Ethyl-6-(5-methyl-3-isoxazolyl)-4-(5-methyl-3-pyridyl)-1H-pyrazolo[3,4-b]pyridin-5-yl]propanoic acid $^1$H-NMR (CDCl$_3$) δ 1.58 (3H, t, J=7 Hz), 2.46 (3H, s), 2.50 (2H, t, J=8 Hz), 2.56 (3H, s), 3.32-3.48 (2H, m), 4.61 (2H, q, J=7 Hz), 6.76 (1H, s), 7.55 (1H, s), 7.62 (1H, s), 8.45 (1H, s), 8.57 (1H, s)

EXAMPLE 349

3-[6-(2,2-Dimethylpropyl)-1-ethyl-4-(5-methyl-3-pyridyl)-1H-pyrazolo[3,4-b]pyridin-5-yl]propanoic acid $^1$H-NMR (CDCl$_3$) δ 1.09 (9H, s), 1.54 (3H, t, J=7 Hz), 2.42 (2H, t, J=7 Hz), 2.44 (3H, s), 2.93 (2H, s), 3.07 (2H, t, J=7 Hz), 4.58 (2H, q, J=7 Hz), 7.51 (1H, s), 7.57 (1H, s), 8.44 (1H, d, J=1 Hz), 8.55 (1H, d, J=1 Hz)
MS (ESI$^+$) m/z 381(M+1)
mp. 221-223° C.

EXAMPLE 350

Ethyl 3-[6-butyl-1-ethyl-4-(5-methyl-3-pyridyl)-1H-pyrazolo[3,4-b]pyridin-5-yl]propanoate $^1$H-NMR (CDCl$_3$) δ 1.01 (3H, t, J=7 Hz), 1.20 (3H, t, J=7 Hz), 1.45-1.54 (2H, m), 1.54 (3H, t, J=7 Hz), 1.78-1.91 (2H, m), 2.36 (2H, t, J=7 Hz), 2.46 (3H, s), 2.94-3.02 (4H, m), 4.06 (2H, q, J=7 Hz), 4.58 (2H, q, J=7 Hz), 7.52 (1H, s), 7.56 (1H, s), 8.44 (1H, s), 8.59 (1H, s)

EXAMPLE 351

3-[1-Ethyl-6-isopropyl-4-(2-methyl-4-pyridyl)-1H-pyrazolo[3,4-b]pyridin-5-yl]propanoic acid $^1$H-NMR (CDCl$_3$) δ 1.40 (6H, d, J=7 Hz), 1.57 (3H, t, J=7 Hz), 2.45 (2H, t, J=7 Hz), 2.66 (3H, s), 3.00 (2H, t, J=7 Hz), 3.37-3.46 (1H, m), 4.58 (2H, q, J=7 Hz), 7.17 (1H, d, J=4 Hz), 7.18 (1H, s), 7.50(1H, s), 8.68 (1H, d, J=4 Hz)
MS (ESI$^+$) m/z 353(M+1)
mp. 187-189° C.

EXAMPLE 352

3-[6-Cyclopentyl-ethyl-4-(5-methyl-3-pyridyl)-1H-pyrazolo[3,4-b]pyridin-5-yl]propanoic acid $^1$H-NMR (CDCl$_3$) δ 1.54 (3H, t, J=7 Hz), 1.69-1.79 (2H, m), 1.86-2.04 (2H, m), 2.05-2.12 (4H, m), 2.44 (3H, s), 2.53 (2H, t, J=8 Hz), 3.05 (2H, t, J=8 Hz), 3.52 (1H, tt, J=6 Hz), 4.56 (2H, q, J=7 Hz), 7.49 (1H, s), 7.56 (1H, s), 8.44 (1H, d, J=2 Hz), 8.54 (1H, d, J=2 Hz)

EXAMPLE 353

A mixture of [4-(5-chloro-2-thienyl)-1-ethyl-6-isopropyl-1H-pyrazolo[3,4-b]pyridin-5-yl]methanol (2.526 g), activated manganese dioxide (13.1 g) in tetrachloromethane (50 ml) was refluxed for 12 hours. Another activated manganese dioxide (26.1 g) was added and the mixture was refluxed for 10 hours. After cooling, the mixture was filtered through celite and the filtrate was concentrated in vacuo. The residue was purified by flash column chromatography on silica gel eluting with a mixture of EtOAc and n-hexane (1:20) to give 4-(5-chloro-2-thienyl)-1-ethyl-6-isopropyl-1H-pyrazolo[3,4-b]pyridine-5-carbaldehyde (1.4 g) as a yellow crystal.

$^1$H-NMR (CDCl$_3$) δ 1.35 (6H, d, J=7 Hz), 1.56 (3H, t, J=7 Hz), 4.05 (1H, sep, J=7 Hz), 4.60 (2H, q, J=7 Hz), 7.04 (1H, d, J=1 Hz), 7.09 (1H, d, J=1 Hz), 8.10 (1H, s), 10.25 (1H, s)

The following compound(s) was(were) obtained in a similar manner to that of Example 353.

EXAMPLE 354

4-(2-Chloro-4-pyridyl)-6-cyclopentyl-1-ethyl-1H-pyrazolo[3,4-b]pyridine-5-carbaldehyde $^1$H-NMR (CDCl$_3$) δ 1.57 (3H, t, J=7 Hz), 1.73-1.83 (2H, m), 1.87-1.95 (2H, m), 2.02-2.14 (4H, m), 4.14 (1H, quintet, J=7 Hz), 4.60 (2H, q, J=7 Hz), 7.29 (1H, dd, J=4, 1 Hz), 7.43 (1H, t, J=1 Hz), 7.76 (1H, s), 8.57 (1H, d, J=4 Hz), 10.24 (1H, s)

EXAMPLE 355

1-Ethyl-6-isopropyl-4-{5-[(trimethylsilyl)ethynyl]-3-pyridyl}-1H-pyrazolo[3,4-b]pyridine-5-carbaldehyde $^1$H-NMR (CDCl$_3$) δ 0.29 (9H, s), 1.40 (6H, d, J=6.6 Hz), 1.58 (3H, t, J=6.7 Hz), 4.11 (1H, h, J=6.6 Hz), 4.62 (2H, q, J=6.7 Hz), 7.80 (1H, s), 7.83 (1H, s), 8.61 (1H, s), 8.82 (1H, s), 10.14 (1H, s)

EXAMPLE 356

1-Ethyl-4-(5-methoxy-3-pyridyl)-6-phenyl-1H-pyrazolo[3,4-b]pyridine-5-carbaldehyde $^1$H-NMR (CDCl$_3$) δ 1.59(3H, t, J=7Hz), 3.94(3H, s), 4.68 (2H, q, J=7Hz), 7.36(1H, t, J=1 Hz), 7.53-7.57 (3H, m), 7.64-7.68(2H, m), 7.90 (1H, s), 8.32 (1H, s), 8.45 (1H, s), 10.00 (1H, s)
MS (ESI$^+$) (m/z) 359(M+1)

EXAMPLE 357

1-Ethyl-6-(4-fluorophenyl)-4-(5-methyl-3-pyridyl)-1H-pyrazolo[3,4-b]pyridine-5-carbaldehyde $^1$H-NMR (CDCl$_3$) δ 1.60 (3H, t, J=7 Hz), 2.47 (3H, s), 4.65 (2H, q, J=7 Hz), 7.12-7.30 (2H, m), 7.60-7.69 (3H, m), 7.88 (1H, s), 8.54 (1H, bs), 8.60 (1H, bs), 10.11 (1H, s)

EXAMPLE 358

4-(2-Chloro-4-pyridyl)-6-cyclopropyl-1-ethyl-1H-pyrazolo[3,4-b]pyridine-5-carbaldehyde $^1$H-NMR (CDCl$_3$) δ 1.13-1.21 (2H, m), 1.34-1.40 (2H, m), 1.53 (3H, t, J=6.7 Hz), 3.24-3.32 (1H, m), 4.52 (2H, q, J=6.7 Hz), 7.30 (1H, d, J=4 Hz), 7.43 (1H, s), 7.73 (1H, s), 8.57 (1H, d, J=4 Hz), 10.23 (1H, s)

EXAMPLE 359

4-(5-Bromo-3-pyridyl)-6-cyclopentyl-1-ethyl-1H-pyrazolo[3,4-b]pyridine-5-carbaldehyde ¹H-NMR (CDCl₃) δ 1.72-1.83 (2H, m), 1.83-1.98 (2H, m), 1.57 (3H, t, J=7 Hz), 2.00-2.18 (4H, m), 4.10-4.22 (1H, m), 4.60 (2H, q, J=7 Hz), 7.79 (1H, s), 7.94 (1H, s), 8.62 (1H, s), 8.85 (1H, s), 10.24 (1H, s)

EXAMPLE 360

1-Ethyl-4-(5-methyl-3-pyridyl)-6-propyl-1H-pyrazolo[3,4-b]pyridine-5-carbaldehyde ¹H-NMR (CDCl₃) δ 1.10 (3H, t, J=6.7 Hz), 1.56 (3H, t, J=6.7 Hz), 1.78-1.90 (2H, m), 2.48 (3H, s), 3.30 (2H, t, J=6.7 Hz), 4.62 (2H, q, J=6.7 Hz), 7.60 (1H, s), 7.82 (1H, s), 8.55 (1H, s), 8.63 (1H, s)

EXAMPLE 361

4-(5-Bromo-3-pyridyl)-1-ethyl-6-(methoxymethyl)-1H-pyrazolo[3,4-b]pyridine-5-carbaldehyde ¹H-NMR (CDCl₃) δ 1.59 (3H, t, J=7 Hz), 3.57 (3H, s), 4.67 (2H, q, J=7 Hz), 5.05 (2H, s), 7.88 (1H, s), 7.97 (1H, t, J=1 Hz), 8.64 (1H, d, J=1 Hz), 8.87 (1H, d, J=1 Hz), 10.22 (1H, s)

EXAMPLE 362

6-Cyclobutyl-1-ethyl-4-(5-methyl-3-pyridyl)-1H-pyrazolo[3,4-b]pyridine-5-carbaldehyde ¹H-NMR (CDCl₃) δ 1.61 (3H, t, J=7Hz), 1.87-1.99 (1H, m), 2.06-2.16 (1H, m), 2.38-2.45 (2H, m), 2.47 (3H, s), 2.54-2.62 (2H, m), 4.50 (1H, quintet, J=7 Hz), 4.66 (2H, q, J=7Hz), 7.58 (1H, s), 7.82 (1H, s), 8.54 (1H, d, J=1 Hz), 8.62 (1H, d, J=1 Hz), 10.09 (1H, s)

MS (ESI⁺) m/z 321(M+1)

EXAMPLE 363

4-(5-Chloro-3-pyridyl)-6-cyclopropyl-1-ethyl-1H-pyrazolo[3,4-b]pyridine-5-carbaldehyde ¹H-NMR (CDCl₃) δ 1.15-1.20 (2H, m), 1.35-1.40 (2H, m), 1.52 (3H, t, J=7 Hz), 3.25-3.34 (1H, m), 4.52 (2H, q, J=7 Hz), 7.76 (1H, s), 7.80 (1H, s), 8.59 (1H, s), 8.75 (1H, s), 10.24 (1H, s)

EXAMPLE 364

6-(2,2-Dimethylpropyl)-1-ethyl-4-(5-methyl-3-pyridyl)-1H-pyrazolo[3,4-b]pyridine-5-carbaldehyde ¹H-NMR (CDCl₃) δ 1.03 (9H, s), 1.57 (3H, t, J=7 Hz), 2.47 (3H, s), 3.39 (2H, s), 4.62 (2H, q, J=7 Hz), 7.57 (1H, s), 7.83 (1H, s), 8.54 (1H, d, J=1 Hz), 8.61 (1H, d, J=1 Hz), 10.13 (1H, s)

MS (ESI⁺) m/z 337(M+1)

EXAMPLE 365

1-Ethyl-6-(1-ethylpropyl)-4-(5-methyl-3-pyridyl)-1H-pyrazolo[3,4-b]pyridine-5-carbaldehyde ¹H-NMR (CDCl₃) δ 0.85 (6H, t, J=7 Hz), 1.56 (3H, t, J=7 Hz), 1.71-1.84 (2H, m), 1.93-2.05 (2H, m), 2.46 (3H, s), 3.80-3.87 (2H, m), 4.63 (2H, q, J=7 Hz), 7.59 (1H, s), 7.83 (1H, s), 8.57 (1H, s), 8.62 (1H, s), 10.15 (1H, s)

EXAMPLE 366

1,6-Diethyl-4-(5-methyl-3-pyridyl)-1H-pyrazolo[3,4-b]pyridine-5-carbaldehyde

¹H-NMR (CDCl₃) δ 1.34 (3H, t, J=7 Hz), 1.46 (3H, t, J=7 Hz), 2.44 (3H, s), 3.25 (2H, q, J=7 Hz), 4.61 (2H, q, J=7 Hz), 7.60 (1H, s), 7.77 (1H, s), 8.54 (1H, s), 8.58 (1H, s), 10.10 (1H, s)

EXAMPLE 367

6-Butyl-1-ethyl-4-(5-methyl-3-pyridyl)-1H-pyrazolo[3,4-b]pyridine-5-carbaldehyde ¹H-NMR (CDCl₃) δ 1.00 (3H, t, J=7 Hz), 1.46-1.61 (5H, m), 1.74-1.84 (2H, m), 2.48 (3H, s), 3.33 (2H, t, J=7 Hz), 4.62 (2H, q, J=7 Hz), 7.60 (1H, s), 7.82 (1H, s), 8.55 (1H, s), 8.62 (1H, s), 10.10 (1H, s)

EXAMPLE 368

1-Ethyl-6-(2-fluorophenyl)-4-(5-methyl-3-pyridyl)-1H-pyrazolo[3,4-b]pyridine-5-carbaldehyde ¹H-NMR (CDCl₃) δ 1.59 (3H, t, J=6.7 Hz), 2.45 (3H, s), 4.65 (2H, q, J=6.7 Hz), 7.16 (1H, dd, J=7.7, 7.8 Hz), 7.35 (1H, dd, J=7.7, 7.7 Hz), 7.43-7.55 (1H, m), 7.55-7.71 (2H, m), 7.94 (1H, s), 8.56 (1H, s), 8.60 (1H, s), 10.00 (1H, s)

The following compound(s) was(were) obtained in a similar manner to that of Example 70.

EXAMPLE 369

4-(5-Chloro-2-thienyl)-6-cyclopropyl-1-ethyl-1H-pyrazolo[3,4-b]pyridine-5-carbaldehyde oxime ¹H-NMR (CDCl₃) δ 1.01-1.10 (2H, m), 1.25-1.30 (2H, m), 1.50 (3H, t, J=7 Hz), 2.66-2.77 (1H, m), 4.50 (2H, q, J=7 Hz), 7.04 (1H, d, J=4 Hz), 7.12 (1H, d, J=4 Hz), 7.46 (1H, s), 8.01 (1H, s), 8.40 (1H, s)

EXAMPLE 370

4-(2-Chloro-4-pyridyl)-1-ethyl-6-isopropyl-1H-pyrazolo[3,4-b]pyridine-5-carbaldehyde oxime ¹H-NMR (CDCl₃) δ 1.46 (6H, d, J=7 Hz), 1.56 (3H, t, J=7 Hz), 3.54 (1H, qq, J=7, 7 Hz), 4.60 (2H, q, J=7 Hz), 7.26-7.28 (1H, m), 7.40 (1H, s), 7.71 (1H, s), 7.97 (1H, s), 8.31 (1H, s), 8.49 (1H, d, J=6 Hz)

The following compound(s) was(were) obtained in a similar manner to that of Example 73.

EXAMPLE 371

4-(5-Chloro-2-thienyl)-6-cyclopropyl-1-ethyl-1H-pyrazolo[3,4-b]pyridine-5-carbonitrile $^1$H-NMR (CDCl$_3$) δ 1.19-1.36 (4H, m), 1.50 (3H, t, J=7 Hz), 2.68-2.76 (1H, m), 4.50 (2H, q, J=7 Hz), 7.10 (1H, d, J=4 Hz), 7.70 (1H, d, J=4 Hz), 8.20 (1H, s)

EXAMPLE 372

4-(2-Chloro-4-pyridyl)-1-ethyl-6-isopropyl-1H-pyrazolo[3,4-b]pyridine-5-carbonitrile $^1$H-NMR (CDCl$_3$) δ 1.45 (6H, d, J=6 Hz), 1.59 (3H, t, J=7 Hz), 3.76 (1H, qq, J=6, 6 Hz), 4.63 (2H, q, J=7 Hz), 7.54 (1H, dd, J=6, 1 Hz), 7.52-7.53 (1H, m), 7.93 (1H, s), 8.66 (1H, dd, J=6, 1 Hz)

EXAMPLE 373

To a solution of l3-[1-ethyl-6-isopropyl-4-(5-methyl-3-pyridyl)-1H-pyrazolo[3,4-b]pyridin-5-yl]propanoic acid (40 mg) in DCM (1.5 ml) was added 1-(3-dimethylaminopropyl)-3-ethylcarbodiimide hydrochloride (28.3 mg), methylamine (1N THF solution, 0.2 ml) and the mixture was stirred at room temperature for 10 minutes. 4-Dimethylaminopyridine (1.7 mg) was added to this mixture and the resulting mixture was stirred at room temperature for 5 hours. The mixture was diluted with water and extracted with EtOAc. The organic layer was washed with water, brine, dried over anhydrous MgSO$_4$ and concentrated in vacuo. The residue was purified by preparative thin layer chromatography on silica gel eluting with a mixture of MeOH and CHCl$_3$ (1:20). The residue was treated with n-hexane to give a solid which was washed with IPE to give 3-[1-ethyl-6-isopropyl-4-(5-methyl-3-pyridyl)-1H-pyrazolo[3,4-b]pyridin-5-yl]-N-methylpropanamide (24 mg) as a colorless crystal.

$^1$H-NMR (CDCl$_3$) δ 1.38 (6H, d, J=7 Hz), 1.55 (3H, t, J=7 Hz), 2.23 (2H, t, J=7 Hz), 2.45 (3H, s), 2.94-3.06 (2H, m), 3.46 (1H, sep, J=7 Hz), 4.57 (2H, q, J=7 Hz), 5.27-5.36 (1H, m), 7.50 (1H, s), 7.51 (1H, s), 8.43 (1H, s), 8.55 (1H, s)

MS (ESI$^+$) m/z 366(M+1)

EXAMPLE 374

To a mixture of 5-cyano-1-ethyl-4-(5-methyl-3-pyridyl)-1H-pyrazolo[3,4-b]pyridin-6-yl trifluoromethanesulfonate (253 mg), 4-fluorobenzeneboronic acid (129 mg), powdered potassium phosphonate (195 mg) in 1,4-dioxane (4 ml) was added tetrakis(triphenylphosphine)palladium(0) (18 mg) at room temperature. The mixture was refluxed for 7 hours. Resulting mixture was diluted with EtOAc (10 ml), washed with water (×2) and brine and dried over MgSO$_4$. The solvent was evaporated and the residue was purified with silica gel column chromatography to give 1-ethyl-6-(4-fluorophenyl)-4-(5-methyl-3-pyridyl)-1H-pyrazolo[3,4-b]pyridine-5-carbonitrile (175 mg) as colorless solid.

$^1$H-NMR (CDCl$_3$) δ 1.61 (3H, t, J=6.5 Hz), 2.51 (3H, s), 4.68 (2H, q, J=6.5 Hz), 7.21-7.31 (2H, m), 7.90 (1H, s), 7.95 (1H, d, J=7.8 Hz), 7.97 (1H, d, J=7.8 Hz), 8.03 (1H, s), 8.67 (1H, s), 8.78 (1H, s)

The invention claimed is:
1. A compound of formula (I):

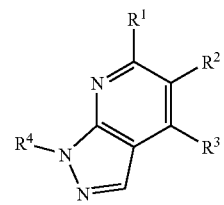

in which
R$^1$ is (1) lower alkyl optionally substituted by halogen, cyclo(lower)alkyl, lower alkoxy, hydroxy, protected hydroxy, cyclo(lower)alkyloxy, aryloxy, hydroxyimino, carbamoyloxy optionally substituted by lower alkyl, or substituted or unsubstituted heterocyclyl, wherein said lower alkoxy is optionally substituted by cyclo(lower)alkyl, substituted or unsubstituted aryl, or substituted or unsubstituted heteroaryl,
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;
R$^2$ is hydroxy, protected hydroxy, cyano, carboxy, hydroxyimino(lower)alkyl, —CONR$^6$R$^7$ or -(A$^1$)p-X-A$^2$-R$^5$,
wherein
p is 0 or 1
A$^1$ is (C$_1$-C$_2$)alkylene or —CH=CH—;
A$^2$ is a divalent heterocyclic group, or —(CH$_2$)$_n$— or —(CH=CH)$_m$—, wherein n is integer which may range from 1 to 6 and m is integer which may range from 1 to 3;
X is single bond, —CH$_2$— or —O—, and
R$^5$ is protected hydroxy, cyano, carboxy, protected carboxy, hydroxyimino(lower)alkyl, or —CONR$^6$R$^7$
wherein R$^6$ is hydrogen or lower alkyl, and R$^7$ is hydrogen or —(CH$_2$)$_q$—Y—R$^8$, wherein q is 0, 1, 2 or 3, Y is bond, —O—, or —CH(R$^9$)—CH$_2$—, wherein R$^9$ is lower alkyl, carboxy or protected carboxy, and R$^8$ is (1) lower alkyl, (2) substituted or unsubstituted aryl, (3) substituted or unsubstituted heteroaryl, (4) substituted or unsubstituted heterocyclyl, or (5) substituted or unsubstituted cyclo(lower)alkyl), or alternatively R$^6$ and R$^7$, together with the nitrogen atom to which they are attached, represent substituted or unsubstituted azaheterocyclyl group;
R$^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and
R$^4$ is lower alkyl,
or a pharmaceutically acceptable salt thereof.
2. The compound of claim 1, in which
R$^1$ is (1) lower alkyl optionally substituted by halogen, cyclo(lower)alkyl, lower alkoxy, hydroxy, lower alkyldiphenylsilyloxy, cyclo(lower)alkyloxy, phenoxy, hydroxyimino, carbamoyloxy optionally substituted by lower alkyl, or a radical of saturated monocyclic ring system comprising 5 or 6 ring atoms and containing one to three heteroatom(s) selected from the group consisting of nitrogen, oxygen and sulfur, wherein said lower alkoxy is optionally substituted by cyclo(lower)alkyl, aryl, or a radical of aromatic monocyclic ring system comprising 5 or 6 ring atoms and containing one to three heteroatom(s) selected from the group consisting of nitrogen, oxygen and sulfur, said radical is optionally substituted by lower alkyl,
  (2) lower alkenyl optionally substituted by cyano or carbamoyl optionally substituted by aryl which may have halogen,
  (3) cyclo(lower)alkyl,
  (4) lower alkanoyl,
  (5) cyano,
  (6) phenyl optionally substituted by lower alkyl, lower alkoxy or halogen, or
  (7) a radical of aromatic monocyclic ring system comprising 5 or 6 ring atoms and containing one to three heteroatom(s) selected from the group consisting of nitrogen, oxygen and sulfur, which is optionally substituted by lower alkyl;

$R^2$ is hydroxy, protected hydroxy, cyano, carboxy, hydroxyimino(lower)alkyl, —$CONR^6R^7$ or -$(A^1)p$-X-$A^2$-$R^5$,
  wherein $A^1$, p and X are each as defined in claim 1, and
  $A^2$ is a divalent group derived from a radical of saturated monocyclic ring system comprising 5 or 6 ring atoms and containing one to three heteroatom(s) selected from the group consisting of nitrogen, oxygen and sulfur, or —$(CH_2)_n$— or —$(CH=CH)_m$—, wherein n is integer which may range from 1 to 4 and m is 1 or 2;
  $R^5$ is protected hydroxy, cyano, carboxy, esterified carboxy, hydroxyimino(lower)alkyl, or —$CONR^6 R^7$
    wherein $R^6$ is hydrogen, and $R^7$ is —$(CH_2)_q$—Y—$R^8$ wherein q is 0, 1, 2 or 3, Y is bond or —O—, and $R^8$ is phenyl or indanyl, each of which is optionally substituted by lower alkoxy;

$R^3$ is (1) phenyl optionally substituted by one or more substituent(s) selected from the group consisting of halogen, lower alkyl, lower alkoxy and amino,
  (2) a radical of aromatic monocyclic ring system comprising 5 or 6 ring atoms and containing one to three heteroatom(s) selected from the group consisting of nitrogen, oxygen and sulfur, which is optionally substituted by lower alkyl, halogen or lower alkoxy,
  (3) tetrahydropyranyl,
  (4) cyclohexyl, or
  (5) cyclohexylmethyl or phenylethyl; and
$R^4$ is lower alkyl,
or a pharmaceutically acceptable salt thereof.

3. The compound of claim 2, wherein
$R^1$ is (1) lower alkyl optionally substituted by halogen, cyclo(lower)alkyl, lower alkoxy, hydroxy, lower alkyldiphenylsilyloxy, cyclo(lower)alkoxy, phenoxy, hydroxyimino, carbamoyloxy optionally substituted by lower alkyl, or morpholinyl, wherein said lower alkoxy is optionally substituted by cyclo(lower)alkyl, phenyl, or pyridyl optionally substituted by lower alkyl,
  (2) lower alkenyl optionally substituted by cyano or carbamoyl optionally substituted by aryl which may have halogen,
  (3) cyclo(lower)alkyl,
  (4) lower alkanoyl,
  (5) cyano,
  (6) phenyl optionally substituted by lower alkyl, lower alkoxy or halogen, or
  (7) oxazolyl or thienyl, each of which is optionally substituted by lower alkyl;

$R^2$ is hydroxy, protected hydroxy, cyano, carboxy, hydroxyimino(lower)alkyl, —$CONR^6R^7$ or -$(A^1)p$-X-$A^2$-$R^5$,
  wherein $R^5$, $R^6$, $R^7$, $A^1$, p and X are each as defined in claim 2, and
  $A^2$ is a divalent group derived from piperidine or piperazine, or —$(CH_2)_n$— or —$(CH=CH)_m$—, wherein n is integer which may range from 1 to 4 and m is 1 or 2;

$R^3$ is (1) phenyl optionally substituted by halogen, lower alkyl or lower alkoxy,
  (2) phenyl substituted by two halogen atoms and amino,
  (3) pyridyl or thienyl, each of which is optionally substituted by lower alkyl, alkyne, halogen or lower alkoxy,
  (4) cyclohexyl, or
  (5) cyclohexylmethyl or phenylethyl; and
$R^4$ is ethyl,
or a pharmaceutically acceptable salt thereof.

4. The compound of claim 3, wherein
$R^1$ is (1) lower alkyl optionally substituted by lower alkoxy, hydroxy, cyclo(lower)alkoxy, phenoxy, carbamoyloxy optionally substituted by lower alkyl, or morpholinyl,
  (2) lower alkanoyl, or
  (3) phenyl optionally substituted by lower alkyl, lower alkoxy or halogen; and
$R^3$ is (1) phenyl optionally substituted by halogen, lower alkyl or lower alkoxy, or
  (2) pyridyl optionally substituted by lower alkyl, alkyne, halogen or lower alkoxy,
or a pharmaceutically acceptable salt thereof.

5. A compound of claim 4, which is
(1) 1-Ethyl-4-(5-methyl-3-pyridyl)-6-phenyl-1H-pyrazolo[3,4-b]pyridine-5-carboxylic acid,
(2) 1-Ethyl-N-(4-methoxybenzyl)-4-(5-methyl-3-pyridyl)-6-phenyl-1H-pyrazolo[3,4-b]pyridine-5-carboxamide,
(3) 4-(5-bromo-3-pyridyl)-1-ethyl-6-methyl-1H-pyrazolo[3,4-b]pyridine-5-carbonitrile,
(4) (2E)-3-[4-(5-Bromo-3-pyridyl)-1-ethyl-6-methyl-1H-pyrazolo[3,4-b]pyridin-5-yl]acrylic acid,
(5) (2E)-3-[6-[(Cyclohexylmethoxy)methyl]-1-ethyl-4-(5-methyl-3-pyridyl)-1H-pyrazolo[3,4-b]pyridin-5-yl]acrylic acid,
(6) (2E)-3-[1-Ethyl-4-(5-methyl-3-pyridyl)-6-phenyl-1H-pyrazolo[3,4-b]pyridin-5-yl]acrylic acid,
(7) 3-[1-Ethyl-4-(5-methyl-3-pyridyl)-6-phenyl-1H-pyrazolo[3,4-b]pyridin-5-yl]propanoic acid,
(8) 3-[1-Ethyl-4-(5-methyl-3-pyridyl)-6-(4-morpholinylmethyl)-1H-pyrazolo[3,4-b]pyridin-5-yl]propanoic acid,
(9) Ethyl (2E)-3-(1-ethyl-4,6-diphenyl-1H-pyrazolo[3,4-b]pyridin-5-yl)acrylate,
(10) Ethyl (2E)-3-[1-ethyl-6-isobutyl-4-(5-methyl-3-pyridyl)-1H-pyrazolo[3,4-b]pyridin-5-yl]acrylate,
(11) (2E)-3-(1-Ethyl-4,6-diphenyl-1H-pyrazolo[3,4-b]pyridin-5-yl)acrylic acid,
(12) (2E)-3-[1-Ethyl-6-isobutyl-4-(5-methyl-3-pyridyl)-1H-pyrazolo[3,4-b]pyridin-5-yl]acrylic acid,
(13) 1-Ethyl-4-(5-methyl-3-pyridyl)-N-(2-phenoxyethyl)-6-phenyl-1H-pyrazolo[3,4-b]pyridine-5-carboxamide,

(14) 3-(1-Ethyl-4,6-diphenyl-1H-pyrazolo[3,4-b]pyridin-5-yl)propanoic acid,
(15) 3-[1-Ethyl-6-(2-fluorophenyl)-4-(5-methyl-3-pyridyl)-1H-pyrazolo[3,4-b]pyridin-5-yl]propanoic acid,
(16) 3-[1-Ethyl-6-isopropyl-4-(2-methyl-4-pyridyl)-1H-pyrazolo[3,4-b]pyridin-5-yl]propanoic acid, or a pharmaceutically acceptable salt thereof.

6. A compound of claim 5, which is
(1) 4-(5-bromo-3-pyridyl)-1-ethyl-6-methyl-1H-pyrazolo[3,4-b]pyridine-5-carbonitrile,
(2) (2E)-3-[4-(5-Bromo-3-pyridyl)-1-ethyl-6-methyl-1H-pyrazolo[3,4-b]pyridin-5-yl]acrylic acid,
(3) (2E)-3-[6-[(Cyclohexylmethoxy)methyl]-1-ethyl-4-(5-methyl-3-pyridyl)-1H-pyrazolo[3,4-b]pyridin-5-yl]acrylic acid,
(4) (2E)-3-[1-Ethyl-4-(5-methyl-3-pyridyl)-6-phenyl-1H-pyrazolo[3,4-b]pyridin-5-yl]acrylic acid,
(5) 3-[1-Ethyl-4-(5-methyl-3-pyridyl)-6-phenyl-1H-pyrazolo[3,4-b]pyridin-5-yl]propanoic acid,
(6) Ethyl (2E)-3-(1-ethyl-4,6-diphenyl-1H-pyrazolo[3,4-b]pyridin-5-yl)acrylate,
(7) (2E)-3-(1-Ethyl-4,6-diphenyl-1H-pyrazolo[3,4-b]pyridin-5-yl)acrylic acid, or
(8) 1-Ethyl-4-(5-methyl-3-pyridyl)-N-(2-phenoxyethyl)-6-phenyl-1H-pyrazolo[3,4-b]pyridine-5-carboxamide, or a pharmaceutically acceptable salt thereof.

7. A process for preparing the pyrazolopyridine compound of formula (I) according to claim 1, which comprises reacting a compound of the formula (II):

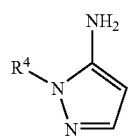
(II)

wherein $R^4$ is as defined in claim 1, or a salt thereof, with a compound of the formula (III):

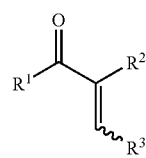
(III)

wherein $R^1$, $R^2$ and $R^3$ are each as defined in claim 1, or a salt thereof, to give a compound of formula (I).

8. A pharmaceutical composition which comprises, as an active ingredient, a compound of claim 1 in admixture with pharmaceutically acceptable carriers.

9. A process for preparing a pyrazolpyridine compound of formula (I-2), or a salt thereof:

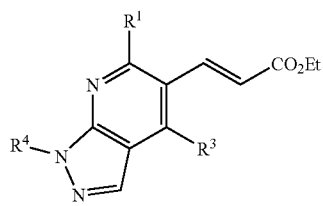
(I-2)

wherein
$R^1$ is (1) lower alkyl optionally substituted by halogen, cyclo(lower)alkyl, lower alkoxy, hydroxy, protected hydroxy, cyclo(lower)alkyloxy, aryloxy, hydroxyimino, carbamoyloxy optionally substituted by lower alkyl, or substituted or unsubstituted heterocyclyl, wherein said lower alkoxy is optionally substituted by cyclo(lower)alkyl, substituted or unsubstituted aryl, or substituted or unsubstituted heteroaryl,
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;
$R^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and
$R^4$ is lower alkyl;
which process comprises subjecting a compound of formula (I-1), or a salt thereof, to Wittig reaction to give the compound of formula (1-2),

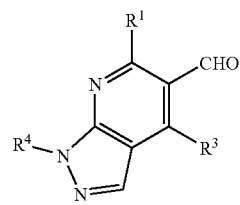
(I-1)

wherein $R^1$, $R^3$ and $R^4$ are each as defined above.

10. A process for preparing a pyrazolpyridine compound of formula I-4), or a salt thereof:

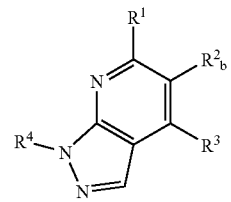
(I-4)

wherein
$R^1$ is (1) lower alkyl optionally substituted by halogen, cyclo(lower)alkyl, lower alkoxy, hydroxy, protected hydroxy, cyclo(lower)alkyloxy, aryloxy, hydroxyimino, carbamoyloxy optionally substituted by lower alkyl, or substituted or unsubstituted heterocyclyl, wherein said lower alkoxy is optionally substituted by cyclo(lower)alkyl, substituted or unsubstituted aryl, or substituted or unsubstituted heteroaryl,
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;

$R^2_b$ is a carboxy or -(A$^1$)p-X-A$^2$-R$^5$,
wherein
p is 0 or 1
A$^1$ is (C$_1$-C$_2$)alkylene or —CH=CH—;
A$^2$ is a divalent heterocyclic group, or —(CH$_2$)$_n$— or —(CH=CH)$_m$—, wherein n is integer which may range from 1 to 6 and m is integer which may range from 1 to 3;
X is single bond, —CH$_2$— or —O—, and
R$^5$ is carboxy or —CONR$^6$R$^7$
wherein R$^6$ is hydrogen or lower alkyl, and R$^7$ is —(CH$_2$)q—Y—R$^8$, wherein q is 0, 1, 2 or 3, Y is —CH(R$^9$)—CH$_2$—, wherein R$^9$ is carboxy, and R$^8$ is (1) lower alkyl, (2) substituted or unsubstituted aryl, (3) substituted or unsubstituted heteroaryl, (4) substituted or unsubstituted heterocyclyl, or (5) substituted or unsubstituted cyclo(lower)alkyl;
R$^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and
R$^4$ is lower alkyl;
which process comprises subjecting a compound of formula (I-3), or a salt thereof, to hydrolysis to give the compound of formula (I-4)

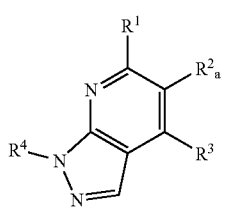

(I-3)

wherein R$^1$, R$^3$ and R$^4$ are each as defined above, and
$R^2_a$ is a protected carboxy or -(A$^1$)p-X-A$^2$-R$^5$,
wherein
p is 0 or 1
A$^1$ is (C$_1$-C$_2$)alkylene or —CH=CH—;
A$^2$ is a divalent heterocyclic group, or —(CH$_2$)$_n$— or —(CH=CH)$_m$—, wherein n is integer which may range from 1 to 6 and m is integer which may range from 1 to 3;
X is single bond, —CH$_2$— or —O—, and
R$^5$ is protected carboxy or —CONR$^6$R$^7$
wherein R$^6$ is hydrogen or lower alkyl, and R$^7$ is —(CH$_2$)q—Y—R$^8$, wherein q is 0, 1, 2 or 3, Y is —CH(R$^9$)—CH$^2$—, wherein R$^9$ is protected carboxy, and R$^8$ is (1)lower alkyl, (2) substituted or unsubstituted aryl, (3) substituted or unsubstituted heteroaryl, (4) substituted or unsubstituted hererocyclyl, or (5) substituted or unsubstituted cyclo(lower)alkyl.

11. A process for preparing a pyrazolpyridine compound of formula (I-5), or a salt thereof:

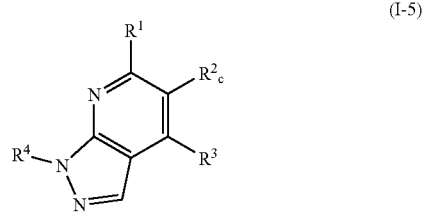

(I-5)

wherein
R$^1$ is (1) lower alkyl optionally substituted by halogen, cyclo(lower)alkyl, lower alkoxy, hydroxy, protected hydroxy, cyclo(lower)alkyloxy, aryloxy, hydroxyimino, carbamoyloxy optionally substituted by lower alkyl, or substituted or unsubstituted heterocyclyl, wherein said lower alkoxy is optionally substituted by cyclo(lower)alkyl, substituted or unsubstituted aryl, or substituted or unsubstituted heteroaryl,
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;
$R^2_c$ is a —CONRR$^6$R$^7$ or -(A$^1$)p-X-A$^2$-R$^5$,
wherein
p is 0 or 1
A$^1$ is (C$_1$-C$_2$)alkylene or —CH=CH—;
A$^2$ is a divalent heterocyclic group, or —(CH$_2$)$_n$— or —(CH=CH)$_m$—, wherein n is integer which may range from 1 to 6 and m is integer which may range from 1 to 3;
X is single bond, —CH$_2$— or —O—, and
R$^5$ is —CONRR$^6$R$^7$,
wherein R$^6$ is hydrogen or lower alkyl, and R$^7$ is hydrogen or —(CH$_2$)$_q$—Y—R$^8$, wherein q is 0, 1, 2 or 3, Y is bond, —O—, or —CH(R$^9$)—CH$_2$—, wherein R$^9$ is lower alkyl, carboxy or protected carboxy, and R$^8$ is (1) lower alkyl, (2) substituted or unsubstituted aryl, (3) substituted or unsubstituted heteroaryl, (4) substituted or unsubstituted heterocyclyl, or (5) substituted or unsubstituted cyclo(lower)alkyl, or
alternatively R$^6$ and R$^{7'}$ together with the nitrogen atom to which they are attached, represent substituted or unsubstituted azaheterocyclyl group;
R$^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and
R$^4$ is lower alkyl;
which process comprises amidating a compound of formula (I-4), or a salt thereof to give the compound of formula (I-5)

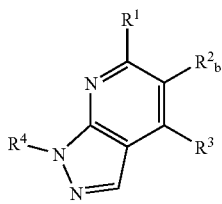

(I-4)

wherein $R^1$, $R^3$ and $R^4$ are each as defined, and $R^2_b$ is a carboxy or $-(A^1)p-X-A^2-R^5$,
wherein
p is 0 or 1
$A^1$ is ($C_1$-$C_2$)alkylene or —CH=CH—;
$A^2$ is a divalent heterocyclic group, or —$(CH_2)_n$— or —$(CH=CH)_m$—, wherein n is integer which may range from 1 to 6 and m is integer which may range from 1 to 3;
X is single bond, —$CH_2$— or —O—, and
$R^5$ is carboxy.

12. A process for preparing a pyrazolpyridine compound of formula (I-7), or a salt thereof:

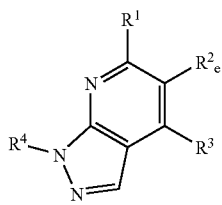

(I-7)

wherein
$R^1$ is (1) lower alkyl optionally substituted by halogen, cyclo(lower)alkyl, lower alkoxy, hydroxy, protected hydroxy, cyclo(lower)alkyloxy, aryloxy, hydroxyimino, carbamoyloxy optionally substituted by lower alkyl, or substituted or unsubstituted heterocyclyl, wherein said lower alkoxy is optionally substituted by cyclo(lower)alkyl, substituted or unsubstituted aryl, or substituted or unsubstituted heteroaryl,
(2) lower alkenyl optionally substituted by cyano or carbamoyl optionally substituted by aryl which may have halogen,
(3) cyclo(lower)alkyl,
(4) acyl,
(5) cyano,
(6) substituted or unsubstituted aryl, or
(7) substituted or unsubstituted heteroaryl;
$R^2_e$ is $-(A^1)p-X-A^2-R^5$,
wherein
p is 0 or 1
$A^1$ is ($C_1$-$C_2$)alkylene;
$A^2$ is a divalent heterocyclic group or —$(CH_2)_n$—, wherein n is integer which may range from 1 to 6;
X is single bond, —$CH_2$— or —O—, and
$R^5$ is protected hydroxy, cyano, carboxy, protected carboxy, hydroxyimino(lower)alkyl, or —$CONR^6R^7$
wherein $R^6$ is hydrogen or lower alkyl, and $R^7$ is hydrogen or —$(CH_2)_q$—Y—$R^8$,
wherein q is 0, 1, 2 or 3, Y is bond, —O—, or —CH($R^9$)—$CH_2$—, wherein $R^9$ is lower alkyl, carboxy or protected carboxy, and $R^8$ is (1) lower alkyl, (2) substituted or unsubstituted aryl, (3) substituted or unsubstituted heteroaryl, (4) substituted or unsubstituted heterocyclyl, or (5) substituted or unsubstituted cyclo(lower)alkyl, or
alternatively $R^6$ and $R^7$, together with the nitrogen atom to which they are attached, represent substituted or unsubstituted azaheterocyclyl group;
$R^3$ is (1) substituted or unsubstituted aryl,
(2) substituted or unsubstituted heteroaryl,
(3) substituted or unsubstituted heterocyclyl,
(4) cyclo(lower)alkyl, or
(5) lower alkyl optionally substituted by (a) cyclo(lower)alkyl, (b) substituted or unsubstituted heterocyclyl, (c) substituted or unsubstituted aryl, or (d) substituted or unsubstituted heteroaryl; and
$R^4$ is lower alkyl;
which process comprises reducing a compound of formula (I-6), or a salt thereof, to give the compound of formula (I-7)

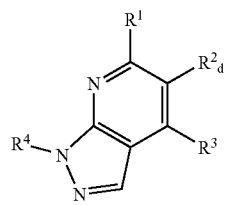

(I-6)

wherein $R^1$, $R^3$ and $R^4$ are each as defined above, and $R^2_d$ is $-(A^1)p-X-A^2-R^5$,
wherein
p is 0 or 1
$A^1$ is ($C_1$-$C_2$)alkylene or —CH=CH—;
$A^2$ is a divalent heterocyclic group, or —$(CH_2)_n$— or —$(CH=CH)_m$—, wherein n is integer which may range from 1 to 6 and m is integer which may range from 1 to 3;
X is single bond, —$CH_2$— or —O—, and
$R^5$ is protected hydroxy, cyano, carboxy, protected carboxy, hydroxyimino(lower)alkyl, or —$CONR^6R^7$
wherein $R^6$ is hydrogen or lower alkyl and $R^7$ is hydrogen or —$(CH_2)_q$—Y—$R^8$,
wherein q is 0, 1, 2 or 3, Y is bond, —O—, or —CH($R^9$)—$CH_2$—, wherein $R^9$ is lower alkyl, carboxy or protected carboxy, and $R^8$ is (1) lower alkyl, (2) substituted or unsubstituted aryl, (3) substituted or unsubstituted heteroaryl, (4) substituted or unsubstituted heterocyclyl, or (5) substituted or unsubstituted cyclo(lower)alkyl, or
alternatively $R^6$ and $R^7$, together with the nitrogen atom to which they are attached, represent substituted or unsubstituted azaheterocyclyl group;
provided that $A^1$ is —CH=CH— or $A^2$ is —$(CH=CH)_m$—.

* * * * *

UNITED STATES PATENT AND TRADEMARK OFFICE
CERTIFICATE OF CORRECTION

| | | |
|---|---|---|
| PATENT NO. | : 7,459,451 B2 | Page 1 of 1 |
| APPLICATION NO. | : 11/171320 | |
| DATED | : December 2, 2008 | |
| INVENTOR(S) | : Yoshito Abe et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 556 days.

Signed and Sealed this
Second Day of October, 2012

David J. Kappos
*Director of the United States Patent and Trademark Office*